(12) United States Patent
Shirtliff et al.

(10) Patent No.: US 8,697,375 B2
(45) Date of Patent: Apr. 15, 2014

(54) IN VIVO BIOFILM INFECTION DIAGNOSIS AND TREATMENT

(75) Inventors: Mark E. Shirtliff, Ellicott City, MD (US); Rebecca A. Brady, Laurel, MD (US); Jeffrey G. Leid, Flagstaff, AZ (US); Timothy L. Vail, Parks, AZ (US); Jennifer M. Kofonow, Philadelphia, PA (US)

(73) Assignees: University of Maryland, Baltimore, Baltimore, MD (US); Arizona Board of Regents A Body Corporate of the State of Arizona, Flagstaff, AZ (US)

( * ) Notice: Subject to any disclaimer, the term of this patent is extended or adjusted under 35 U.S.C. 154(b) by 34 days.

(21) Appl. No.: 13/061,142

(22) PCT Filed: Sep. 2, 2009

(86) PCT No.: PCT/US2009/055689
§ 371 (c)(1),
(2), (4) Date: Feb. 26, 2011

(87) PCT Pub. No.: WO2010/028013
PCT Pub. Date: Mar. 11, 2010

(65) Prior Publication Data
US 2011/0171123 A1    Jul. 14, 2011

Related U.S. Application Data

(60) Provisional application No. 61/093,597, filed on Sep. 2, 2008.

(51) Int. Cl.
C12Q 1/68 (2006.01)
G01N 33/53 (2006.01)
G01N 33/567 (2006.01)
G01N 33/569 (2006.01)

(52) U.S. Cl.
USPC ....... 435/7.33; 435/6.15; 435/7.21; 435/7.32; 435/7.92; 435/29; 435/34; 435/174; 435/176; 435/287.1; 435/287.2

(58) Field of Classification Search
None
See application file for complete search history.

(56) References Cited

U.S. PATENT DOCUMENTS 6,583,275 B1    6/2003    Doucette-Stamm et al.
7,220,401 B2    5/2007    Lanza et al.
(Continued)

FOREIGN PATENT DOCUMENTS

WO    91/08485 A1    6/1991
WO    03/096990 A2    11/2003
(Continued)

OTHER PUBLICATIONS

Suci et al., (Chem & Biol, Apr. 2007. vol. 14:387-398).*
(Continued)

*Primary Examiner* — Ja'Na Hines
(74) *Attorney, Agent, or Firm* — Nevrivy Patent Law Group P.L.L.C.

(57) ABSTRACT

The present invention relates to a method for in vivo detection of a biofilm infection residing in a mammal, the method comprising (i) administering to the mammal a diagnostic-effective amount of a biofilm-specific probe, wherein the probe comprises a biofilm-targeting moiety and a paramagnetic nanoparticle core; and (ii) imaging the mammal to detect the presence of the biofilm infection by observing the mammal using a magnetic resonance diagnostic technique after the biofilm-specific probe has been provided sufficient time to selectively bind to the biofilm infection that may be present in the mammal. The invention also relates to methods of treatment of a biofilm infection, and compositions and kits useful in the detection and/or treatment of biofilm infections.

15 Claims, 4 Drawing Sheets

In vivo Imaging of a Biofilm Infection

Paramagnetic Nanoparticles

(56) References Cited

U.S. PATENT DOCUMENTS

| | | | |
|---|---|---|---|
| 7,863,032 B2 | 1/2011 | Berka et al. | |
| 8,541,006 B2 | 9/2013 | Leid et al. | |
| 2004/0248856 A1* | 12/2004 | Lanza et al. | 514/124 |
| 2006/0173362 A1* | 8/2006 | Toms et al. | 600/478 |
| 2007/0059245 A1* | 3/2007 | Young et al. | 424/9.34 |
| 2007/0154965 A1* | 7/2007 | Zhang et al. | 435/7.23 |

FOREIGN PATENT DOCUMENTS

| | | |
|---|---|---|
| WO | 2008/096279 | 8/2008 |
| WO | 2008/105902 | 9/2008 |

OTHER PUBLICATIONS

Brady et al., Identification of *Staphylococcus aureus* proteins recognized by the antibody-mediated immune response to a biofilm infection, Infect. Immun., 74:3415-3426 (2006), American Society for Microbiology, Washington, D.C.

Cosgrove et al., The impact of methicillin resistance in *Staphylococcus aureus* bacteremia on patient outcomes: mortality, length of stay, and hospital charges, Infect. Control Hosp. Epidemiol., 26:166-174 (2005), The University of Chicago Press, Chicago, IL.

Costeron et al., The application of biofilm science to the study and control of chronic bacterial infections, J. Clin. Invest., 112:1466-1477 (2003), American Society for Clinical Investigation, Ann Arbor, Michigan.

Jefferson et al., Use of confocal microscopy to analyze the rate of vancomycin penetration through *Staphylococcus aureus* biofilms, Antimicrob Agents Chemother., 49:2467-2473 (2005), American Society for Microbiology, Washington, D.C.

Jesaitis et al., Compromised host defense on *Pseudomonas aeruginosa* biofilms: characterization of neutrophil and biofilm interactions, J. Immunol., 171:4329-4339 (2003), The American Association of Immunologists, Bethesda, Maryland.

Kobayashi et al., Brief ultrasonication improves detection of biofilm-formative bacteria around a metal implant, Clin. Orthop. Relat. Res., 457:210-213 (Apr. 2007), The Association of Bone and Joint Surgeons, Rosemont, IL.

Lambert et al., Enzyme-linked immunosorbent assay for the detection of antibodies to exocellular proteins of *Staphylococcus aureus* in bone infection, Fems Microbiology Letters, 100:67-70 (1992), Wiley-Blackwell, United Kingdom., United Kingdom.

Leid et al., Immunology of Staphylococcal biofilm infections in the eye: new tools to study endophthalmitis, DNA Cell Biol., 21:405-413 (2002), Mary Ann Liebert, Inc., New Rochelle, NY.

Leid et al., Human Leukocytes Adhere to, Penetrate, and Respond to *Staphylococcus aureus* Biofilms, Infect. Immun., 70:6339-6345 (2002), American Society for Microbiology, Washington, D.C.

Leid et al., The exopolysaccharide alginate protects *Pseudomonas aeruginosa* biofilm bacteria from IFN-gamma-mediated macrophage killing, J. Immunol., 175:7512-7518 (2005), The American Association of Immunologists, Bethesda, Maryland.

Mack et al., Biofilm formation in medical device-related infection, Int. J. Artif. Organs, 29:343-359 (2006), European Society for Artificial Organs, Italy.

O'Toole et al., Biofilm Formation as Microbial Development, Annu. Rev. Microbiol., 54:49-79 (2000), Annual Reviews, Palo Alto, CA.

Parsek et al., Bacterial Biofilms: An Emerging Link to Disease Pathogenesis, Annu. Rev. Microbiol, 57:677-701 (2003), Annual Reviews, Palo Alto, CA.

Sanderson et al., Bacterial biofilms on the sinus mucosa of human subjects with chronic rhinosinusitis, Laryngoscope, 116:1121-1126 (2006), Wiley-Blackwell, United Kingdom.

Selan et al., Diagnosis of vascular graft infections with antibodies against staphylococcal slime antigens, Lancet, 359: 2166-2168 (2002), Elsevier Limited, The Netherlands.

Shirtliff et al., Molecular interactions in biofilms, Chem. Biol., 9:859-871 (2002), Elsevier Limited, The Netherlands.

Trampuz et al., Diagnosis and treatment of infections associated with fracture-fixation devices, Injury, 37:S59-S66 (2006), Elsevier Limited, The Netherlands.

Tyski et al., Lipase versus teichoic acid and alpha-toxin as antigen in an enzyme immunoassay for serological diagnosis of *Staphylococcus aureus* infections, Eur. J. Clin. Microbiol. Infect. Dis., 10:447-449 (1991), Springer, Germany.

Veeh et al., Detection of *Staphylococcus aureus* bioflim on tampons and menses components, J. Infect. Dis., 188:519-530 (2003), Oxford Journals, United Kingdom.

Watkin et al., The serological diagnosis of staphylococcal infective endocarditis, J. Infect., 53:301-307 (2006), Elsevier Limited, The Netherlands.

Ymele-Leki et al., Erosion from *Staphylococcus aureus* biofilms grown under physiologically relevant fluid shear forces yields bacterial cells with reduced avidity to collagen, Appl. Environ. Microbiol., 73:1834-1841 (Mar. 2007), American Society for Microbiology, Washington, D.C.

Rafiq et al., Serological Detection of Gram-positive bacterial infection around prosthesis, Journal of Bone and Joint Surgery, 82-B:1156-1161 (2000), British Editorial Society for Bone and Joint Surgery, United Kingdom.

NCBI submission YP_039889. Retrieved from the Internet Jul. 31, 2012: <http://www.ncbi.nlm.nih.gov/protein/YP_039889>.

Brady et al., Immunoglobulins to surface-associated Biofilm Immunogens provide a novel means of visualization of methicillin-resistant *Staphylococcus aureus* Biofilms, Applied and Environmental Microbiology, 73:6612-6619 (Oct. 2007), American Society for Microbiology, Washington, D.C.

Gupta et al., Synthesis and surface engineering of iron oxide nanoparticles for biomedical applications, Biomaterials, 26:995-402 (2005), Elsevier Science Publishers BV., Barking, Great Britain.

Archer et al., *Staphylococcus aureus* biofilms, Virluence, 2:1-15 (Sep./Oct. 2011), Landes Bioscience, Baltimore, MD.

NCBI submission YP_039527. Retrieved from the Internet Jan. 28, 2013: <http://www.ncbi.nlm.nih.gov/protein/YP_039527>.

Brady et al., Resolution of *Staphylococcus aureus* Biofilm Infection Using Vaccination and Antibiotic Treatment, Infection and Immunity, 4:1797-1803 (2011), American Society for Microbiology, Washington, D.C.

NCBI submission YP_040441. Retrieved from the Internet Jan. 28, 2013: <http://www.ncbi.nlm.nih.gov/protein/YP_040441>.

NCBI submission YP_373277. Retrieved from the Internet Jan. 28, 2013: <http://www.ncbi.nlm.nih.gov/protein/YP_373277>.

Database UniProt [Online], Apr. 3, 2007, "RecName: Full=Uncharacterized lipoprotein SAR0438; Flags: Precursor;" retrieved from EBI accession No. Q6GJN3.

Beenken et al., Global gene expression in *Staphylococcus aureus* biofilms, Journal of Bacteriology, 186:4665-4684 (2004).

Brady et al., Osteomyelitis: Clinical overview and mechanisms of infection persistence, Clinical Microbiology Newsletter, DOI: 10.1016/J.CLINMICNEWS.2006.04.001, 65-72, 2006, Elsevier, New York, NY.

Holden et al., Complete genomes of two clinical *Staphylococcus aureus* strains: Evidence for the rapid evolution of virulence and drug resistance, 2004, Proceedings of the National Academy of Sciences of the United States (PNAS), National Academy of Science, US.

Office Action from U.S. Appl. No. 12/671,398, mailed Apr. 2, 2012.
Office Action from U.S. Appl. No. 12/671,398, mailed Aug. 30, 2012.
Office Action from U.S. Appl. No. 12/671,398, mailed Jan. 3, 2013.

\* cited by examiner

IN VIVO BIOFILM INFECTION DIAGNOSIS AND TREATMENT

CROSS REFERENCE TO RELATED APPLICATIONS

This application is the U.S. National Stage Application under 35 U.S.C. 0371 of International Application No. PCT/US2009/055689, with an international filing, date of Sep. 2, 2009, which claims the benefit of U.S. Appl. No. 61/093,597, filed Sep. 2, 2008. The content of the aforesaid application is relied upon and incorporated by reference in its entirety.

FIELD OF THE INVENTION

The present invention relates to methods, compositions and kits for the diagnosis and treatment of biofilm infections, and more particularly, methods, compositions and kits wherein the diagnosis and treatment is performed in vivo.

REFERENCE TO A SEQUENCE LISTING SUBMITTED ELECTRONICALLY VIA EFS-WEB

The content of the sequence listing (Name: Sequence_Listing.txt, Size: 140,315 bytes; and Date of Creation: Feb. 25, 2011) electronically submitted via EFS-Web is incorporated by reference in its entirety.

BACKGROUND OF THE INVENTION

A biofilm infection is a type of infection caused by an aggregated community of microorganisms that adhere onto the surface of animate or inanimate objects. For example, native human tissue can serve as an animate surface whereas implanted medical devices can serve as inanimate surfaces. A biofilm can be mono- or polymicrobial and can be prokaryotic, eukaryotic, or both.

During the formation of a biofilm, bacterial cells that are free to move passively or actively through bodily fluids (i.e., planktonic bacteria), first attach to a surface (typically, damaged tissue or implanted medical devices), secrete a matrix of exopolymeric substance (EPS) that encase and protect the bacteria, and mature to form heterogeneous communities of microorganisms that are resistant to antibiotics and host defenses. The biofilm community is dynamic, and after maturation, clusters or individual cells detach and spread throughout the body (O'Toole et al., *Ann. Rev. Microbiol.*, 54, 49 (2000)).

The bacteria in a bio film tend to be more virulent and resistant to treatment than the same bacteria in the planktonic form. For example, methicillin-resistant *Staphylococcus aureus* biofilms are up to 1,000 times more resistant to vancomycin than when they are grown as a planktonic suspension (Jefferson et al., *Antimicrob Agents Chemother*, 49, 2467 (2005)). The heightened virulence and resistance to treatment is believed to be predominantly mediated by the EPS matrix. In addition, host immunity is compromised during biofilm infections because the immune system actively works to fight the infection but is incapable of resolving the infection (Leid et al., *Infect. Immun.*, 70, 6339 (2002); Jesaitis et al., *J. Immunol.*, 171, 4329 (2003); Leid et al., *J. Immunol.*, 175, 7512 (2005); Brady et al., *Infect. Immun.*, 74, 3415 (2006)).

The infected body part is typically an internal organ, such as a heart valve, vein, stomach, urinary tract, sinus, gum, bone, or joint. These infections will typically persist and often worsen over time with highly malignant results. These infections can range from subacute conditions, such as boils, kidney stones, middle-ear infections, and gingivitis, to more life-threatening illnesses, such as osteomyelitis, endocarditis, pneumonia, periodontal disease, urinary tract infections, medical device failure, and cystic fibrosis infections (Shirtliff et al., *Chem. Biol.*, 9, 859, (2002); Parsek and Singh, *Annu. Rev. Microbiol.*, 57, 677 (2003); Mack et al., *Int. J. Art Organs*, 29, 343 (2006); and Sanderson et al., *Laryngoscope*, 116, 1121 (2006)).

Biofilm infections are problematic in hospitals and contribute to the morbidity and mortality of immunocompromised patients. A significant number of biofilm infections are nocosomial, i.e., hospital-acquired. In particular, biofilm infections are often associated with indwelling medical devices, such as catheters, endrotracheal tubes, surgical sutures, hip and knee joint prostheses, and dental implants. Resolution is often achieved by invasive and often painful methods, such as debridement of the infected tissue or device.

Diagnosis of biofilm infections is currently accomplished by a variety of testing methods, none of which are specific for the biofilm mode of growth. For example, elevated white blood cell counts and C-reactive protein levels may indicate the presence of a biofilm infection since these are indicators of inflammation. However, these tests are incapable of determining the presence of a biofilm infection with a high level of assurance (Trampuz and Zimmerli, *Injury*, 37, S59 (2006)). Indeed, these tests lack the specificity required for discerning the presence of a biofilm infection versus a non-biofilm infection caused by any similar microorganism.

Culturing is another common method used in identifying microorganisms that may be involved in a biofilm infection, but contamination and long processing times are common problems. The inefficiency of traditional culturing methods to correctly identify microbes is exacerbated with biofilms. For example, biofilm microorganisms are difficult or impossible to culture on standard agar plates (Veeh et al., *J. Infect. Dis.*, 188, 519 (2003)). Even more, since biofilm organisms are inherently attached to a surface, they are not readily cultured by standard techniques which typically requires their transfer, and hence, detachment from the surface to which they are originally bound.

Serology-based assays are becoming more common since they address some of the problems associated with the culturing and imaging techniques. These in vitro assays can identify antibodies in sera that are active against one or more microorganisms that may be associated with a biofilm infection. The assays are typically conducted by testing serum with a test antigen believed to be indicative of the biofilm infection. Antibodies in the sera are typically tagged with a marker (e.g., fluorophore or nanoparticle) so that any antibodies that bind to the test antigen are readily observable on a substrate. However, at least one significant drawback of the assay technique is that determination of the presence of a microorganism does not necessarily indicate the active presence of a biofilm infection. A microorganism can be present in sera for several reasons other than due to a biofilm infection. For example, *S. aureus* is a highly ubiquitous pathogen which is often detected in serology-based assays as a false positive, because the antigen used is not indicative of the biofilm mode of growth. In addition, even if a serology-based assay can firmly establish the presence of a biofilm infection, this information is highly limited in that it generally does not provide information on the location or extent of the infection. Yet, knowing the location and extent of the biofilm infection is critical in determining a course of treatment.

Accordingly, there remains a need in the art for new, rapid, and inexpensive techniques to diagnose biofilm infections in patients. There is a particular need for in vivo diagnostic tests that can rapidly provide information on the precise location and severity of the infection. The diagnostic test would also preferably be easily incorporable into standard hospital equipment and procedures.

SUMMARY OF THE INVENTION

These and other objectives, as will be apparent to those having ordinary skill in the art, have been achieved by providing methods for the in vivo diagnosis and treatment of biofilm infections. The methods described herein possess the advantage of being non-invasive, non-toxic, and convenient to a subject in that the methods can generally be performed within routine time periods and make use of equipment typically already present in many hospital settings.

More specifically, in one aspect, the invention provides an in vivo method of detection of a biofilm infection residing in a mammal (i.e., patient) according to the following preferred practice, which includes: (i) administering to the mammal a diagnostic-effective amount of a biofilm-specific probe, wherein the probe comprises a biofilm-targeting moiety and a nanoparticle core, wherein the nanoparticle core comprises a paramagnetic material observable by a magnetic resonance diagnostic technique; and (ii) imaging the mammal using the magnetic resonance diagnostic technique after the biofilm-specific probe has been provided sufficient time to selectively bind to the biofilm infection, thereby detecting the presence of the biofilm infection in the mammal.

In another aspect, a method of treatment of the biofilm is preferably provided by incorporating a treatment step within the general diagnostic procedure described above, the treatment step preferably being performed by ablating the biofilm after the biofilm-specific probe is bound to the biofilm. Preferably, the ablation is performed by exposing either the biofilm-specific probe or a secondary probe attached to the biofilm-specific probe to thermal-inducing radiation (e.g., magnetic resonance (i.e., radio frequency) or infrared radiation), wherein the biofilm-specific probe and/or secondary probe release heat to surrounding tissue when exposed to the thermal-inducing radiation.

The invention advantageously provides convenient, accurate, and safe methods for the in vivo diagnosis and treatment of biofilm infections. As biofilm infections pose a major health hazard, the methods described herein are highly beneficial in that numerous associated diseases and malevolent conditions due to biofilm infections can be prevented before irreversible damage occurs. This, in turn, can prevent pain, suffering, and even deaths caused by biofilm infections. Furthermore, the methods disclosed herein can advantageously eliminate the need for surgery (e.g., open surgery, amputation, or debridement), or even antibiotics, while effectively removing a biofilm infection.

In another aspect, the invention encompasses compositions useful for detecting and/or treating biofilm infections. The compositions comprise one or more components that are useful in carrying out the methods of the present invention as described herein.

In another aspect, the invention encompasses kits useful for detecting and/or treating biofilm infections. The kits comprise one or more components that are useful in carrying out the methods of the present invention as described herein.

DETAILED DESCRIPTION OF THE INVENTION

Figure 1:
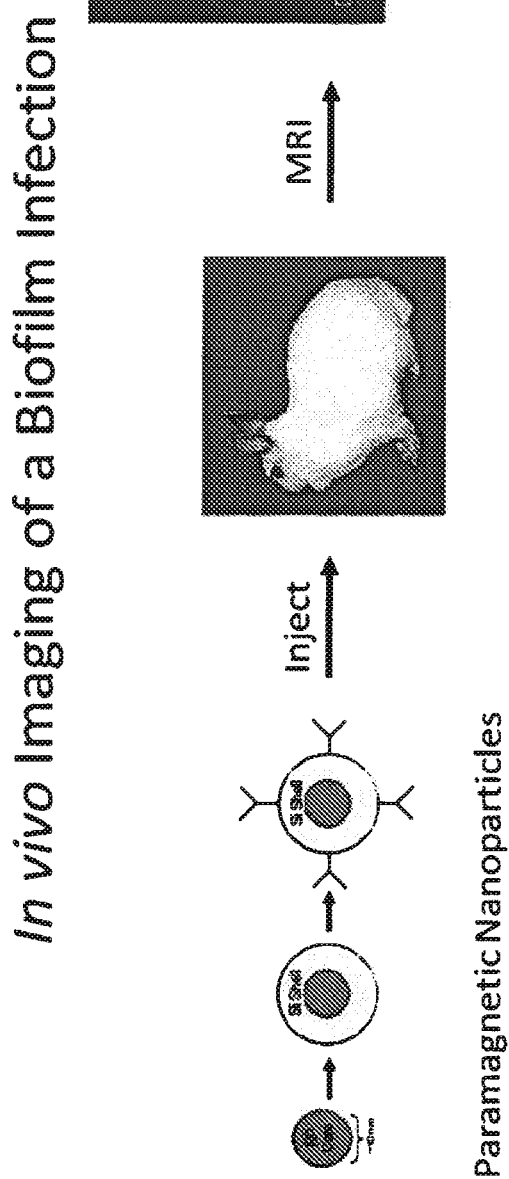
FIG. 1 General schematic showing a preferred embodiment of the invention for the in vivo imaging of a biofilm infection.

In a first aspect, the invention is directed to a method for the in vivo detection of a bio film infection residing in a mammal. The mammal can be any mammal (e.g., a cat, dog, horse, or ape), but the method is more typically directed to human subjects. A general schematic of the process is depicted in FIG. 1 for a biofilm-infected rabbit. As shown, selective targeting of the biofilm-specific probes of the invention renders a bio film observable by MRI and distinguishable from non-biofilm containing tissue; i.e., the MRI scan shown on the left slide of FIG. 1 for rabbit bone containing a biofilm is noticeably brighter than the MRI scan shown on the right, which corresponds to a rabbit bone not containing a bio film. In one embodiment, the invention is directed to a method for in vivo detection of a biofilm infection residing in a mammal, the method comprising: (i) administering to the mammal a diagnostic-effective amount of a biofilm-specific probe, wherein the probe comprises a biofilm-targeting moiety and a nanoparticle core, wherein the nanoparticle core comprises a paramagnetic material observable by a magnetic resonance diagnostic technique; and (ii) imaging the mammal using a magnetic resonance diagnostic technique after said biofilm-specific probe has been provided sufficient time to selectively bind to the biofilm infection, thereby detecting the presence of the biofilm infection in the mammal. The biofilm infection can be located on any part of the body and can be caused by any one or combination of microorganisms. Some examples of body parts that may contain a biofilm include the heart, stomach, intestines, a vein or artery, sinus, gums, bone, joint, kidney, jaw, liver, and bladder. The biofilm infection may also be located on medical devices, including, but not limited to catheters, orthopedic devices, implants, prosthetic heart valves, prosthetic joints, orthopedic implants, shunts, pacemaker and defibrillator, endrotracheal intubation, hemodialysis/peritoneal dialysis devices, dental implants, intravascular catheters, intrauterine devices (IUDs), and any inert and chemically modified plastic used for implant or medical device purposes. The microorganism can be any type, including procaryote or eucaryote, e.g., bacteria, archaea, protozoa, fungi (e.g., yeast (such as *Candida albicans*) or mold), and algae.

More typically, the microorganism is one or more types of bacteria. The bacteria can be gram positive or gram negative. Some examples of genera of biofilm-causing bacteria include *Staphylococcus*, Coliforms (e.g., *Citrobacter, Enterobacter, Escherichia, Hafnia, Klebsiella, Serratia* and *Yersinia*), Lactic Acid Bacteria (e.g., *Enterococcus, Streptococcus*), *Pseudomonas*, and *Aspergillus*.

In some embodiments, the present invention is particularly directed to methods of detecting and/or treating biofilm infections caused by *Staphylococcus* bacteria. Some examples of particularly relevant species of *Staphylococcus* include *Staphylococcus aureus, Staphylococcus epidermidis, Staphylococcus haemolyticus, Staphylococcus saprophyticus, Staphylococcus hominis, Staphylococcus warneri, Staphylococcus cohnii, Staphylococcus capitis, Staphylococcus camosis, Staphylococcus lugdunesis, Staphylococcus schleiferi,* and *Staphylococcus caprae.*

The invention also considers any antibiotic-resistant microorganism, particularly antibiotic-resistant bacteria. Of particular importance is the class of antibiotic-resistant *Staphylococcus* bacteria. Most notable of the antibiotic-resistant bacteria are the methicillin-resistant *Staphylococcus aureus* (MRSA) and methicillin-susceptible *Staphylococcus aureus* (MSSA) types of bacteria.

Other species of bacteria that can be involved in biofilm infections include, for example, *Escherichia coli, Yersinia pestis, Pseudomonas aeruginosa, Streptococcus mutans, Streptococcus sanguinis, Enterococcus faecalis, Streptococcus viridans, Klebsiella pneumoniae, Proteus mirabilis* and *Streptococcus veridans*.

The diagnostic and treatment methods used herein are performed in vivo. By being "in vivo," the diagnostic and treatment methods described herein are conducted directly in the body of the subject. This is to be contrasted with "in vitro" methods which are conducted in a controlled environment outside of the body of the subject, e.g., in a Petri dish, test well, microtiter plate, test tube, sample pad, test strip, or the like.

The diagnostic method involves administration to the subject of a diagnostic-effective amount of a biofilm-specific probe in order for the probe to bind to the bio film infection and make the biofilm infection observable by use of a magnetic resonance diagnostic technique (most notably, magnetic resonance imaging (MRI)). By being a "biofilm-specific" probe, the probe is made to specifically (i.e., selectively) bind to (i.e., target) a biofilm infection while preferably exhibiting a clear absence of any binding to non-biofilm material. In other words, the probe preferably exhibits an absence of non-specific binding so that the biofilm infection can selectively be made more observable by use of a magnetic resonance diagnostic technique such as MRI. The biofilm-specific probe can bind to the biofilm infection either directly or indirectly, for example, by using a first probe that binds directly to the bio film and a secondary probe that binds to the first probe.

The bio film-specific probe makes the bio film infection more observable during magnetic resonance imaging by including a nanoparticle core constructed, at least in part, of a paramagnetic material. By being paramagnetic, the nanoparticle core functions as a contrast agent, and hence, its presence, as well as the presence of any bio film that may be present, is observable by imaging the subject using a magnetic resonance diagnostic technique. More specifically, the nanoparticle is capable of functioning as a magnetic resonance imaging (MRI) contrast agent by altering the relaxation rates of surrounding water molecules.

The nanoparticle core is constructed, at least in part, of any paramagnetic material capable of being observed by use of a magnetic resonance diagnostic technique such as MRI. As used herein, "paramagnetic material" refers to a material which possesses a magnetic moment that can be influenced by an external magnetic field. Typically, the nanoparticles composed of a paramagnetic material exhibit a superparamagnetic property, i.e., the nanoparticle as a whole possesses a magnetic moment which tends to align with an external magnetic field (as opposed to magnetic moments of individual atoms aligning with an external magnetic field). Accordingly, as used herein, the term "paramagnetic material" is meant to include any material which possesses a magnet moment that can be aligned by an external magnetic field. Thus, as used herein, a paramagnetic material includes a superparamagnetic material.

Preferably, the nanoparticle cores are constructed of a metal-containing material which is paramagnetic. Some examples of such materials include chromium, manganese, iron, cobalt, nickel, and copper base metals, and their alloys among themselves or with other metals. More typically, the metal is in an oxidized state and combined with one or more main group elements, such as the oxides and sulfides of these metals. The metallic nanoparticle can also be in the form of, for example, metal salts that do not dissolve inside the body, and thus, hold their form as nanoparticles after entry into the body. The nanoparticle cores can optionally contain one or more rare earth metals (e.g., gadolinium or dysprosium) known to function as MRI contrast agents. Since the nanoparticles are administered into the subject, the nanoparticles are preferably constructed of materials that are of low toxicity, and more preferably, non-toxic.

More preferably, the nanoparticle cores are composed of iron oxide. The iron oxide can be any suitable form of iron oxide, but is more typically iron (III) oxide ($Fe_2O_3$) of any suitable form, including the alpha- (i.e., hematite), beta-, gamma- (i.e., maghemite), and epsilon-forms of $Fe_2O_3$. The iron oxide can also contain iron (II), as in FeO, or a mixture of iron (II) and iron (III), as in $Fe_3O_4$ (magnetite). The iron oxide can also be an iron oxide-hydroxide composition and can include other atom types, including, for example, chloro groups, other paramagnetic metals, or alkali or alkaline earth metals. The iron oxide (or other metal oxide) can also be in the form of a spinel composition, e.g., $MFe_2O_4$, wherein M is a divalent metal ion. The iron oxide (or other metal oxide) can also be in the form of a perovskite composition, e.g., $MFeO_3$, wherein M is typically a trivalent metal ion, such as a trivalent lanthanide metal (e.g., La).

The nanoparticle is typically spheroidal in shape, but numerous other shapes are suitable. Some other shapes of nanoparticles include ovoid, cuboidal, polygonal (i.e., faceted), tubular, disc, prism, and the like. As used herein, the "diameter of the nanoparticle" refers to the longest dimension of the nanoparticle and refers only to the portion of the nanoparticle containing atoms imparting a paramagnetic property to the nanoparticle. Accordingly, the "diameter of the nanoparticle" as used herein does not include coatings or molecular groups attached or associated with the surface of the nanoparticle. The volume encompassed by the atoms imparting a paramagnetic property is also referred to herein as the "nanoparticle core."

The nanoparticle core preferably has a diameter of at least about 1 nanometer (nm) and up to about 300 nm. More preferably, the diameter of the nanoparticle core is no more than about 100 nm, more preferably no more than about 50 nm, more preferably no more than about 30 nm, and even more preferably no more than about 20 nm. In other embodiments, the nanoparticle core has a diameter of at least about 2 nm, 3 nm, 4 nm, 5 nm, or 10 nm, and any of the maximum diameters described above. For example, in different embodiments, the nanoparticle core can have a diameter of about 3 to about 30 nm, or about 3 to about 20 nm, or about 3 to about 10 nm, or about 4 to about 10 nm, or about 6 to about 12 nm, or about 10 to about 30 nm, or about 10 to about 20 nm.

The nanoparticle cores used herein can range in size variation. As noted above, the cores preferably have a diameter of at least about 1 nanometer (nm) and up to about 300 nm. For example, the nanoparticle cores can be approximately monodisperse, and thus, essentially unvaried in size. Alternatively, the nanoparticle cores can be polydisperse to any suitable degree.

The nanoparticles can be synthesized according to any of the procedures well-known in the art. For example, zerovalent metal nanoparticles can be fabricated by chemical reduction, sonication, or chemical vapor deposition (CVD) of precursor metal salts. Metal oxide nanoparticles can be produced by similar means, and also by attrition (e.g., ball milling and other size-reducing methods) and pyrolysis.

The nanoparticles can be functionalized in any suitable manner according to methods well-known in the art. For example, the nanoparticles, such as iron, cobalt, nickel, or copper nanoparticles, or their oxide or sulfide forms, can be functionalized with molecules bearing functional groups that interact well with metals. Some examples of such groups include phosphine and mercapto groups. The molecules coating the surface can also include any appropriate end-functional group (e.g., amino, carboxy, hydroxy, or aldehyde groups). Alternatively, the nanoparticle can be coated with a noble metal (e.g., gold) or other metal, and the coating metal coated with similar molecules as above in order to provide functionalization to the nanoparticle. Still yet, the nanoparticle can be coated with a polymeric material, such as a dextran, cellulosic material, polyethylene oxide (PEO), or albumin.

In another embodiment, according to methods known in the art, the nanoparticle can be coated with a polymeric substance containing functional groups. For example, the nanoparticles can be coated with carboxymethyl dextran to provide carboxy-functionality to the nanoparticles. Alternatively, carboxy-functionality can be provided to the nanoparticles by coating the nanoparticles with a polysaccharide and reacting the coating with a haloacetic acid under suitable conditions. The carboxy functional groups can then be used as precursors to form other groups, such as, for example, amino groups, by reacting the carboxy groups with, for example, a carbodiimide and diamine molecule. The carboxy groups can also be converted to aldehyde groups by appropriate chemical reduction. Alternatively, dextran-coated nanoparticles can be reacted with epichlorohydrin, resulting in a nanoparticle functionalized with epoxy groups. The epoxy group can, in turn, be converted to another group, such as by reaction with ammonia or an organoamine to produce an amine.

In order for the nanoparticle core to bind specifically to a bio film infection (and hence, function as part of a biofilm-specific probe), the nanoparticle core is conjugated to a biofilm-targeting moiety. The biofilm-targeting moiety can be any compound or material that selectively targets (i.e., locates and binds to) a biofilm infection. In some embodiments, the biofilm-targeting moiety binds directly to the biofilm infection. In some embodiments, multiple probes are used to target the biofilm infection, and one or more of the probes binds indirectly to the biofilm infection. For example, a first biofilm-specific probe having a biofilm-targeting moiety is administered that binds to a biofilm infection, followed by administration of a second probe having a biofilm-targeting moiety that binds to the first bio film-specific probe. In some embodiments, the biofilm-targeting moiety preferentially targets microbially-derived components within a biofilm, whether the components are part of the biofilm matrix or associated with the microbial cells within or on the biofilm. In some embodiments, the biofilm-targeting moiety most commonly targets one or more microorganisms involved in the biofilm infection. However, in some embodiments, the biofilm-targeting moiety can be made to target any chemical, biological tissue, or other material emanating from or resulting from a biofilm infection and in close proximity to the biofilm infection, wherein binding to such a material also serves to selectively target a biofilm infection and make the biofilm infection observable during observation with a magnetic resonance diagnostic technique.

In some embodiments, the biofilm-targeting moiety is typically a biological material that can selectively target a biofilm infection. Some examples of biofilm-binding biological materials include proteins, glycoproteins (e.g., antibodies), peptides, polypeptides, peptide conjugates, ligands, polysaccharides, polynucleotides, nucleic acids, glycolipids, and lipoproteins.

In some embodiments, the biofilm-targeting moiety is an antibody that targets an antigen of a biofilm infection. The antibody can be raised against a particular biofilm antigen according to any of the methods known in the art. For example, the antibodies can be raised in polyclonal form by methods known in the art, or alternatively, in monoclonal form using, for example, known hybridoma technology. The antibodies can be raised in any suitable mammal, including, for example, rabbits, guinea pigs, rats, mice, horses, sheep, goats, and primates. More typically, the antibodies are derived from mice. In some embodiments, antibodies thus obtained are humanized by methods known in the art for the purpose of human clinical use. The antibody is typically of the IgG class, but can be of any of the other classes, including IgM, IgA, IgD or IgE. The antibody can also be of any subclass, e.g., the $IgG_1$, $IgG_2$, $IgG_3$, and $IgG_4$ subclasses, but is more typically of the $IgG_1$ subclass.

In some embodiments, the biofilm-targeting moiety is a secondary antibody that binds to a first antibody that targets the biofilm. Examples of secondary antibodies include, for example, goat anti-rabbit, goat anti-mouse, sheep anti-mouse, sheep anti-rabbit, rabbit anti-mouse, and rabbit anti-sheep. The antibody can be of any class including IgG, IgM, IgA, IgD or IgE. The antibody can also be of any subclass.

The antibody can also be an antibody fragment that contains at least a portion of hypervariable ($F_v$) region of a biofilm-targeting antibody. Preferably, the antibody fragment has binding characteristics that are the same as, or comparable to, those of the whole antibody. Some examples of suitable antibody fragments include any fragment that comprises a sufficient portion of the hypervariable region to bind specifically, and with sufficient affinity, to a biofilm antigen. Such fragments can be, for example, a Fab or (Fab')$_2$ fragment. These fragments can be derived from the whole antibody by techniques well-known in the art, such as, for example, by use of enzymatic cleavage (e.g., papain or pepsin at hinge locations) followed by chemical reduction. Preferably, the antibody fragments contain all six complementarity determining regions (CDRs) of the whole antibody, although functional fragments containing fewer than all of such regions, such as three, four or five CDRs, may also be suitable.

In a particular embodiment, the antibody is generated by an immunological response to a recombinant biofilm-specific protein. The generated antibodies are then harvested by conventional immunological methods known in the art. Preferably, the recombinant biofilm-specific protein is an *Escherichia coli* expressing MRSA biofilm protein which is a ligand for other identified biofilm-specific proteins. Some preferred recombinant biofilm-specific proteins include, for example, lipase (Ag01, Accession No. 28195801) (SEQ ID NO:4), hypothetical protein 0486 (Ag02, Accession No. YP_039889) (SEQ ID NO:1), or lipoprotein ABC transporter protein (Ag03, Accession No. 15923621) (SEQ ID NO:13), hypothetical protein SAR0056 (SEQ ID NO:2), glucosaminidase; bifunctional autolysin precursor (SEQ ID NO:3), SA0037 (conserved hypothetical protein; SEQ ID NO:43), or antigenic fragments thereof. Those of skill in the art understand that antibodies can be characterized by their ability to specifically and/or selectively bind to one or more epitopes on a target protein, and methods for "epitope mapping" are well known in the art. An epitope as described herein may comprise amino acid residues directly involved in the binding of the antibody (the immunodominant component of the epitope) and other amino acid residues, which are not directly involved in the binding, such as amino acid residues that are effectively blocked by the bound antibody. As is also well known in the art, bacterial proteins mutate over time, and thus, it is possible that, within a population of S. aureus isolates, the proteins would vary by one or a few amino acid substitutions, insertions, deletions, etc., while maintaining one or more epitopes for the antibody of interest.

In accordance with the present invention, antibodies can be directed against any other antigens which can serve as a marker of biofilm-specific infection. Non-limiting examples of other antigens which could be used as biofilm-specific markers are listed in the attached sequence listing (SEQ ID NOS:5-12 and 14-42). Nucleic acid primers useful for amplifying nucleic acid sequences encoding SEQ ID NO:1 are SEQ ID NOS: 52-53; for amplifying nucleic acid sequences encoding SEQ ID NO:3 are SEQ ID NOS:50-51; for amplifying nucleic acid sequences encoding SEQ ID NO:4 are SEQ ID NOS:46-47; for amplifying nucleic acid sequences encoding SEQ ID NO:13 are SEQ ID NOS:48-49; and for amplifying nucleic acid sequences encoding SEQ ID NO:43 are SEQ ID NOS:44-45.

In some embodiments, the biofilm-targeting moiety is a peptide or receptor-specific ligand. A receptor-specific ligand is a natural or synthetic molecule, such as a hormone or neurotransmitter, which specifically binds to a receptor on the surface of a cell.

In some embodiments, the biofilm-targeting moiety of the probe is conjugated to the nanoparticle by any suitable means which retains the selective targeting ability of the biofilm-targeting moiety. By being "conjugated" to the nanoparticle, the biofilm-targeting moiety is attached to the nanoparticle in a manner that retains the attachment from initial administration to binding of the probe to the biofilm, including both covalent and non-covalent means, as described below. The biofilm-targeting moiety preferably remains attached to the nanoparticle core permanently, i.e., at least long enough for the probe to remain intact when binding to the biofilm infection and for a typical magnetic resonance diagnostic test to be conducted.

The biofilm-targeting moiety is typically bound to the nanoparticle core by one or more covalent bonds. However, the biofilm-targeting moiety can be attached to the nanoparticle core by bonding modes that are non-covalent and which can, depending on the degree of interaction and number of such bonds, retain a permanent attachment of the biofilm-targeting moiety and nanoparticle core. Some examples of other suitable bonding modes include ionic bonding, hydrogen bonding, metal-coordination, and dative bonding.

The biofilm-targeting moiety can be bound directly to the nanoparticle core. For example, it is possible to directly bind the nanoparticle core to a peptide or antibody by reaction of a functional group on the peptide or antibody with a leaving group (or activated leaving group) on the surface of the nanoparticle core. The binding can be covalent or non-covalent in nature. For example, metal oxide nanoparticles typically contain surface hydroxy groups which can be made to directly react and link with a group of the biofilm-targeting moiety by appropriate activation of either the surface hydroxy group or the group on the biofilm-targeting moiety.

However, more typically, the biofilm-targeting moiety is bound indirectly to the nanoparticle core via one or more linking molecules or materials (i.e., linkers or crosslinkers).

The linker can be any suitable molecular moiety or material capable of keeping the biofilm-targeting moiety bound to the nanoparticle core. The linker can be, for example, a suitable biological or synthetic molecule or material.

Some examples of biological molecules that can function as linkers include peptides, amino acids, monosaccharides, oligosaccharides, cofactors, nucleic acids, and small biological compounds (e.g., biotin). Some examples of biological materials that can function as linkers include proteins and glycoproteins (e.g., protein A, antibodies, albumin, and enzymes), polysaccharides, nucleic acids, lipids, glycolipids, lipoproteins, and the like.

Some examples of synthetic linkers include siloxanes (i.e., "chemically functionalized silica"), polysiloxanes, polyethylene glycol (PEG), polyvinyl alcohol (PVA), polyvinyl acetate (PVAc), the polyacrylates and polymethacrylates, fluoropolymers, liposomes, dendrimers, the dextrans, cellulosic materials, and the like. The foregoing types of synthetic linkers can be considered to function as polymeric coatings on the nanoparticle. In some embodiments, the polymeric coating serves primarily to function, not as a linker, but to properly disperse the nanoparticles and prevent them from agglomerating and/or provide the nanoparticles with proper solubility. In such a case, a separate functional material can be included within, or attached to, the coating to provide crosslinking capability.

In a preferred embodiment, the synthetic linkers are difunctional organic molecules, of which the siloxanes can be considered an example. By being "difunctional," the linker contains two functional groups: one for binding to the nanoparticle core or a coating thereon, and another for binding to the biofilm-targeting moiety.

The surface of iron oxide and other metal oxide nanoparticles are known to possess hydroxyl groups. Accordingly, when using iron oxide nanoparticles, any difunctional linker capable of reacting with the surface hydroxyl groups to form a bond, and which also possess a suitable functional group for binding to the biofilm-targeting moiety, are suitable according to the present invention. For example, the hydroxy groups on the surface of iron oxide nanoparticles can be rendered amine-reactive by reacting the nanoparticles with a bifunctional molecule having a hydroxy-reactive group (e.g., isocyanate group) on one end and an amino-reactive group (e.g., succinimidyl ester group) on the other end. The isocyanate group reacts with a surface hydroxy group to form a carbamate linkage and the succinimidyl ester group can react with and bind to an amino group of an amino-containing biofilm-targeting moiety. The surface hydroxy groups can alternatively be rendered thiol-reactive by reacting the nanoparticles with a bifunctional molecule having a hydroxy-reactive group (e.g., isocyanate group) on one end and a thiol-reactive group (e.g., maleimido group) on the other end. An example of the latter type of bifunctional molecule includes N-(p-maleimidophenyl)isocyanate (PMPI), which is commercially available (e.g., from Pierce). The thiol-reactive group can react with and bind to a thiol group of a thiol-containing biofilm-targeting moiety.

In a preferred embodiment, iron oxide nanoparticle cores are functionalized by reacting with one or more types of siloxane molecules, each possessing one or more alkoxy or hydroxy groups bound to at least one silicon atom via a silyl-oxygen bond. As known in the art, the silyl-alkoxy or silyl-hydroxy groups have a propensity for reacting with surface metal-hydroxyl groups by a condensation reaction wherein the siloxane becomes bound to the surface of the particle by a silyl-oxygen-surface bonding scheme. Silyl-oxygen-surface bonds can also be realized by reacting chlorosilanes with the metal oxide surface. Typically, the siloxanes form a self-assembled monolayer (SAM) on the surface of the particle wherein a silyl-oxygen-silyl network of bonds is formed between adjacent siloxane molecules.

At least one, and preferably, several (i.e., a portion), of the siloxane molecules residing on a paramagnetic metal oxide surface are end-functionalized (i.e., containing functional groups opposite from the particle surface) such that end-functional groups are capable of binding to the biofilm-targeting moiety. As used herein, the term "functional group" refers to groups that are capable of reacting with, and creating an attachment to, a biofilm-targeting agent, either directly or by binding through a secondary linker (i.e., coupling molecule). Accordingly, a "functional group," as used herein, can also be referred to as a "reactive group." Generally, functional (i.e., reactive) groups include, for example, amino, thiol, epoxy, alkyl halide, isocyanate, hydrazide, semicarbazide, azide, ester, carboxylic acid, aldehyde, ketone, vinyl, disulfide, and maleimide groups. Non-functional (i.e., non-reactive) groups typically include, for example, saturated hydrocarbon, polyalkylene oxide or glycol (e.g., polyethylene glycol), linking amide, and carbon-bound hydroxyl groups. However, it is to be understood that under appropriate conditions a group generally considered to be non-reactive can be made to be reactive and that a group generally considered to be reactive can be rendered non-reactive or less reactive than other groups also present.

Preferably, the end-functional group binds covalently, either directly or through a secondary linker, to the biofilm-targeting moiety. In some embodiments, the end-functional group is capable of binding to the biofilm-targeting moiety without being activated in some manner, whereas in other embodiments the end-functional group is activated in order to bind to the biofilm-targeting moiety.

Siloxane molecules can be made to bind to the surface of a metal oxide nanoparticle by any of the means known in the art to produce functionalized metal oxide nanoparticles suitable for ingestion by a subject. Typically, the siloxane molecules are added to an aqueous dispersion of the metal oxide nanoparticles. A catalytic amount of an acid is typically added to bring the reaction to completion. The functionalized metal oxide nanoparticles can be isolated by any suitable method known in the art, including, for example, precipitation, filtration, or adsorption.

In a first embodiment, a siloxane molecule containing one or more amino groups as an end-functional group is made to bind to the surface of a MRI-imageable metal oxide nanoparticle. After binding, the amino-functionalized siloxane molecule contains an amino group directed away from the nanoparticle surface such that it is available to react and bind with the biofilm-targeting moiety. Some examples of siloxane molecules that contain amino end-functional groups include 3-aminopropyltrimethoxysilane (CAS 13822-56-5), 3-aminopropyltriethoxysilane (CAS 919-30-2), aminopropylsilanetriol (29159-37-3), 3-aminopropylmethyldiethoxysilane (CAS 3179-76-8), 3-aminopropyl-dimethylethoxysilane (CAS 18306-79-1), 3-aminopropyldiisopropylethoxysilane (CAS 17559-36-1), p-aminophenyltrimethoxysilane (CAS 33976-43-1), ureidopropyl-trimethoxysilane (CAS 23843-64-3), ureidopropyltriethoxysilane (CAS 23779-32-0), 3-trimethoxysilylpropyldiethylenetriamine (CAS 35141-30-1), N-(6-aminohexyl)-aminopropyltrimethoxysilane (CAS 51895-58-0), N-(2-aminoethyl)-3-aminopropyl-trimethoxysilane (CAS 1760-24-3), N-(2-aminoethyl)-3-aminopropylmethyl-dimethoxysilane (CAS 3069-29-2), (aminoethylaminomethyl)phenethyl-trimethoxysilane (CAS 74113-77-2), N-(2-aminoethyl)-3-aminoisobutylmethyldimethoxysilane (CAS 23410-40-4), 4-aminobutyltriethoxysilane (CAS 3069-30-5), 6-aminohexyltrimethoxysilane, 8-aminooctyltrimethoxysilane, and the like. The majority of the above siloxanes are commercially available (e.g., from Gelest).

The amino group of the surface-bound siloxane molecule can be made to bind to a biofilm-targeting moiety by any suitable means. For example, the siloxane amino group can be made to bind, via a suitable secondary crosslinker (i.e., coupler), with amino groups in an amino-containing biofilm-targeting moiety (e.g., a proteinaceous moiety, such as an antibody or oligopeptide). Some examples of suitable amino-amino coupling reagents include disuccinimidyl suberate (DSS), disuccinimidyl tartrate (DST), disulfosuccinimidyl tartrate (sulfo-DST), dimethyl 3,3'-dithiobispropionimidate.2HCl (DTBP), 3,3'-dithiobis(sulfo-succinimidyl propionate) (DTSSP), ethylene glycol bis(succinimidylsuccinate) (EGS), ethylene glycol bis(sulfo succinimidylsuccinate) (sulfo-EGS), bis(sulfosuccinimidyl) suberate ($BS^3$), disuccinimidyl glutarate (DSG), dimethyl adipimidate.2HCl (DMA), dimethyl pimelimidate.2HCl (DMP), dimethyl suberimidate.2HCl (DMS), bis-[2-(succinimidyloxycarbonyloxy)-ethyl]sulfone (BSOCOES), tris-succinimidyl aminotriacetate (TSAT), and the like, and derivatives derived therefrom. The above crosslinkers are commercially available (e.g., from Pierce).

Alternatively, the amino group of the surface-bound siloxane molecule can be made to bind, via a suitable coupler, with thiol (mercapto) groups in a thiol-containing bio film-targeting moiety. Typically, the thiol-containing bio film-targeting moiety is an antibody fragment which has been cleaved in the $F_c$ region (e.g., at the hinge region), by methods well-known in the art, to result in a Fab or (Fab')$_2$ fragment containing free thiol groups opposite to the variable ($F_v$) region. Some examples of suitable amino-thiol coupling reagents include succinimidyl 4-(N-maleimidomethyl)-cyclohexane-1-carboxylate (SMCC), sulfosuccinimidyl 4-(N-maleimidomethyl)-cyclohexane-1-carboxylate (sulfo-SMCC), N-α-maleimidoacetoxy)succinimide ester (AMAS), N-β-maleimidopropionic acid (BMPA) when used in combination with EDC, N-ε-maleimidocaproic acid (EMCA) when used in combination with EDC, N[β-maleimidopropyloxy]succinimide ester (BMPS), N-(ε-maleimidocaproyloxy)succinimide ester (EMCS), succinimidyl 6-(3-(2-pyridyldithio)-propionamido)hexanoate (LC-SPDP), m-maleimidobenzoyl-N-hydroxysuccinimide ester (MBS), N-succinimidyl(4-iodoacetyl)aminobenzoate (SIAB), succinimidyl 4-(p-maleimidophenyl)butyrate (SMPB), sulfosuccinimidyl 4-(p-maleimidophenyl)butyrate (sulfo-SMPB), and succinimidyl-6-[(β-maleimidopropionamido)-hexanoate] (SMPH). The above crosslinkers are commercially available (e.g., from Pierce).

The above list of amino-amino and amino-thiol coupling agents are by no means meant to be inclusive, but rather, exemplary. Numerous other coupling agents with similar or completely different chemical structures are suitable. For example, some other classes of amino-amino coupling agents include the diisocyanates, alkyl dihalides, dialdehydes, activated esters, and still numerous others.

In a second embodiment, a siloxane molecule containing one or more carboxy groups as an end-functional group is made to bind to the surface of a MRI-imageable metal oxide nanoparticle. After binding, the carboxy-functionalized siloxane molecule contains a carboxy group directed away from the nanoparticle surface such that it is available to react and bind with the biofilm-targeting moiety. Some examples of siloxane molecules that contain carboxy end-functional groups include 2-(trimethoxysilyl)acetic acid, 3-(trimethoxylsilyl)propionic acid, 4-(trimethoxysilyl)butyric acid, 5-(trimethoxysilyl)valeric acid, 6-(trimethoxysilyl)caproic acid, and their esters, and their alkali or ammonium salts. Alternatively, an amino- or hydroxy-end-capped siloxane molecule can be reacted with a chemical that can convert the end-amino or end-hydroxy group to a carboxy or ester group. For example, an amino-functionalized siloxane group can be converted to a carboxy-functionalized siloxane group by reaction of the amino group with methyl N-succinimidyl adipate (MSA), which is commercially available (e.g., from Pierce). The resulting carboxy group can be additionally reacted in order to link with the biofilm-targeting moiety, or alternatively, the carboxy group can serve a different purpose, such as, for example, use as a chelating agent to a metal contrast agent, or left in its unreacted form or in salt form in order to modify the water solubility of the probe.

The carboxy group of the surface-bound siloxane molecule can be made to bind to a biofilm-targeting moiety by any suitable means. For example, the siloxane carboxy group can be made to bind, via a suitable secondary crosslinker, with amino groups present in an amino-containing biofilm-targeting moiety (e.g., a proteinaceous moiety, such as an antibody or oligopeptide) by an amide bond, or with hydroxy groups in a hydroxy-containing biofilm-targeting moiety (e.g., a proteinaceous moiety or saccharide group) by an ester bond. Some examples of suitable coupling reagents for coupling carboxy groups with amino or hydroxy groups include the carbodiimide class of couplers, which includes, for example, N-hydroxysuccimide (NHS), N-sulfohydroxysuccimide (sulfo-NHS), carbonyl diimidazole (CDI), N,N'-dicyclohexylcarbodiimide (DCC), N,N'-diisopropylcarbodiimide (DIC), 1-ethyl-3-(3-dimethylaminopropyl)carbodiimide hydrochloride (EDC), hydroxybenzotriazole (HOBt), and pentafluorophenol. EDC and DCC are often used in combination with NHS or sulfo-NHS. Most of the coupling reagents described above are commercially available.

In a third embodiment, a siloxane molecule containing one or more thiol groups as an end-functional group is made to bind to the surface of a MRI-imageable metal oxide nanoparticle. After binding, the thiol-functionalized siloxane molecule contains a thiol group directed away from the nanoparticle surface such that it is available to react and bind with the biofilm-targeting moiety. Some examples of siloxane molecules that contain thiol end-functional groups include 3-mercaptopropyltrimethoxysilane (CAS 84682-36-0), 3-mercaptopropyltriethoxysilane (CAS 4420-74-0), 3-mercaptopropylmethyldimethoxysilane (CAS 31001-77-1), mercaptomethyl(methyl)diethoxysilane, 4-mercaptobutyltrimethoxysilane, 5-mercaptopentyltrimethoxysilane, 6-mercaptohexyltrimethoxysilane, and 8-mercaptooctyltrimethoxysilane. Several of the thiol-functionalized siloxanes mentioned above are commercially available (e.g., from Gelest).

The thiol group of the surface-bound siloxane molecule can be made to bind to a biofilm-targeting moiety by any suitable means. For example, the siloxane thiol group can be made to bind to an amino group of an amino-containing biofilm-targeting moiety by use of an amino-thiol coupling reagent, such as any of the amino-thiol coupling reagents already described above for use with amino-functionalized siloxane molecules being coupled to thiol-containing biofilm-targeting moieties.

The thiol-functionalized siloxane molecule can also be made to bind to a thiol group of a thiol-containing biofilm-targeting moiety by use of a thiol-thiol coupling reagent. Some examples of suitable thiol-thiol coupling reagents include 1,4-bis-maleimidobutane (BMB), 1,4-bis-maleimidyl-2,3-dihydroxybutane (BMDB), bis-maleimidohexane (BMH), bis-maleimidoethane (BMOE),1,8-bis-maleimidotriethyleneglycol (BM(PEO)$_3$), 1,11-bis-maleimidotetraethyleneglycol (BM(PEO)$_4$), 1,4-di-(3'-(2'-pyridyldithio)propionamido)butane (DPDPB), dithio-bis-maleimidoethane (DTME),1,6-hexane-bis-vinylsulfone (HBVS), and tris-(2-maleimidoethyl)amine (TMEA). The above crosslinkers are commercially available (e.g., from Pierce).

The above list of thiol-amino and thiol-thiol coupling agents are by no means meant to be inclusive, but rather, exemplary. Numerous other such coupling agents with similar or completely different chemical structures are suitable.

The coupling agents, such as the ones described above, can be reacted with the nanoparticle and biofilm-targeting moiety in any suitable manner that results in the biofilm-targeting moiety being attached, via the coupling agent and any linker, to the nanoparticle. For example, by methods known in the art, functionalized nanoparticles can be reacted with one end of a coupling agent, and then the nanoparticle-coupling agent combination reacted with the biofilm-targeting moiety. Alternatively, by methods known in the art, the biofilm-targeting moiety can be reacted with one end of a coupling agent, and then the (biofilm-targeting moiety)-(coupling agent) combination reacted with the functionalized nanoparticle. Other methods of coupling the biofilm-targeting moiety and nanoparticle are possible and contemplated herein.

In a fourth embodiment, a siloxane molecule containing one or more aldehyde groups as an end-functional group is made to bind to the surface of a MRI-imageable metal oxide nanoparticle. After binding, the aldehyde-functionalized siloxane molecule contains an aldehyde group directed away from the nanoparticle surface such that it is available to react and bind with an aldehyde-reactive group (typically, amino groups) present in a suitable biofilm-targeting moiety.

In a fifth embodiment, a siloxane molecule containing one or more epoxy groups as an end-functional group is made to bind to the surface of a MRI-imageable metal oxide nanoparticle. After binding, the epoxy-functionalized siloxane molecule contains an epoxy group directed away from the nanoparticle surface such that it is available to react and bind with amino (or hydroxy) groups present in an amino- or hydroxy-containing biofilm-targeting moiety. Some examples of epoxy-functionalized siloxanes include (3-glycidoxypropyl)trimethoxysilane (CAS 2530-83-8), (3-glycidoxypropyl)methyldimethoxysilane (CAS 65799-47-5), (3-glycidoxypropyl)methyldiethoxysilane (CAS 2897-60-1), (3-glycidoxypropyl)dimethylethoxysilane (CAS 17963-04-1), 5,6-epoxyhexyltriethoxysilane, and 2-(3,4-epoxycyclohexyl)ethyltrimethoxysilane (CAS 3388-04-3).

In a sixth embodiment, a siloxane molecule containing one or more alkyl halide groups as an end-functional group is made to bind to the surface of a MRI-imageable metal oxide nanoparticle. After binding, the alkyl halide-functionalized siloxane molecule contains an alkyl halide group directed away from the nanoparticle surface such that it is available to react and bind with amino or thiol groups present in an amino- or thiol-containing biofilm-targeting moiety. Some examples of such halide-functionalized siloxanes include 11-bromoundecyltrimethoxysilane, 3-bromopropyltrimethoxysilane (CAS 51826-90-5), and 3-iodopropyltrimethoxysilane (CAS 14867-28-8).

In a seventh embodiment, a siloxane molecule containing one or more isocyanate groups as an end-functional group is made to bind to the surface of a MRI-imageable metal oxide nanoparticle. After binding, the isocyanate-functionalized siloxane molecule contains an isocyanate group directed away from the nanoparticle surface such that it is available to react and bind with amino or hydroxy groups present in an amino- or hydroxy-containing biofilm-targeting moiety. An example of such an isocyanate-functionalized siloxane includes 3-isocyanatopropyltriethoxysilane (CAS 24801-88-5).

A functionalized (reactive) siloxane, such as any of the types of functionalized siloxanes described above, typically comprises a portion (i.e., less than 100%) of the total amount of siloxane molecules coating the surface of the metal oxide nanoparticle, the remainder of the siloxane molecules not possessing an end-reactive group (i.e., non-functionalized siloxanes). The non-functionalized siloxanes can be hydrophobic or hydrophilic, but are more preferably hydrophilic in order to prevent agglomeration during storage or in the body after administration.

Some examples of hydrophobic non-functionalized siloxane molecules include those belonging to the class according to the formula $Si(R)_{4-m}(OR)_m$, wherein the subscript m can have a value of 1, 2, or 3, and R independently represents a hydrocarbon (i.e., hydrophobic) group, which can be saturated or unsaturated, and straight-chained, branched, or cyclic. The R groups can independently contain any number of carbon atoms, but more typically, the alkoxy R group contains 1 to 6 carbon atoms (more typically 1 to 3 carbon atoms) whereas the R group connected to Si often contains more carbon atoms, e.g., 3-20 carbon atoms. Some examples of such hydrophobic non-functionalized siloxanes include ethyltrimethoxysilane, diethyldimethoxysilane, triethylmethoxysilane, n-propyltrimethoxysilane, n-butyltrimethoxysilane, n-pentyltrimethoxysilane, n-hexyltrimethoxysilane, allytrimethoxysilane, and the like.

The hydrophilic non-functionalized siloxane molecules include those belonging to the class according to the formula $Si(R')_{4-m}(OR)_m$, wherein R' is defined as an R group, as described above, modified to contain a generally non-reactive hydrophilic group, such as any number of ethylene oxide (EO) groups, hydroxy groups, amine linkages, or amide linkages. Some examples of such hydrophilic non-functionalized siloxane molecules include N-(3-triethoxysilylpropyl)-4-hydroxybutyramide (CAS 186543-03-3), N-(3-triethoxysilylpropyl)gluconamide (CAS 104275-58-3), N-(3-methacryloxy-2-hydroxypropyl)-3-aminopropyltriethoxysilane (CAS 96132-99-8), hydroxymethyltriethoxysilane (CAS 162781-73-9), N-(hydroxyethyl)-N-methylaminopropyltrimethoxysilane, bis(2-hydroxyethyl)-3-aminopropyltriethoxysilane (CAS 7538-44-5), and N-(3-acryloxy-2-hydroxypropyl)-3-aminopropyltriethoxysilane (CAS 123198-57-2).

In some embodiments, the functionalized (reactive) siloxane molecules comprise no more than about 50% of the total number of siloxane molecules. For example, in some embodiments, the functionalized siloxane molecules may comprise up to about 40%, or up to about 30%, or up to about 20%, or up to about 10%, or up to about 5%, or up to about 2%, or up to about 1% of the total amount of siloxane molecules. For example, in different embodiments, it may be preferred to coat a metal oxide nanoparticle with a combination of siloxane molecules comprised of 1 to 20 molar percent of a functional siloxane (e.g., amino-, thiol-, epoxy-, halide-, or isocyanato-functionalized siloxane) and 80-99 molar percent of a non-functional siloxane (e.g., a hydrophobic or hydrophilic non-reactive siloxane described above).

The biofilm-targeting moiety can also be linked to the nanoparticle by a coupling agent which contains a biological linking component. In one embodiment, the biofilm-targeting moiety can be linked to the nanoparticle by making use of the well-known specific binding of biotin to avidin or streptavidin. For example, a biotinylation reagent can be reacted with a functionalized nanoparticle to functionalize the nanoparticle with biotin. The biotin-functionalized nanoparticle can then be reacted with a biofilm-targeting moiety conjugated to avidin or streptavidin to form a biotin-avidin or biotin-streptavidin complex.

In one embodiment, an amino-functionalized nanoparticle described above is reacted with an amine-reactive biotinylation reagent to functionalize the nanoparticle with biotin. Some examples of amine-reactive biotinylation reagents include the class of molecules containing biotin on one end and, for example, a succinimide ester, pentafluorophenyl ester, or alkyl halide group on the other end. The biotin group and amine-reactive group can be separated by any suitable spacer group of any length (e.g., 8-40 Å in length). Some examples of amine-reactive biotinylation reagents are available from Pierce under the EZ-Link® trade name, e.g., as NHS-biotin (containing a five-carbon ester linkage between biotin and NHS), sulfo-NHS-biotin, NHS-LC-biotin, sulfo-NHS-LC-Biotin, NHS-LC-LC-biotin, sulfo-NHS-LC-LC-biotin, sulfo-NHS—SS-biotin, NHS-PEO$_4$-biotin, PFP-biotin, TFP-PEO-biotin, and the like, wherein "NHS" refers to a N-hydroxysuccinimide group, "LC" refers to a six-carbon amide-containing linkage inserted between the NHS group and biotin or between another LC group and biotin, "PEO" refers to an ethyleneoxide group, wherein the associated subscript indicates the number of linked PEO units, "PFP" refers to a pentafluorophenyl group, "TFP" refers to a tetrafluorophenyl group, "sulfo" refers to a sulfonate ($SO_3^-Na^+$) group, and "SS" refers to a disulfide bond.

In another embodiment, a thiol-functionalized nanoparticle described above is reacted with a thiol-reactive biotinylation reagent to functionalize the nanoparticle with biotin. Some examples of thiol-reactive biotinylation reagents include the class of molecules containing biotin on one end and, for example, a maleimido or alkyl halide group on the other end. The biotin group and thiol-reactive group can be separated by any suitable spacer group of any length, as above. Some examples of thiol-reactive biotinylation reagents are available from Pierce under the EZ-Link® trade name, e.g., as maleimide-PEO$_2$-biotin, biotin-BMCC (contains an end-maleimido group and one cyclohexyl, two amide linkages, and nine additional linking carbon atoms), PEO-iodoacetyl biotin, iodoacetyl-LC-biotin, biotin-HPDP (contains a pyridyl disulfide group), and the like.

The biotin-functionalized nanoparticle can then be reacted with an avidin or streptavidin conjugate of a biofilm-targeting moiety such that a biofilm-specific probe is produced which contains the nanoparticle conjugated to the biofilm-targeting moiety by a biotin-avidin or biotin-streptavidin link.

In another embodiment, the nanoparticle is conjugated to avidin or streptavidin and the avidin- or streptavidin-functionalized nanoparticle reacted with a biotinylated biofilm-targeting moiety such that a biofilm-specific probe is produced which contains the nanoparticle conjugated to the biofilm-targeting moiety by an avidin-biotin or streptavidin-biotin link.

In a preferred embodiment, the nanoparticle core is coated with Protein A and the Protein A-coated nanoparticle contacted with an antibody against a biofilm antigen (preferably an IgG type of antibody) in order to produce an antibody-nanoparticle conjugate that can function as a biofilm-specific probe. An advantage of the foregoing embodiment is that Protein A preferentially binds to the $F_c$ region of an antibody, and thus, directs the variable targeting region ($F_v$ region) outwardly. By orienting the $F_v$ region outwardly, the antibody is provided the maximum opportunity to find its target. As a result, the biofilm-specific probe can bind more effectively and efficiently to the targeted antigen, and thus, provide optimal results when conducting an MRI scan.

In one embodiment, the biofilm-specific probe is composed of a nanoparticle conjugated to a single type of biofilm-targeting moiety. In another embodiment, the biofilm-specific probe is composed of a nanoparticle conjugated to more than one type of biofilm-targeting moiety. The different types of biofilm-targeting moieties can be different in that they target different antigens while being of the same class of targeting agent (e.g., they can be all antibodies that target different antigens). Alternatively, or in addition, the biofilm-targeting moieties can be different in that they belong to different classes of targeting agents (e.g., one is an antibody and the other a peptide or polysaccharide). A biofilm-specific probe containing more than one type of targeting agent may contain any number of different targeting agents, e.g., two, three, four, five, or an assortment of up to ten or more targeting agents. A biofilm-specific probe containing a number of different targeting agents can be advantageous in that a number of different possible types of biofilm infections can be screened for in one administration of the probe, without requiring advance knowledge of the type of biofilm infection present in the subject.

Since the biofilm-specific probes described above are to be administered to a subject, the probes can be optionally combined with a suitable pharmaceutical carrier (i.e., vehicle or excipient). Any of the excipients known in the art can be suitable herein depending on the mode of administration. Some examples of suitable carriers include gelatin, fatty acids (e.g., stearic acid) and salts thereof, talc, vegetable fats or oils, gums and glycols, starches, dextrans, and the like.

A pharmaceutical composition of the biofilm-specific probes can also include one or more stabilizers, surfactants, salts, buffering agents, additives, or a combination thereof. The stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted and buffered.

The method for in vivo detection of a biofilm in a subject begins with administration of the above-described biofilm-specific probe (i.e., probe) into a subject. The probe can be administered to the subject in any suitable manner that can allow the probe to find a suspected biofilm infection. For example, the probe can be administered enterally (i.e., orally), parentally (i.e., by infusion through the skin), topically (i.e., on the skin), or by injection (e.g., intravenously or intramuscularly). For oral administration, liquid or solid oral formulations can be given. These include, for example, tablets, capsules, pills, troches, elixirs, suspensions, and syrups.

The biofilm-specific probe is administered in a diagnostic-effective amount. A diagnostic-effective amount is an amount which allows a sufficient amount of the probe to bind to a biofilm infection such that the biofilm infection can be observed by scanning a subject using a magnetic resonance diagnostic technique. The amount of probe administered depends on several factors, including the chemical nature (e.g., molar weight of the probe and image contrast ability), weight of the subject, and other factors. A diagnostic-effective amount is typically within the range of, for example, 10-1000 mg of the probes per an administration. In some embodiments, the diagnostic effective amount is about 10 mg, about 25 mg, about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg or about 1000 mg.

The biofilm-specific probes can be administered once in a single dosage before observation of the subject by a magnetic resonance diagnostic technique. Alternatively, the probes can be administered in separate doses before one or more observations. The probes can also be administered in separate doses or in a continuous mode during observation such that the moment of binding of the probes to the biofilm target can be observed, and/or the progress of binding monitored. In addition, the subject can be administered a formulation which releases the probes into the subject in a controlled manner over time (i.e., as a controlled release formulation).

After the biofilm-specific probes have been administered to a subject and given a suitable amount of time to bind to the target in sufficient quantity, the biofilm infection, if any, is observed by scanning the subject using a magnetic resonance diagnostic technique. The magnetic resonance diagnostic technique is typically a magnetic resonance imaging (MRI) technique, which refers to any of the techniques known in the art that subjects an organism to a powerful magnetic field in conjunction with radio waves to detect differences in the relaxation behavior of protons or other atom types in different parts of the organism, and by these differences observe features and/or physiological activity in the organism.

Any of the different types of MRI techniques can be used herein. These include, for example, standard MRI, magnetic resonance spectroscopy (i.e., MRS or MRSI), functional MRI, multinuclear imaging (e.g., based on He-3, C-13, F-19, O-17, Na-23, P-31, or Xe-129), and several others. In addition, the MRI technique can be performed in the standard enclosed manner or as open MRI.

The magnetic resonance technique can also be performed in conjunction with one or more other diagnostic techniques. The other techniques can be performed according to standard methods and can be useful for confirming the presence of the biofilm infection or observing additional properties of behavior of the biofilm infection not capable of being observed solely by the magnetic resonance technique. Some examples of these other techniques include positron emission detection techniques (e.g., positron emission tomography (PET) or single photon emission computed tomography (SPECT)), and fluoroscopic imaging (i.e., fluoroscopy). These other techniques can be conducted by administering a formulation containing either a positron-emitting radionuclide or fluorescing material (e.g., quantum dot nanoparticle), respectively.

In one embodiment, the radionuclide or fluorophore is conjugated to a biofilm-targeting moiety, and administered before, during, or after administration of the biofilm-specific probe of the invention, and the positron emission or fluoroscopy technique performed in a standard manner.

In another embodiment, the radionuclide or fluorophore is conjugated to a chemical group which targets the bound biofilm-targeting probe of the invention. The latter type of targeting agent is herein also referred to as a "probe-targeting moiety." The positron emission or fluoroscopy technique can then be performed in a standard or modified manner.

In yet another embodiment, the radionuclide and/or fluorophore is conjugated to the bio film-targeting probe of the invention. By conjugating these additional markers to the probes described above, the probes advantageously become multifunctional. The multifunctional probes advantageously eliminate the need for multiple administrations of different types of probes by including more than one type of observable marker onto a single probe.

For example, the biofilm-targeting probe of the invention can be made additionally observable by a positron emission detection technique by conjugating a suitable positron-emitting radionuclide to the biofilm-targeting probe. Some examples of suitable positron-emitting radionuclides include technetium-99, fluorine-18, fluorine-19, carbon-11, iodine-123, nitrogen-13, and oxygen-15. The radionuclide can be conjugated to the probe by any suitable means. One method for conjugating the radionuclide includes attachment to the probe of a chemical group that contains the radionuclide of interest. For example, a fluorodeoxyglucose (18F-FDG) molecule, or modified version thereof, can be conjugated by crosslinking methods described above to a biofilm-targeting probe of the invention, thus rendering the probe observable by both MRI and PET or SPECT.

The biofilm-specific probe described above can also function as a secondary probe by targeting a first probe that has already targeted the biofilm infection. The first (primary) biofilm-targeting probe can be any desired probe which selectively targets a biofilm infection. For example, in one embodiment, a first biofilm-targeting probe also contains a paramagnetic nanoparticle in accordance with the probes described above. By having a secondary probe, which also contains a paramagnetic nanoparticle, target the first probe, there can be provided an amplification effect in the observability and imaging of the biofilm infection as compared to the case where only a single paramagnetic probe is used. Even more, the amplification can be further enhanced by administration of any number of successively-administered probes, each probe being selective against the preceding probe. In this manner, a significantly increased amount of contrast agent material can be deposited at the biofilm infection, thereby allowing the biofilm infection to be significantly more contrasted with neighboring tissue. This amplification effect cannot be realized by administration of a single dose of the probes since probes of such size would be rejected by the subject's immune system and also suffer from significantly hindered penetration ability. Accordingly, the foregoing embodiment provides the added advantage of, in effect, targeting unusually large agglomerations of paramagnetic particles to a biofilm infection while avoiding problems associated with directing such large particles to their targets.

The first biofilm-targeting probe can also be a biofilm-targeting molecule that is not conjugated to a paramagnetic particle. For example, the first probe can be administered as one or more antibodies against one or more possible antigens of one or more possible biofilm infections. Then a secondary probe containing the paramagnetic nanoparticle conjugated to a biofilm-targeting moiety selective against the first probe can be administered. An advantage to the foregoing embodiment is that first, a conjugation step is eliminated in synthesizing the first probe since the first probe is a biofilm-targeting moiety not conjugated to a paramagnetic nanoparticle; and second, the secondary probe can be made available as a standardized reagent which does not require customization for each possible biofilm infection or the type of antigen being targeted, but rather, according to the nature of the first probe. For example, the first probe can be administered as one or several different mouse-(anti-biofilm) antibodies, with one or several possible antigenic sites being targeted. After binding of the first probe, the secondary probe need only be the paramagnetic nanoparticle conjugated to an anti-mouse antibody or active fragment thereof. Accordingly, the method is simplified in that only one type of secondary probe need be available for any variety of first probes being used.

In another aspect, the invention is directed to methods for treating the biofilm infection. The method for treating the biofilm infection works in conjunction with determining the location, type, and severity of the infection using the magnetic resonance diagnostic technique. Once the location, type, and severity of biofilm infection has been determined using MRI and any other techniques, the infection can be treated in any suitable manner. The biofilm infection can be treated conventionally by the administration of antibiotics, or by surgery (e.g., debridement), or by, for example, magnetic resonance-guided focused ultrasound, wherein ultrasound beams are focused on a tissue such that the tissue is ablated.

More preferably, the bio film infection is treated non-invasively by using the biofilm-specific probes of the invention that are already attached to the biofilm infection during diagnosis. For example, radioactive metals that destroy surrounding tissue can be incorporated into the probes so that, when the probes bind to the target, the radioactive portion therein focuses its destructive energy on surrounding infected tissue. Some examples of radioactive metals that may be incorporated into the probe include I-123, I-125, Pd-103, Cs-137, Ra-226, or Ir-192. These metals can be incorporated into a probe in the form of, for example, a radiolabeled antibody. Alternatively, the biofilm-specific probes can include a conjugated antibody capable of destroying the biofilm infection.

In a preferred embodiment, the biofilm-specific probes, once attached to the bio film infection and after or during inspection with an MRI technique, are exposed to a source of thermal-inducing (i.e., photothermal) radiation such that the paramagnetic nanoparticles are heated to a level wherein surrounding tissue is ablated. The source of thermal-inducing radiation needs to be of a wavelength and intensity such that, over a sufficient period of exposure time, sufficient ablation can be realized so that the infection is diminished or removed.

The thermal-inducing radiation can be, for example, infrared radiation. In a particular embodiment, the thermal-inducing radiation is near-infrared (i.e., near-IR or nIR). Typically, the range of near-IR wavelengths considered herein for ablation are within the range of about 700 to about 2500 nm, and more preferably about 700 to about 1,000 nm. For example, in certain embodiments, the ablation may be conducted by exposing the bound probes to near-infrared radiation of about 820 nm wavelength at a power setting of about 4 W/cm$^2$.

The thermal ablation procedure described above operates by direct action of the thermal-inducing radiation on the nanoparticle of the biofilm-specific probe. However, it is also possible to accomplish, promote, or modulate the ablation procedure by use of a separate heat-inducible nanoparticle. The separate heat-inducible probe would be administered during or after the MRI diagnostic procedure and then be exposed to near-IR radiation to cause ablation of the surrounding tissue. For example, after the biofilm-specific probes have targeted the biofilm infection, a secondary probe composed of gold nanoparticles conjugated to a molecule selective against the biofilm-specific probe can be administered. Near-IR radiation is then shined on the subject in the vicinity of the biofilm infection where the gold nanoparticles have bound. The near-IR radiation will then be transmitted mainly unabsorbed through body tissue until it interacts with the gold and/or paramagnetic nanoparticles, at which point the near-IR radiation is strongly absorbed to generate heat.

The gold or other heat-inducible metal can also be in the form of a nanoshell, i.e., a coating of the gold or other heat-inducible metal on either the paramagnetic metal or other metal nanoparticle. In order for the ablation to be effective, surrounding tissue should be heated to a high enough temperature that can cause ablation. Typically, the ablation step is carried out such that immediate surrounding tissue (e.g., within about 0.1-0.5 mm locus of the nanoparticle) increases by at least about 10-20° C. and retains at least this temperature for sufficient time (e.g., 1-30 minutes). The ablation can be conducted at higher temperatures, e.g., an increase in temperature of at least about 40° C., 50° C., or 60° C. The use of higher temperatures allows for shorter time periods of tissue exposure to the higher temperatures. Thus, for example, an ablation step can be conducted by raising the local tissue temperature by about 50° C. and using an exposure time of 0.5-2 minutes.

Ablation can also be achieved by exposure of the bound nanoparticles to radiofrequency (RF) radiation, particularly the alternating RF (magnetic) fields emitted by a magnetic resonance imaging machine. For example, the bound nanoparticles can be exposed to an approximately 100 kHz alternating current magnetic field for about 30 minutes in order to heat surrounding tissue to a temperature within 40-50° C.

In a further aspect, the invention is directed to compositions useful to detect and/or treat a biofilm infection. The compositions comprise one or more components that are useful in carrying out the methods of the present invention as described herein. In one embodiment, the composition comprises a diagnostic-effective amount of a biofilm-specific probe, wherein the probe comprises a biofilm-targeting moiety and a nanoparticle core, wherein the nanoparticle core comprises a paramagnetic material observable by a magnetic resonance diagnostic technique. In some embodiments, the biofilm-targeting moiety is an antibody that binds a biofilm-specific antigen. In some embodiments, the antigen is selected from the group consisting of SEQ ID NO:1, SEQ ID NO:2, SEQ ID NO:3, SEQ ID NO:4, SEQ ID NO:13 and SEQ ID NO:43. In some embodiments, the nanoparticle core has a diameter of at least about 1 nanometer and up to about 300 nanometers.

In a further aspect, the invention is directed to kits for the detection and/or treatment of biofilm infections. The kits of the invention comprise one or more components that are useful in carrying out the methods of the present invention as described herein. In one embodiment, the kit comprises a diagnostic-effective amount of a biofilm-specific probe, wherein the probe comprises a biofilm-targeting moiety and a nanoparticle core, wherein the nanoparticle core comprises a paramagnetic material observable by a magnetic resonance diagnostic technique. In some embodiments, the biofilm-targeting moiety is an antibody that binds a biofilm-specific antigen selected from the group consisting of SEQ ID NO:1, SEQ ID NO:2, SEQ ID NO:3, SEQ ID NO:4, SEQ ID NO:13 and SEQ ID NO:43. In some embodiments, the kit comprises an antibody that binds a biofilm-specific antigen that is not conjugated to a nanoparticle. In this embodiment, the kit further comprises a biofilm-specific probe comprising a biofilm-targeting moiety that binds to the antibody and a nanoparticle core, wherein the nanoparticle core comprises a paramagnetic material observable by a magnetic resonance diagnostic technique. In some embodiments, the kit comprises components that are useful in treating the biofilm infection. For example, in some embodiments, the kit further comprises a near infrared-heat inducible nanoparticle that binds to a biofilm-specific probe.

Examples have been set forth below for the purpose of illustration and to describe the best mode of the invention at the present time. However, the scope of this invention is not to be in any way limited by the examples set forth herein. Throughout this application, various publications and citations are referred to. Disclosures of these publications and citations are hereby incorporated by reference into this application.

Example 1

Preparation of Functionalized Paramagnetic Particles

In a variation of the Stöber process (see references below), 2-propanol, water, and washed ferrofluid are combined and sonicated in a ratio of $5:1:1.25\times10^{-4}$, respectively (total volume=48.1 mL) in a round-bottom flask suspended in ultrasonic water bath (e.g., Bransonic Model B2510). After an initial dispersion period, 10 μL of tetraethyl orthosilane (TEOS) and 500 μL of concentrated $NH_4OH$ are added. The reaction proceeds with constant sonication for 90 min. before 5 μL aminopropyltriethoxysilane (APTES) in 52 μL dimethylformamide are added. Sonication is continued for an additional 60 min. or until such time as a layered coating of silica is achieved on all nanoparticles, either singly or in small clusters. The corresponding Stöber process is described in, for example, Stöber, W., et al., *J. Coll. and Inter. Sci.*, 26: 62-69 (1968); Lu, Y., et al., *Nano Letters* 2: 183-186 (2002); and Niedbala R. S., et al., *Anal. Biochem.* 293: 22-30 (2001).

According to an alternative process, to a clean 10 mL round-bottom flask (cleaned with soap and water and rinsed with 2-propanol) was added 5 mL of 2-propanol (Reagent Grade) and 500 μL of APTES. The flask was then suspended in a sonicator bath (Aquasonic Model 550D or equivalent) set at 20° C. (filled to operation level and degassed for 5 minutes) in order to allow the mixture to degas. To the degassed mixture was added 10 μL Ferrotec EMG 308 or similar paramagnetic particles (PMP). The mixture was then briefly swirled and sonicated (1-3 min). A nitrogen atmosphere set up (e.g., $N_2$-filled balloon attached to flask with septum) was then assembled. The mixture was then allowed to react for 24 hours on a rocker in the hood before being transferred to a 50-mL conical tube and inserting the tube into a magnetic separator (LifeSep 50SX or similar). The reaction mixture was then decanted by first gathering the coated PMP to the side of the flask using the magnetic separator for 10 minutes and then pouring off the supernatant. The particles were then repeatedly rinsed gently with copious amounts of DI water.

EXAMPLE 2

Conjugation of Avidin to Functionalized Paramagnetic Particles

The functionalized particle suspension of Example 1 (APTES-PMP) was sonicated for 10 min to ensure homogeneous dispersion of the solid phase. After sonication, the contents were transferred into a storage tube where the solid phase was gathered by magnetic aggregation and the supernatant removed. Following this, the solid was washed three times with phosphate buffer saline (PBS, pH of 7.2) solution. Then the particles were incubated with a solution containing 0.5 mg avidin/250 μL of PBS. The avidin used was Nuetra Avidin (M.W.=$1.5\times10^{-8}$ mol/mg) available from Pierce. The final incubation volume was about 1 mL (250 μL avidin+450 μL PMPs+300 μL PBS). The solution was then incubated with gentle agitation (e.g., using a rocker) for about 1 hr. After incubation, the supernatant was removed using magnetic aggregation and the particles washed once in 1 ml of fresh PBS. Magnetic aggregation was again used to remove the buffer, and the particles suspended in a 25 mM solution of sulfosuccinimidyl suberate (BS3, M.W.=572.43 g/mol) available from Pierce. The suspension was incubated for 30 min and quenched with 1 mL of a 10% glycine solution. Magnetic aggregation was again used to remove the buffer and glycine solution, before resuspending the particles in 1 mL of fresh PBS. The avidinylated particles were stored at 4° C. in the dark until antibody conjugation.

EXAMPLE 3

Conjugation of Biotinylated Antibodies to Avidinylated Paramagnetic Particles A 10 mg portion of the avidinylated PMP from Example 2 was re-suspended in 1 mL PBS solution. Biotinylated antibody was added to the solution in a 5:1 weight ratio to PMPs. The suspension was allowed to incubate with gentle agitation at 4° C. (in a cold room) for 30 minutes. Using magnetic decantation, the excess solution was poured off and 1 mL fresh PBS added. The suspension was agitated gently by inverting the tube. The foregoing magnetic decantation, addition of 1 mL fresh PBS, and agitation was repeated three times. After final re-suspension in PBS, the particles were stored at 4° C. until use.

EXAMPLE 4

Preparation of Biofilm-Targeting Groups

In one embodiment, *Escherichia coli* expressing MRSA biofilm proteins are grown while shaking at room temperature in Luria-Bertani broth with 1 µg/ml ampicillin until $OD_{600}$=0.6. The cells are then induced with 10 µg/ml anhydrotetracycline (IBA) and allowed to shake for an additional three hours. After induction, the cells are pelleted by centrifugation (e.g., 3500 rpm for 30 minutes) and re-suspended in a periplasmic lysis buffer containing 100 mM Tris/HCl (pH 8), 500 mM sucrose and 1 mM EDTA. After a 30-minute incubation on ice the spheroplasts are centrifuged as before and the lysate is collected for purification.

Lysate containing a recombinant biofilm-specific protein is added to a 5 CV bed volume Strep-tactin flow column (IBA, 2-1207-051) and the protein of interest is purified. Six elutions of 3 mL each are collected for each protein and western blot analysis is performed to confirm purity. The elutions containing purified protein are concentrated and dialyzed in PBS (pH 7.4) by preferably using Microcon 10,000 MWCO filters (Millipore, 42407). Protein concentrations are determined by preferably using a standard BCA protein assay (Pierce, 23225).

These proteins are then used as antigens to generate biofilm-specific antibodies by the use of standard methods for the generation of either polyclonal or monoclonal antibodies.

EXAMPLE 5

Treatment of Bio films

Biofilms were grown for 3 days in glass-bottom 24-well plates, replacing the spent media with fresh media every 24 hrs at 37° C. The bio film-specific antibodies were then linked to the paramagnetic nanoparticles and these conjugates incubated with either the Staphylococcal biofilm or the *P. aeruginosa* biofilm and then fluorescence observed using an epifluorescent microscope.

Figure 2:
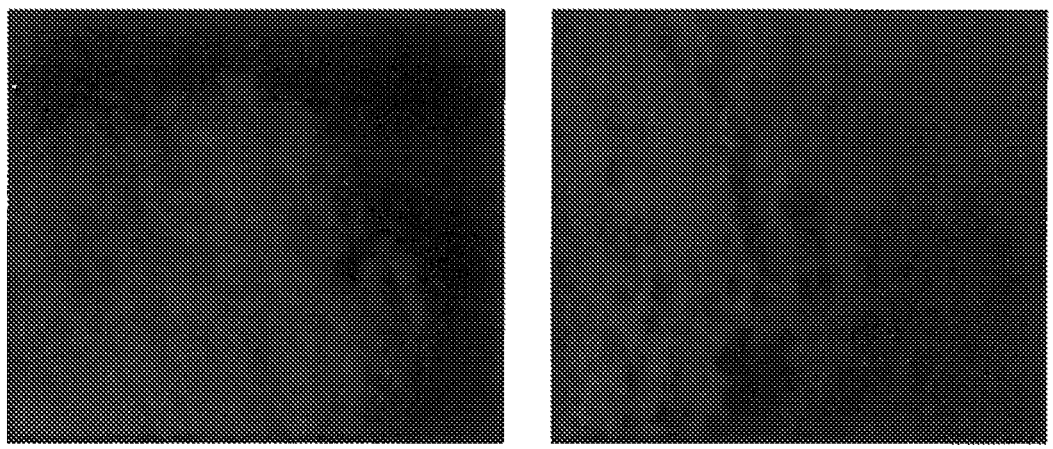
FIG. 2 Micrograph of a MRSA biofilm stained with fluorescent IgG-labeled paramagnetic particles (PMPs).

FIG. 2 shows micrographs of a three-day old MRSA biofilm stained with fluorescent IgG-labeled paramagnetic particles. As shown, staining of the bio film is evident.

Figure 3:
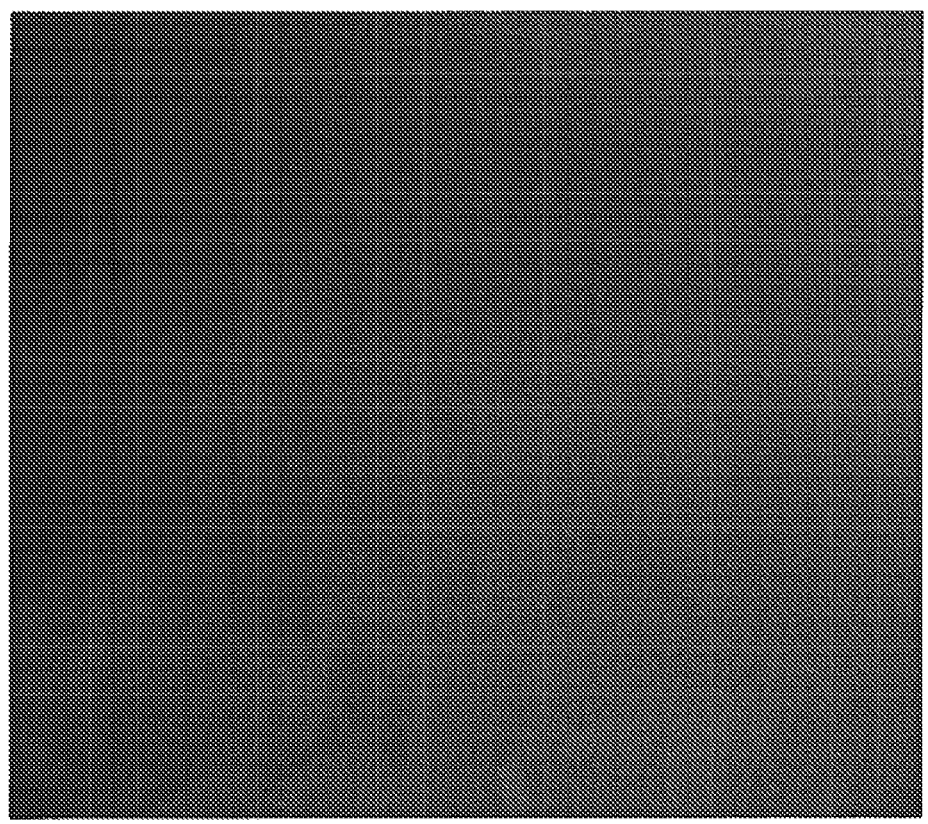
FIG. 3 Micrograph of a *P. aeruginosa* biofilm stained with anti-*S. aureus* biofilm-specific nanoparticles.

FIG. 3 shows a three-day old *Pseudomonas aeruginosa* biofilm treated with anti-*S. aureus* biofilm-specific nanoparticles. Significantly, no fluorescent staining is evident. The anti-*S. aureus* biofilm-specific nanoparticles also did not stain *Bacillus anthracis* bio films (results not shown).

Figure 4:
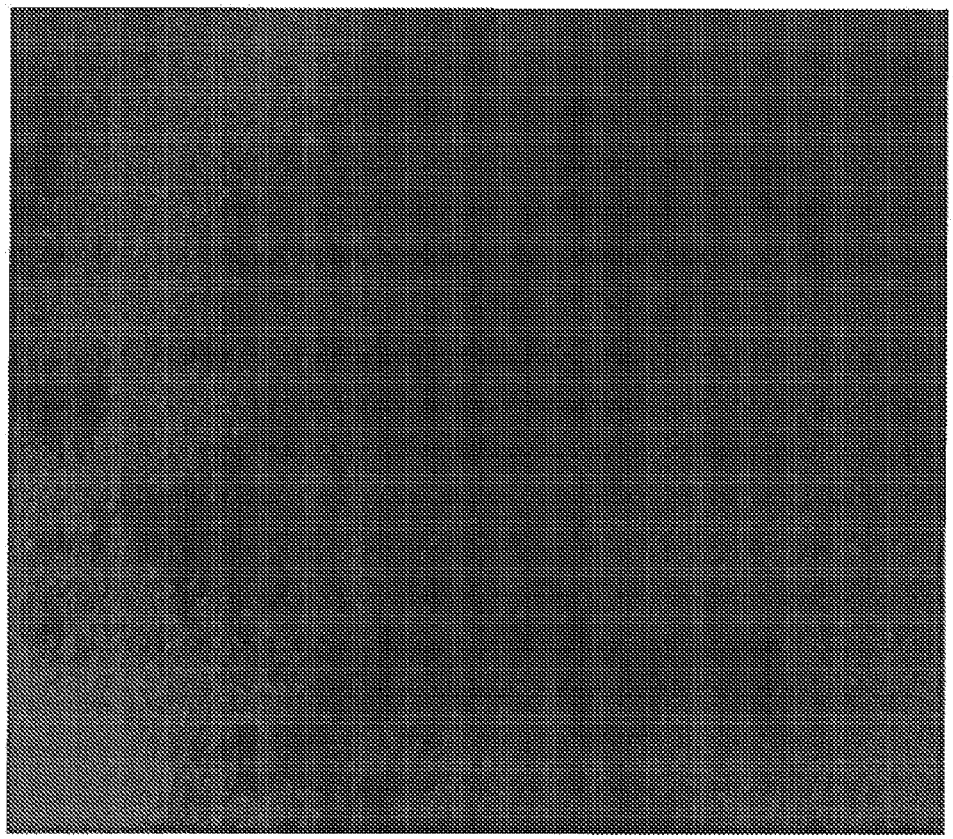
FIG. 4 Comparative micrograph of an *S. aureus* biofilm stained with the LIVE/DEAD® kit.

FIG. 4 shows a three-day old *S. aureus* biofilm stained with the commercially available LIVE/DEAD® kit. As shown, the staining from the LIVE/DEAD® kit is much less visible than the staining shown in FIG. 2 using the labeled paramagnetic particles of the invention.

The biofilm-specific particles (for *Staphylococcus*) stained the staphylococcal biofilm (as shown in FIG. 1) but not the *P. aeruginosa* biofilm (as shown in FIG. 2). For use as a positive control, another Staphylococcal biofilm (FIG. 3) was grown for three days and stained with the Prokaryotic Live/Dead® kit from Molecular Probes/Invitrogen. For these studies, both the Live/Dead® stain and the nanoparticles were simple perfused over the biofilms in liquid media (growth media for the bacteria).

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

---

What is claimed is:

1. A method for in vivo detection of a *Staphylococcus* biofilm infection residing in a mammal, the method comprising: (i) administering to the mammal a diagnostic-effective amount of a biofilm-specific probe, wherein the probe comprises a biofilm-targeting moiety and a nanoparticle core, wherein the nanoparticle core comprises a paramagnetic material observable by a magnetic resonance diagnostic technique; and (ii) imaging the mammal using a magnetic resonance diagnostic technique after said biofilm-specific probe has been provided sufficient time to bind to the biofilm infection, thereby detecting the presence of the biofilm infection in the mammal, wherein the biofilm-targeting moiety binds to an antigen selected from the group consisting of SEQ ID NO:1, SEQ ID NO:2, SEQ ID NO:3, SEQ ID NO:4, SEO ID NO: 13 and SEO ID NO:43.

2. The method according to claim 1, wherein the nanoparticle has a diameter selected from the group consisting of up to about 100 nanometers, up to about 50 nanometers, up to about 30 nanometers, up to about 20 nanometers, at least about 10 and up to about 30 nanometers, at least about 10 and up to about 20 nanometers, and at least about 1 nanometer and up to about 300 nanometers.

3. The method according to claim 1, wherein the nanoparticle core is bound to the biofilm-targeting moiety through one or more linking moieties.

4. The method according to claim 3, wherein the linking moiety is within a self-assembled monolayer encapsulating the nanoparticle core.

5. The method according to claim 4, wherein the linking moiety and self-assembled monolayer are comprised of siloxane groups that have formed siloxy bonds with the surface of the nanoparticle core, and optionally, siloxy bonds between siloxane groups, wherein the linking moiety possesses a functional group that binds to the biofilm-targeting moiety either directly or through a separate crosslinking group.

6. The method according to claim 1, wherein the biofilm-targeting moiety is a biological material that selectively targets one or more types of biofilm microorganisms.

7. The method according to claim 6, wherein the biological material is an antibody or antibody component raised against the antigen.

8. The method according to claim 7, wherein the antibody is selected from the group consisting of a whole antibody that includes an $F_c$ region and an antibody fragment that does not include an $F_c$ region.

9. The method according to claim 8, wherein the antibody is an antibody fragment selected from the group consisting of a $(Fab')_2$ fragment and a Fab fragment.

10. The method according to claim 1, wherein the magnetic resonance diagnostic technique is magnetic resonance imaging.

11. The method according to claim 1, wherein the biofilm-specific probe further comprises a positron-emitting radionuclide suitable for being observed using a positron emission detection technique in conjunction with a said magnetic resonance diagnostic technique, wherein the radionuclide is selected from the group consisting of technetium-99, fluorine-18, carbon-11, iodine-123, nitrogen-13, and oxygen-15.

12. The method according to claim 1, further comprising an additional step of ablating the biofilm after said biofilm-specific probe is bound to said biofilm, the additional step comprising exposing the attached biofilm-specific probe to thermal-inducing radiation selected from the group consisting of radio frequency radiation, infrared radiation and near-infrared radiation.

13. The method according to claim 1, further comprising an additional step of selectively binding a near infrared-heat inducible nanoparticle to said biofilm-specific probe after said biofilm-specific probe is bound to said biofilm, and then exposing the attached near IR-heat inducible nanoparticle to near-infrared radiation in order to ablate the biofilm.

14. A composition comprising a biofilm-specific probe, wherein the probe comprises a biofilm-targeting moiety and a nanoparticle core, wherein the nanoparticle core comprises a paramagnetic material observable by a magnetic resonance diagnostic technique, wherein the biofilm-targeting moiety binds to a biofilm-specific antigen selected from the group consisting of SEQ ID NO:1, SEQ ID NO:2, SEQ ID NO:3, SEQ ID NO:4, SEQ ID NO: 13 and SEQ ID NO:43.

15. A kit for the detection of a biofilm infection in vivo comprising a biofilm-specific probe, wherein the probe comprises a biofilm-targeting moiety and a nanoparticle core, wherein the nanoparticle core comprises a paramagnetic material observable by a magnetic resonance diagnostic technique, wherein the biofilm-targeting moiety binds to a biofilm-specific antigen selected from the group consisting of SEQ ID NO:1, SEQ ID NO:2, SEQ ID NO:3, SEQ ID NO:4, SEQ ID NO: 13 and SEQ ID NO:43.

* * * * *

UNITED STATES PATENT AND TRADEMARK OFFICE
CERTIFICATE OF CORRECTION

PATENT NO. : 8,697,375 B2  
APPLICATION NO. : 13/061142  
DATED : April 15, 2014  
INVENTOR(S) : Mark E. Shirtliff et al.

Page 1 of 1

It is certified that error appears in the above-identified patent and that said Letters Patent is hereby corrected as shown below:

Title page

Item [73], Assignees, delete "Arizona Board of Regents A Body Corporate of the State of Arizona" and insert therein -- Arizona Board of Regents, A Body Corporate of the State of Arizona Acting for and on Behalf of Northern Arizona University --.

Signed and Sealed this  
Twenty-ninth Day of July, 2014

Michelle K. Lee  
*Deputy Director of the United States Patent and Trademark Office*

SEQUENCE LISTING

<160> NUMBER OF SEQ ID NOS: 53

<210> SEQ ID NO 1
<211> LENGTH: 261
<212> TYPE: PRT
<213> ORGANISM: Staphylococcus aureus

<400> SEQUENCE: 1

Met Met Gly Asn Ile Lys Ser Phe Ala Leu Tyr Ile Ser Ile Leu Leu
1               5                   10                  15

Leu Ile Val Val Val Ala Gly Cys Gly Lys Ser Asp Lys Thr Lys Glu
            20                  25                  30

```
Asp Ser Lys Glu Glu Gln Ile Lys Ser Phe Ala Lys Thr Leu Asp
         35                  40                  45

Met Tyr Pro Ile Lys Asn Leu Glu Asp Leu Tyr Asp Lys Glu Gly Tyr
 50                  55                  60

Arg Asp Gly Glu Phe Lys Lys Gly Asp Lys Gly Thr Trp Thr Leu Leu
 65                  70                  75                  80

Thr Ser Phe Ser Lys Ser Asn Lys Pro Asp Glu Ile Asp Asp Glu Gly
                 85                  90                  95

Met Val Leu Tyr Leu Asn Arg Asn Thr Lys Lys Ala Thr Gly Tyr Tyr
                100                 105                 110

Phe Val Asn Lys Ile Tyr Asp Asp Ile Ser Lys Asn Gln Asn Glu Lys
                115                 120                 125

Lys Tyr Arg Val Glu Leu Lys Asn Asn Lys Ile Val Leu Leu Asp Asn
130                 135                 140

Val Glu Asp Glu Lys Leu Lys Gln Lys Ile Glu Asn Phe Lys Phe Phe
145                 150                 155                 160

Ser Gln Tyr Ala Asp Phe Lys Asp Leu Lys Asn Tyr Gln Asp Gly Ser
                165                 170                 175

Ile Thr Thr Asn Glu Asn Ile Pro Ser Tyr Glu Ala Gly Tyr Lys Leu
                180                 185                 190

Asn Asn Ser Asp Glu Asn Val Lys Lys Leu Arg Asp Ile Tyr Pro Ile
                195                 200                 205

Thr Thr Lys Lys Ala Pro Ile Leu Lys Leu His Ile Asp Gly Asp Ile
210                 215                 220

Lys Gly Ser Ser Val Gly Tyr Lys Ile Glu Tyr Lys Phe Ser Lys
225                 230                 235                 240

Val Lys Asp Gln Glu Thr Thr Leu Arg Asp Tyr Leu Asn Phe Gly Pro
                245                 250                 255

Ser Asp Glu Asp Ser
                260

<210> SEQ ID NO 2
<211> LENGTH: 168
<212> TYPE: PRT
<213> ORGANISM: Staphylococcus aureus

<400> SEQUENCE: 2

Met Asn Thr Ile Lys Asn Thr Ile Tyr Thr Glu Ala Ile Phe Ser Lys
 1               5                  10                  15

Asp Glu Lys His Arg Tyr Leu Leu Lys Lys Thr Trp Asp Glu Lys Lys
                 20                  25                  30

Pro Ala Cys Thr Val Ile Thr Met Tyr Pro His Leu Asp Gly Val Leu
                 35                  40                  45

Ser Leu Asp Leu Thr Thr Val Leu Ile Leu Asn Gln Leu Ala Asn Ser
 50                  55                  60

Glu Arg Tyr Gly Ala Val Tyr Leu Val Asn Leu Phe Ser Asn Ile Lys
 65                  70                  75                  80

Thr Pro Glu Asn Leu Lys His Ile Lys Glu Pro Tyr Asp Lys His Thr
                 85                  90                  95

Asp Ile His Leu Met Lys Ala Ile Ser Glu Ser Asp Thr Val Ile Leu
                100                 105                 110

Ala Tyr Gly Ala Tyr Ala Lys Arg Pro Val Val Glu Arg Val Glu
                115                 120                 125

Gln Val Met Glu Met Leu Lys Pro His Lys Lys Val Lys Lys Leu
130                 135                 140
```

```
Ile Asn Pro Ala Thr Asn Glu Ile Met His Pro Leu Asn Pro Lys Ala
145                 150                 155                 160

Arg Gln Lys Trp Thr Leu Lys Ala
                165
```

<210> SEQ ID NO 3
<211> LENGTH: 1257
<212> TYPE: PRT
<213> ORGANISM: Staphylococcus aureus

<400> SEQUENCE: 3

```
Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
50                  55                  60

Asn Ile Ser Gly Thr Gln Val Tyr Gln Asp Pro Ala Ile Val Gln Pro
65                  70                  75                  80

Lys Ala Ala Asn Lys Thr Gly Asn Ala Gln Val Asn Gln Lys Val Asp
                85                  90                  95

Thr Thr Gln Val Asn Gly Asp Thr Arg Ala Thr Gln Ser Thr Thr Ser
            100                 105                 110

Asn Asn Ala Lys Pro Val Thr Lys Ser Thr Asn Thr Thr Ala Pro Lys
        115                 120                 125

Thr Asn Asn Asn Val Thr Ser Ala Gly Tyr Ser Leu Val Asp Asp Glu
130                 135                 140

Asp Asp Asn Ser Glu Asn Gln Ile Asn Pro Glu Leu Ile Lys Ser Ala
145                 150                 155                 160

Ala Lys Pro Ala Ala Leu Glu Thr Gln Tyr Lys Ala Ala Ala Pro Lys
                165                 170                 175

Ala Thr Pro Val Ala Pro Lys Ala Lys Thr Glu Ala Thr Pro Lys Val
            180                 185                 190

Thr Thr Phe Ser Ala Ser Ala Gln Pro Arg Ser Ala Ala Ala Ala Pro
        195                 200                 205

Lys Thr Ser Leu Pro Lys Tyr Lys Pro Gln Val Asn Ser Ser Ile Asn
210                 215                 220

Asp Tyr Ile Arg Lys Asn Asn Leu Lys Ala Pro Lys Ile Glu Glu Asp
225                 230                 235                 240

Tyr Thr Ser Tyr Phe Pro Lys Tyr Ala Tyr Arg Asn Gly Val Gly Arg
                245                 250                 255

Pro Glu Gly Ile Val Val His Asp Thr Ala Asn Asp Arg Ser Thr Ile
            260                 265                 270

Asn Gly Glu Ile Ser Tyr Met Lys Asn Asn Tyr Gln Asn Ala Phe Val
        275                 280                 285

His Ala Phe Val Asp Gly Asp Arg Ile Ile Glu Thr Ala Pro Thr Asp
290                 295                 300

Tyr Leu Ser Trp Gly Val Gly Ala Val Gly Asn Pro Arg Phe Ile Asn
305                 310                 315                 320

Val Glu Ile Val His Thr His Asp Tyr Ala Ser Phe Ala Arg Ser Met
                325                 330                 335

Asn Asn Tyr Ala Asp Tyr Ala Ala Thr Gln Leu Gln Tyr Tyr Gly Leu
            340                 345                 350
```

```
Lys Pro Asp Ser Ala Glu Tyr Asp Gly Asn Gly Thr Val Trp Thr His
        355                 360                 365
Tyr Ala Val Ser Lys Tyr Leu Gly Gly Thr Asp His Ala Asp Pro His
370                 375                 380
Gly Tyr Leu Arg Ser His Asn Tyr Ser Tyr Asp Gln Leu Tyr Asp Leu
385                 390                 395                 400
Ile Asn Glu Lys Tyr Leu Ile Lys Met Gly Lys Val Ala Pro Trp Gly
                405                 410                 415
Thr Gln Ser Thr Thr Thr Pro Thr Thr Pro Ser Lys Pro Ser Thr Pro
            420                 425                 430
Ser Lys Pro Ser Thr Pro Ser Thr Gly Lys Leu Thr Val Ala Ala Asn
        435                 440                 445
Asn Gly Val Ala Gln Ile Lys Pro Thr Asn Ser Gly Leu Tyr Thr Thr
    450                 455                 460
Val Tyr Asp Lys Thr Gly Lys Ala Thr Asn Glu Val Gln Lys Thr Phe
465                 470                 475                 480
Ala Val Ser Lys Thr Ala Thr Leu Gly Asn Gln Lys Phe Tyr Leu Val
                485                 490                 495
Gln Asp Tyr Asn Ser Gly Asn Lys Phe Gly Trp Val Lys Glu Gly Asp
            500                 505                 510
Val Val Tyr Asn Thr Ala Lys Ser Pro Val Asn Val Asn Gln Ser Tyr
        515                 520                 525
Ser Ile Lys Pro Gly Thr Lys Leu Tyr Thr Val Pro Trp Gly Thr Ser
    530                 535                 540
Lys Gln Val Ala Gly Ser Val Ser Gly Ser Gly Asn Gln Thr Phe Lys
545                 550                 555                 560
Ala Ser Lys Gln Gln Gln Ile Asp Lys Ser Ile Tyr Leu Tyr Gly Ser
                565                 570                 575
Val Asn Gly Lys Ser Gly Trp Val Ser Lys Ala Tyr Leu Val Asp Thr
            580                 585                 590
Ala Lys Pro Thr Pro Thr Pro Thr Pro Lys Pro Ser Thr Pro Thr Thr
        595                 600                 605
Asn Asn Lys Leu Thr Val Ser Ser Leu Asn Gly Val Ala Gln Ile Asn
    610                 615                 620
Ala Lys Asn Asn Gly Leu Phe Thr Thr Val Tyr Asp Lys Thr Gly Lys
625                 630                 635                 640
Pro Thr Lys Glu Val Gln Lys Thr Phe Ala Val Thr Lys Glu Ala Ser
                645                 650                 655
Leu Gly Gly Asn Lys Phe Tyr Leu Val Lys Asp Tyr Asn Ser Pro Thr
            660                 665                 670
Leu Ile Gly Trp Val Lys Gln Gly Asp Val Ile Tyr Asn Asn Ala Lys
        675                 680                 685
Ser Pro Val Asn Val Met Gln Thr Tyr Thr Val Lys Pro Gly Thr Lys
    690                 695                 700
Leu Tyr Ser Val Pro Trp Gly Thr Tyr Lys Gln Glu Ala Gly Ala Val
705                 710                 715                 720
Ser Gly Thr Gly Asn Gln Thr Phe Lys Ala Thr Lys Gln Gln Gln Ile
                725                 730                 735
Asp Lys Ser Ile Tyr Leu Tyr Gly Thr Val Asn Gly Lys Ser Gly Trp
            740                 745                 750
Ile Ser Lys Ala Tyr Leu Ala Val Pro Ala Ala Pro Lys Lys Ala Val
        755                 760                 765
Ala Gln Pro Lys Thr Ala Val Lys Ala Tyr Ala Val Thr Lys Pro Gln
    770                 775                 780
```

```
Thr Thr Gln Thr Val Ser Lys Ile Ala Gln Val Lys Pro Asn Asn Thr
785                 790                 795                 800

Gly Ile Arg Ala Ser Val Tyr Glu Lys Thr Ala Lys Asn Gly Ala Lys
            805                 810                 815

Tyr Ala Asp Arg Thr Phe Tyr Val Thr Lys Glu Arg Ala His Gly Asn
        820                 825                 830

Glu Thr Tyr Val Leu Leu Asn Asn Thr Ser His Asn Ile Pro Leu Gly
            835                 840                 845

Trp Phe Asn Val Lys Asp Leu Asn Val Gln Asn Leu Gly Lys Glu Val
        850                 855                 860

Lys Thr Thr Gln Lys Tyr Thr Val Asn Arg Ser Asn Asn Gly Leu Ser
865                 870                 875                 880

Met Val Pro Trp Gly Thr Lys Asn Gln Val Ile Leu Thr Gly Asn Asn
            885                 890                 895

Ile Ala Gln Gly Thr Phe Asn Ala Thr Lys Gln Val Ser Val Gly Lys
                900                 905                 910

Asp Val Tyr Leu Tyr Gly Thr Ile Asn Asn Arg Thr Gly Trp Val Asn
            915                 920                 925

Ser Lys Asp Leu Thr Ala Pro Thr Ala Val Lys Pro Thr Thr Ser Ala
930                 935                 940

Ala Lys Asp Tyr Asn Tyr Thr Tyr Val Ile Lys Asn Gly Asn Gly Tyr
945                 950                 955                 960

Tyr Tyr Val Thr Pro Asn Ser Asp Thr Ala Lys Tyr Ser Leu Lys Ala
            965                 970                 975

Phe Asn Glu Gln Pro Phe Ala Val Lys Glu Gln Val Ile Asn Gly
            980                 985                 990

Gln Thr Trp Tyr Tyr Gly Lys Leu Ser Asn Gly Lys Leu Ala Trp Ile
            995                 1000                1005

Lys Ser Thr Asp Leu Ala Lys Glu Leu Ile Lys Tyr Asn Gln Ile
    1010                1015                1020

Gly Met Thr Leu Asn Gln Val Ala Gln Ile Gln Ala Gly Leu Gln
    1025                1030                1035

Tyr Lys Pro Gln Val Gln Arg Val Pro Gly Lys Trp Thr Asp Ala
    1040                1045                1050

Asn Phe Asn Asp Val Lys His Ala Met Asp Thr Lys Arg Leu Ala
    1055                1060                1065

Gln Asp Pro Ala Leu Lys Tyr Gln Phe Leu Arg Leu Asp Gln Pro
    1070                1075                1080

Gln Asn Ile Ser Ile Asp Lys Ile Asn Gln Phe Leu Lys Gly Lys
    1085                1090                1095

Gly Val Leu Glu Asn Gln Gly Ala Ala Phe Asn Lys Ala Ala Gln
    1100                1105                1110

Met Tyr Gly Ile Asn Glu Val Tyr Leu Ile Ser His Ala Leu Leu
    1115                1120                1125

Glu Thr Gly Asn Gly Thr Ser Gln Leu Ala Lys Gly Ala Asp Val
    1130                1135                1140

Val Asn Asn Lys Val Val Thr Asn Ser Asn Thr Lys Tyr His Asn
    1145                1150                1155

Val Phe Gly Ile Ala Ala Tyr Asp Asn Asp Pro Leu Arg Glu Gly
    1160                1165                1170

Ile Lys Tyr Ala Lys Gln Ala Gly Trp Asp Thr Val Ser Lys Ala
    1175                1180                1185

Ile Val Gly Gly Ala Lys Phe Ile Gly Asn Ser Tyr Val Lys Ala
```

```
                1190                1195                1200

Gly Gln Asn Thr Leu Tyr Lys Met Arg Trp Asn Pro Ala His Pro
        1205                1210                1215

Gly Thr His Gln Tyr Ala Thr Asp Val Asp Trp Ala Asn Ile Asn
        1220                1225                1230

Ala Lys Ile Ile Lys Gly Tyr Tyr Asp Lys Ile Gly Glu Val Gly
        1235                1240                1245

Lys Tyr Phe Asp Ile Pro Gln Tyr Lys
        1250                1255

<210> SEQ ID NO 4
<211> LENGTH: 395
<212> TYPE: PRT
<213> ORGANISM: Staphylococcus simulans

<400> SEQUENCE: 4

Ala Asn Gln Val Gln Pro Leu Asn Lys Tyr Pro Val Val Phe Val His
1               5                   10                  15

Gly Phe Leu Gly Leu Val Gly Asp Asn Ala Pro Ala Leu Tyr Pro Asn
            20                  25                  30

Tyr Trp Gly Gly Asn Lys Phe Lys Val Ile Glu Glu Leu Arg Lys Gln
        35                  40                  45

Gly Tyr Asn Val His Gln Ala Ser Val Ser Ala Phe Gly Ser Asn Tyr
    50                  55                  60

Asp Arg Ala Val Glu Leu Tyr Tyr Ile Lys Gly Gly Arg Val Asp
65              70                  75                  80

Tyr Gly Ala Ala His Ala Ala Lys Tyr Gly His Glu Arg Tyr Gly Lys
                85                  90                  95

Thr Tyr Lys Gly Ile Met Pro Asn Trp Glu Pro Gly Lys Lys Val His
            100                 105                 110

Leu Val Gly His Ser Met Gly Gly Gln Thr Ile Arg Leu Met Glu Glu
        115                 120                 125

Phe Leu Arg Asn Gly Asn Lys Glu Glu Ile Ala Tyr His Lys Ala His
    130                 135                 140

Gly Gly Glu Ile Ser Pro Leu Phe Thr Gly Gly His Asn Asn Met Val
145             150                 155                 160

Ala Ser Ile Thr Thr Leu Ala Thr Pro His Asn Gly Ser Gln Ala Ala
                165                 170                 175

Asp Lys Phe Gly Asn Thr Glu Ala Val Arg Lys Ile Met Phe Ala Leu
            180                 185                 190

Asn Arg Phe Met Gly Asn Lys Tyr Ser Asn Ile Asp Leu Gly Leu Thr
        195                 200                 205

Gln Trp Gly Phe Lys Gln Leu Pro Asn Glu Ser Tyr Ile Asp Tyr Ile
    210                 215                 220

Lys Arg Val Ser Lys Ser Lys Ile Trp Thr Ser Asp Asp Asn Ala Ala
225             230                 235                 240

Tyr Asp Leu Thr Leu Asp Gly Ser Ala Lys Leu Asn Asn Met Thr Ser
                245                 250                 255

Met Asn Pro Asn Ile Thr Tyr Thr Thr Tyr Thr Gly Val Ser Ser His
            260                 265                 270

Thr Gly Pro Leu Gly Tyr Glu Asn Pro Asp Leu Gly Thr Phe Phe Leu
        275                 280                 285

Met Asp Thr Thr Ser Arg Ile Ile Gly His Asp Ala Arg Glu Glu Trp
    290                 295                 300

Arg Lys Asn Asp Gly Val Val Pro Val Ile Ser Ser Leu His Pro Ser
```

```
            305                 310                 315                 320
Asn Gln Pro Phe Val Asn Val Thr Asn Asp Glu Pro Ala Thr Arg Arg
                325                 330                 335

Gly Ile Trp Gln Val Lys Pro Ile Ile Gln Gly Trp Asp His Val Asp
                340                 345                 350

Phe Ile Gly Val Asp Phe Leu Asp Phe Lys Arg Lys Gly Ala Glu Leu
                355                 360                 365

Ala Asn Phe Tyr Thr Gly Ile Ile Asn Asp Leu Leu Arg Val Glu Ala
                370                 375                 380

Thr Glu Ser Lys Gly Thr Gln Leu Lys Ala Ser
385                 390                 395

<210> SEQ ID NO 5
<211> LENGTH: 319
<212> TYPE: PRT
<213> ORGANISM: Staphylococcus aureus

<400> SEQUENCE: 5

Met Lys Thr Arg Ile Val Ser Ser Val Thr Thr Leu Leu Leu Leu Gly
1               5                   10                  15

Ser Ile Leu Met Asn Pro Val Ala Ala Ala Asp Ser Asp Ile Asn
                20                  25                  30

Ile Lys Thr Gly Thr Thr Asp Ile Gly Ser Asn Thr Thr Val Lys Thr
                35                  40                  45

Gly Asp Leu Val Thr Tyr Asp Lys Glu Asn Gly Met His Lys Lys Val
            50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
                100                 105                 110

Gln Leu Gln Leu Pro Asp Asn Glu Val Ala Gln Ile Ser Asp Tyr Tyr
            115                 120                 125

Pro Arg Asn Ser Ile Asp Thr Lys Glu Tyr Met Ser Thr Leu Thr Tyr
        130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Glu Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Thr Asp Arg Ser
```

```
                  290                 295                 300
Ser Glu Arg Tyr Lys Ile Asp Trp Glu Lys Glu Met Thr Asn
305                 310                 315

<210> SEQ ID NO 6
<211> LENGTH: 943
<212> TYPE: PRT
<213> ORGANISM: Staphylococcus aureus

<400> SEQUENCE: 6

Met Leu Gly Val Ile Asn Arg Met Ala Lys Lys Phe Asn Tyr Lys Leu
1               5                   10                  15

Pro Ser Met Val Ala Leu Thr Leu Val Gly Ser Ala Val Thr Ala His
                20                  25                  30

Gln Val Gln Ala Ala Glu Thr Thr Gln Asp Gln Thr Thr Asn Lys Asn
            35                  40                  45

Val Leu Asp Ser Asn Lys Val Lys Ala Thr Thr Glu Gln Ala Lys Ala
50                  55                  60

Glu Val Lys Asn Pro Thr Gln Asn Ile Ser Gly Thr Gln Val Tyr Gln
65                  70                  75                  80

Asp Pro Ala Ile Val Gln Pro Lys Thr Ala Asn Asn Lys Thr Gly Asn
                85                  90                  95

Ala Gln Val Ser Gln Lys Val Asp Thr Ala Gln Val Asn Gly Asp Thr
            100                 105                 110

Arg Ala Asn Gln Ser Ala Thr Thr Asn Asn Thr Gln Pro Val Ala Lys
        115                 120                 125

Ser Thr Ser Thr Thr Ala Pro Lys Thr Asn Thr Asn Val Thr Asn Ala
130                 135                 140

Gly Tyr Ser Leu Val Asp Asp Glu Asp Asn Ser Glu His Gln Ile
145                 150                 155                 160

Asn Pro Glu Leu Ile Lys Ser Ala Ala Lys Pro Ala Ala Leu Glu Thr
                165                 170                 175

Gln Tyr Lys Ala Ala Ala Pro Lys Ala Lys Thr Glu Ala Thr Pro Lys
            180                 185                 190

Val Thr Thr Phe Ser Ala Ser Ala Gln Pro Arg Ser Val Ala Ala Thr
        195                 200                 205

Pro Lys Thr Ser Leu Pro Lys Tyr Lys Pro Gln Val Asn Ser Ser Ile
210                 215                 220

Asn Asp Tyr Ile Arg Lys Asn Asn Leu Lys Ala Pro Lys Ile Glu Glu
225                 230                 235                 240

Asp Tyr Thr Ser Tyr Phe Pro Lys Tyr Ala Tyr Arg Asn Gly Val Gly
                245                 250                 255

Arg Pro Glu Gly Ile Val Val His Asp Thr Ala Asn Asp Arg Ser Thr
            260                 265                 270

Ile Asn Gly Glu Ile Ser Tyr Met Lys Asn Asn Tyr Gln Asn Ala Phe
        275                 280                 285

Val His Ala Phe Val Asp Gly Asp Arg Ile Ile Glu Thr Ala Pro Thr
290                 295                 300

Asp Tyr Leu Ser Trp Gly Val Gly Ala Val Gly Asn Pro Arg Phe Ile
305                 310                 315                 320

Asn Val Glu Ile Val His Thr His Asp Tyr Ala Ser Phe Ala Arg Ser
                325                 330                 335

Met Asn Asn Tyr Ala Asp Tyr Ala Ala Thr Gln Leu Gln Tyr Tyr Gly
            340                 345                 350

Leu Lys Pro Asp Ser Ala Glu Tyr Asp Gly Asn Gly Thr Val Trp Thr
```

```
              355                 360                 365
His Tyr Ala Val Ser Lys Tyr Leu Gly Gly Thr Asp His Ala Asp Pro
370                 375                 380
His Gly Tyr Leu Arg Ser His Asn Tyr Ser Tyr Asp Gln Leu Tyr Asp
385                 390                 395                 400
Leu Ile Asn Glu Lys Tyr Leu Ile Lys Met Gly Lys Val Ala Pro Trp
                405                 410                 415
Gly Thr Gln Phe Thr Thr Thr Pro Thr Pro Ser Lys Pro Thr Thr
                420                 425                 430
Pro Ser Lys Pro Ser Thr Gly Lys Leu Thr Val Ala Ala Asn Asn Gly
            435                 440                 445
Val Ala Gln Ile Lys Pro Thr Asn Ser Gly Leu Tyr Thr Thr Val Tyr
        450                 455                 460
Asp Lys Thr Gly Lys Ala Thr Asn Glu Val Gln Lys Thr Phe Ala Val
465                 470                 475                 480
Ser Lys Thr Ala Thr Leu Gly Asn Gln Lys Phe Tyr Leu Val Gln Asp
                485                 490                 495
Tyr Asn Ser Gly Asn Lys Phe Gly Trp Val Lys Glu Gly Asp Val Val
                500                 505                 510
Tyr Asn Thr Ala Lys Ser Pro Val Asn Val Asn Gln Ser Tyr Ser Ile
            515                 520                 525
Lys Ser Gly Thr Lys Leu Tyr Thr Val Pro Trp Gly Thr Ser Lys Gln
        530                 535                 540
Val Ala Gly Ser Val Ser Gly Ser Gly Asn Gln Thr Phe Lys Ala Ser
545                 550                 555                 560
Lys Gln Gln Gln Ile Asp Lys Ser Ile Tyr Leu Tyr Gly Ser Val Asn
                565                 570                 575
Gly Lys Ser Gly Trp Val Ser Lys Ala Tyr Leu Val Asp Thr Ala Lys
                580                 585                 590
Pro Thr Pro Thr Pro Ile Pro Lys Pro Ser Thr Pro Thr Thr Asn Asn
            595                 600                 605
Lys Leu Thr Val Ser Ser Leu Asn Gly Val Ala Gln Ile Asn Ala Lys
        610                 615                 620
Asn Asn Gly Leu Phe Thr Thr Val Tyr Asp Lys Thr Gly Lys Pro Thr
625                 630                 635                 640
Lys Glu Val Gln Lys Thr Phe Ala Val Thr Lys Glu Ala Ser Leu Gly
                645                 650                 655
Gly Asn Lys Phe Tyr Leu Val Lys Asp Tyr Asn Ser Pro Thr Leu Ile
                660                 665                 670
Gly Trp Val Lys Gln Gly Asp Val Ile Tyr Asn Asn Ala Lys Ser Pro
            675                 680                 685
Val Asn Val Met Gln Thr Tyr Thr Val Lys Pro Gly Thr Lys Leu Tyr
        690                 695                 700
Ser Val Pro Trp Gly Thr Tyr Lys Gln Glu Ala Gly Ala Val Ser Gly
705                 710                 715                 720
Thr Gly Asn Gln Thr Phe Lys Ala Thr Lys Gln Gln Ile Asp Lys
                725                 730                 735
Ser Ile Tyr Leu Phe Gly Thr Val Asn Gly Lys Ser Gly Trp Val Ser
                740                 745                 750
Lys Ala Tyr Leu Ala Val Pro Ala Ala Pro Lys Lys Ala Val Ala Gln
            755                 760                 765
Pro Lys Thr Ala Val Lys Ala Tyr Thr Val Thr Lys Pro Gln Thr Thr
        770                 775                 780
```

```
Gln Thr Val Ser Lys Ile Ala Gln Val Lys Pro Asn Asn Thr Gly Ile
785                 790                 795                 800

Arg Ala Ser Val Tyr Glu Lys Thr Ala Lys Asn Gly Ala Lys Tyr Ala
            805                 810                 815

Asp Arg Thr Phe Tyr Val Thr Lys Glu Arg Ala His Gly Asn Glu Thr
        820                 825                 830

Tyr Val Leu Leu Asn Asn Thr Ser His Asn Ile Pro Leu Gly Trp Phe
    835                 840                 845

Asn Val Lys Asp Leu Asn Val Gln Asn Leu Gly Lys Glu Val Lys Thr
850                 855                 860

Thr Gln Lys Tyr Thr Val Asn Lys Ser Asn Asn Gly Leu Ser Met Val
865                 870                 875                 880

Pro Trp Gly Thr Lys Asn Gln Val Ile Leu Thr Gly Asn Asn Ile Ala
                885                 890                 895

Gln Gly Thr Phe Asn Ala Thr Lys Gln Val Ser Val Gly Lys Asp Val
                900                 905                 910

Tyr Tyr Thr Val Leu Leu Ile Thr Ala Leu Val Gly Lys Ala Lys Asp
                915                 920                 925

Leu Pro His Gln Leu Gly Asn Gln Leu His Gln Leu Pro Lys Ile
930                 935                 940

<210> SEQ ID NO 7
<211> LENGTH: 166
<212> TYPE: PRT
<213> ORGANISM: Staphylococcus aureus

<400> SEQUENCE: 7

Met Ile Thr Tyr Lys Asn Ile Leu Ile Ala Val Asp Gly Ser His Glu
1               5                   10                  15

Ala Glu Trp Ala Phe Asn Arg Ala Val Gly Val Ala Lys Arg Asn Asp
            20                  25                  30

Ala Lys Leu Thr Ile Val Asn Val Ile Asp Ser Arg Thr Tyr Ser Ser
        35                  40                  45

Tyr Glu Val Tyr Asp Ala Gln Phe Thr Glu Lys Ser Lys His Phe Ala
    50                  55                  60

Glu Glu Leu Leu Asn Gly Tyr Lys Glu Val Ala Thr Asn Ala Gly Val
65                  70                  75                  80

Lys Asp Val Glu Thr Arg Leu Glu Phe Gly Ser Pro Lys Ser Ile Ile
                85                  90                  95

Pro Lys Lys Leu Ala His Glu Ile Asn Ala Asp Leu Ile Met Ser Gly
                100                 105                 110

Thr Ser Gly Leu Asn Ala Val Glu Arg Phe Ile Val Gly Ser Val Ser
            115                 120                 125

Glu Ser Ile Val Arg His Ala Pro Cys Asp Val Leu Val Val Arg Thr
130                 135                 140

Glu Glu Leu Pro Ala Asp Phe Gln Pro Gln Val Ala Thr Thr Gln Leu
145                 150                 155                 160

Arg Glu Lys Tyr Gln Asn
            165

<210> SEQ ID NO 8
<211> LENGTH: 199
<212> TYPE: PRT
<213> ORGANISM: Staphylococcus aureus

<400> SEQUENCE: 8

Met Ala Phe Glu Leu Pro Lys Leu Pro Tyr Ala Phe Asp Ala Leu Glu
```

```
           1               5                  10                 15
Pro His Phe Asp Lys Glu Thr Met Glu Ile His His Asp Arg His His
                    20                  25                 30

Asn Thr Tyr Val Thr Lys Leu Asn Ala Ala Val Glu Gly Thr Asp Leu
                35                  40                  45

Glu Ser Lys Ser Ile Glu Ile Val Ala Asn Leu Asp Ser Val Pro
            50                  55                  60

Ala Asn Ile Gln Thr Ala Val Arg Asn Asn Gly Gly His Leu Asn
65                  70                  75                  80

His Ser Leu Phe Trp Glu Leu Leu Ser Pro Asn Ser Glu Glu Lys Gly
                    85                  90                  95

Thr Val Val Glu Lys Ile Lys Glu Gln Trp Gly Ser Leu Glu Glu Phe
                100                 105                 110

Lys Lys Glu Phe Ala Asp Lys Ala Ala Arg Phe Gly Ser Gly Trp
            115                 120                 125

Ala Trp Leu Val Val Asn Asn Gly Gln Leu Glu Ile Val Thr Thr Pro
            130                 135                 140

Asn Gln Asp Asn Pro Leu Thr Glu Gly Lys Thr Pro Ile Leu Gly Leu
145                 150                 155                 160

Asp Val Trp Glu His Ala Tyr Tyr Leu Lys Tyr Gln Asn Lys Arg Pro
                165                 170                 175

Asp Tyr Ile Gly Ala Phe Trp Asn Val Val Asn Trp Glu Lys Val Asp
                180                 185                 190

Glu Leu Tyr Asn Ala Thr Lys
            195

<210> SEQ ID NO 9
<211> LENGTH: 228
<212> TYPE: PRT
<213> ORGANISM: Staphylococcus aureus

<400> SEQUENCE: 9

Met Pro Lys Leu Ile Leu Cys Arg His Gly Gln Ser Glu Trp Asn Ala
1               5                  10                  15

Lys Asn Leu Phe Thr Gly Trp Glu Asp Val Asn Leu Ser Glu Gln Gly
                20                  25                  30

Ile Asn Glu Ala Thr Arg Ala Gly Glu Lys Val Arg Glu Asn Asn Ile
            35                  40                  45

Ala Ile Asp Val Ala Phe Thr Ser Leu Leu Thr Arg Ala Leu Asp Thr
50                  55                  60

Thr His Tyr Ile Leu Thr Glu Ser Lys Gln Gln Trp Ile Pro Val Tyr
65                  70                  75                  80

Lys Ser Trp Arg Leu Asn Glu Arg His Tyr Gly Gly Leu Gln Gly Leu
                85                  90                  95

Asn Lys Asp Asp Ala Arg Lys Glu Phe Gly Glu Glu Gln Val His Ile
            100                 105                 110

Trp Arg Arg Ser Tyr Asp Val Lys Pro Pro Ala Glu Thr Glu Glu Gln
            115                 120                 125

Arg Glu Ala Tyr Leu Ala Asp Arg Arg Tyr Asn His Leu Asp Lys Arg
            130                 135                 140

Met Met Pro Tyr Ser Glu Ser Leu Lys Asp Thr Leu Val Arg Val Ile
145                 150                 155                 160

Pro Phe Trp Thr Asp His Ile Ser Gln Tyr Leu Leu Asp Gly Gln Thr
                165                 170                 175

Val Leu Val Ser Ala His Gly Asn Ser Ile Arg Ala Leu Ile Lys Tyr
```

```
                            180                 185                 190
Leu Glu Asp Val Ser Asp Glu Asp Ile Ile Asn Tyr Glu Ile Lys Thr
                195                 200                 205

Gly Ala Pro Leu Val Tyr Glu Leu Thr Asp Asp Leu Glu Val Ile Asp
    210                 215                 220

Lys Tyr Tyr Leu
225

<210> SEQ ID NO 10
<211> LENGTH: 189
<212> TYPE: PRT
<213> ORGANISM: Staphylococcus aureus

<400> SEQUENCE: 10

Met Ser Leu Ile Asn Lys Glu Ile Leu Pro Phe Thr Ala Gln Ala Phe
1               5                   10                  15

Asp Pro Lys Lys Asp Gln Phe Lys Glu Val Thr Gln Glu Asp Leu Lys
            20                  25                  30

Gly Ser Trp Ser Val Val Cys Phe Tyr Pro Ala Asp Phe Ser Phe Val
        35                  40                  45

Cys Pro Thr Glu Leu Glu Asp Leu Gln Asn Gln Tyr Glu Glu Leu Gln
    50                  55                  60

Lys Leu Gly Val Asn Val Phe Ser Val Ser Thr Asp Thr His Phe Val
65                  70                  75                  80

His Lys Ala Trp His Asp His Ser Asp Ala Ile Ser Lys Ile Thr Tyr
                85                  90                  95

Thr Met Ile Gly Asp Pro Ser Gln Thr Ile Thr Arg Asn Phe Asp Val
            100                 105                 110

Leu Asp Glu Ala Thr Gly Leu Ala Gln Arg Gly Thr Phe Ile Ile Asp
        115                 120                 125

Pro Asp Gly Val Val Gln Ala Ser Glu Ile Asn Ala Asp Gly Ile Gly
    130                 135                 140

Arg Asp Ala Ser Thr Leu Ala His Lys Ile Lys Ala Ala Gln Tyr Val
145                 150                 155                 160

Arg Lys Asn Pro Gly Glu Val Cys Pro Ala Lys Trp Glu Glu Gly Ala
                165                 170                 175

Lys Thr Leu Gln Pro Gly Leu Asp Leu Val Gly Lys Ile
            180                 185

<210> SEQ ID NO 11
<211> LENGTH: 446
<212> TYPE: PRT
<213> ORGANISM: Staphylococcus aureus

<400> SEQUENCE: 11

Met Pro Lys Arg Thr Phe Thr Lys Asp Asp Ile Arg Lys Phe Ala Glu
1               5                   10                  15

Glu Glu Asn Val Arg Tyr Leu Arg Leu Gln Phe Thr Asp Ile Leu Gly
            20                  25                  30

Thr Ile Lys Asn Val Glu Val Pro Val Ser Gln Leu Glu Lys Val Leu
        35                  40                  45

Asp Asn Glu Met Met Phe Asp Gly Ser Ser Ile Glu Gly Phe Val Arg
    50                  55                  60

Ile Glu Glu Ser Asp Met Tyr Leu His Pro Asp Leu Asp Thr Trp Val
65                  70                  75                  80

Ile Phe Pro Trp Thr Ala Gly Gln Gly Lys Val Ala Arg Leu Ile Cys
                85                  90                  95
```

Asp Val Tyr Lys Thr Asp Gly Thr Pro Phe Glu Gly Asp Pro Arg Ala
            100                 105                 110

Asn Leu Lys Arg Val Leu Lys Glu Met Glu Asp Leu Gly Phe Thr Asp
        115                 120                 125

Phe Asn Leu Gly Pro Glu Pro Glu Phe Leu Phe Lys Leu Asp Glu
    130                 135                 140

Lys Gly Glu Pro Thr Leu Glu Leu Asn Asp Asp Gly Gly Tyr Phe Asp
145                 150                 155                 160

Leu Ala Pro Thr Asp Leu Gly Glu Asn Cys Arg Arg Asp Ile Val Leu
                165                 170                 175

Glu Leu Glu Asp Met Gly Phe Asp Ile Glu Ala Ser His His Glu Val
            180                 185                 190

Ala Pro Gly Gln His Glu Ile Asp Phe Lys Tyr Ala Asp Ala Val Thr
        195                 200                 205

Ala Cys Asp Asn Ile Gln Thr Phe Lys Leu Val Val Lys Thr Ile Ala
    210                 215                 220

Arg Lys His Asn Leu His Ala Thr Phe Met Pro Lys Pro Leu Phe Gly
225                 230                 235                 240

Val Asn Gly Ser Gly Met His Phe Asn Val Ser Leu Phe Lys Gly Lys
                245                 250                 255

Glu Asn Ala Phe Phe Asp Pro Asn Thr Glu Met Gly Leu Thr Glu Thr
            260                 265                 270

Ala Tyr Gln Phe Thr Ala Gly Val Leu Lys Asn Ala Arg Gly Phe Thr
        275                 280                 285

Ala Val Cys Asn Pro Leu Val Asn Ser Tyr Lys Arg Leu Val Pro Gly
    290                 295                 300

Tyr Glu Ala Pro Cys Tyr Ile Ala Trp Ser Gly Lys Asn Arg Ser Pro
305                 310                 315                 320

Leu Ile Arg Val Pro Ser Ser Arg Gly Leu Ser Thr Arg Ile Glu Val
                325                 330                 335

Arg Ser Val Asp Pro Ala Ala Asn Pro Tyr Met Ala Leu Ala Ala Ile
            340                 345                 350

Leu Glu Ala Gly Leu Asp Gly Ile Lys Asn Lys Leu Lys Val Pro Glu
        355                 360                 365

Pro Val Asn Gln Asn Ile Tyr Glu Met Asn Arg Glu Glu Arg Glu Ala
    370                 375                 380

Val Gly Ile Gln Asp Leu Pro Ser Thr Leu Tyr Thr Ala Leu Lys Ala
385                 390                 395                 400

Met Arg Glu Asn Glu Val Ile Lys Lys Ala Leu Gly Asn His Ile Tyr
                405                 410                 415

Asn Gln Phe Ile Asn Ser Lys Ser Ile Glu Trp Asp Tyr Tyr Arg Thr
            420                 425                 430

Gln Val Ser Glu Trp Glu Arg Asp Gln Tyr Met Lys Gln Tyr
        435                 440                 445

<210> SEQ ID NO 12
<211> LENGTH: 195
<212> TYPE: PRT
<213> ORGANISM: Staphylococcus aureus

<400> SEQUENCE: 12

Met Asn Leu Ile Pro Thr Val Ile Glu Thr Thr Asn Arg Gly Glu Arg
1               5                   10                  15

Ala Tyr Asp Ile Tyr Ser Arg Leu Leu Lys Asp Arg Ile Ile Met Leu
            20                  25                  30

Gly Ser Gln Ile Asp Asp Asn Val Ala Asn Ser Ile Val Ser Gln Leu
                35                  40                  45

Leu Phe Leu Gln Ala Gln Asp Ser Glu Lys Asp Ile Tyr Leu Tyr Ile
 50                  55                  60

Asn Ser Pro Gly Gly Ser Val Thr Ala Gly Phe Ala Ile Tyr Asp Thr
 65                  70                  75                  80

Ile Gln His Ile Lys Pro Asp Val Gln Thr Ile Cys Ile Gly Met Ala
                 85                  90                  95

Ala Ser Met Gly Ser Phe Leu Leu Ala Ala Gly Ala Lys Gly Lys Arg
                100                 105                 110

Phe Ala Leu Pro Asn Ala Glu Val Met Ile His Gln Pro Leu Gly Gly
                115                 120                 125

Ala Gln Gly Gln Ala Thr Glu Ile Glu Ile Ala Ala Asn His Ile Leu
        130                 135                 140

Lys Thr Arg Glu Lys Leu Asn Arg Ile Leu Ser Glu Arg Thr Gly Gln
145                 150                 155                 160

Ser Ile Glu Lys Ile Gln Lys Asp Thr Asp Arg Asp Asn Phe Leu Thr
                165                 170                 175

Ala Glu Glu Ala Lys Glu Tyr Gly Leu Ile Asp Glu Val Met Val Pro
                180                 185                 190

Glu Thr Lys
        195

<210> SEQ ID NO 13
<211> LENGTH: 309
<212> TYPE: PRT
<213> ORGANISM: Staphylococcus aureus

<400> SEQUENCE: 13

Met Lys Lys Leu Val Pro Leu Leu Ala Leu Leu Leu Leu Val Ala
 1               5                  10                  15

Ala Cys Gly Thr Gly Gly Lys Gln Ser Ser Asp Lys Ser Asn Gly Lys
                 20                  25                  30

Leu Lys Val Val Thr Thr Asn Ser Ile Leu Tyr Asp Met Ala Lys Asn
                35                  40                  45

Val Gly Gly Asp Asn Val Asp Ile His Ser Ile Val Pro Val Gly Gln
 50                  55                  60

Asp Pro His Glu Tyr Glu Val Lys Pro Lys Asp Ile Lys Lys Leu Thr
 65                  70                  75                  80

Asp Ala Asp Val Ile Leu Tyr Asn Gly Leu Asn Leu Glu Thr Gly Asn
                 85                  90                  95

Gly Trp Phe Glu Lys Ala Leu Glu Gln Ala Gly Lys Ser Leu Lys Asp
                100                 105                 110

Lys Lys Val Ile Ala Val Ser Lys Asp Val Lys Pro Ile Tyr Leu Asn
                115                 120                 125

Gly Glu Glu Gly Asn Lys Asp Lys Gln Asp Pro His Ala Trp Leu Ser
        130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
                180                 185                 190

Asn Asp Ile Pro Lys Glu Gln Arg Ala Met Ile Thr Ser Glu Gly Ala
                195                 200                 205

```
Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
                260                 265                 270

Asp Ile Phe Gly Glu Val Tyr Thr Asp Ser Ile Gly Lys Glu Gly Thr
            275                 280                 285

Lys Gly Asp Ser Tyr Tyr Lys Met Met Lys Ser Asn Ile Glu Thr Val
    290                 295                 300

His Gly Ser Met Lys
305

<210> SEQ ID NO 14
<211> LENGTH: 681
<212> TYPE: PRT
<213> ORGANISM: Staphylococcus aureus

<400> SEQUENCE: 14

Met Met Lys Ser Gln Asn Lys Tyr Ser Ile Arg Lys Phe Ser Val Gly
1               5                   10                  15

Ala Ser Ser Ile Leu Ile Ala Thr Leu Phe Leu Ser Gly Gly Gln
                20                  25                  30

Ala Gln Ala Ala Glu Lys Gln Val Asn Met Gly Asn Ser Gln Glu Asp
            35                  40                  45

Thr Val Thr Ala Gln Ser Ile Gly Asp Gln Gln Thr Arg Glu Asn Ala
    50                  55                  60

Asn Tyr Gln Arg Glu Asn Gly Val Asp Glu Gln His Thr Glu Asn
65                  70                  75                  80

Leu Thr Lys Asn Leu His Asn Asp Lys Thr Ile Ser Glu Glu Asn His
                85                  90                  95

Arg Lys Thr Asp Asp Leu Asn Lys Asp Gln Leu Lys Asp Asp Lys Asn
            100                 105                 110

Ser Ser Leu Asn Asn Lys Asn Ile Gln Arg Asp Thr Thr Lys Asn Asn
        115                 120                 125

Asn Ala Asn Pro Ser Asp Val Asn Gln Gly Leu Glu Gln Ala Ile Asn
    130                 135                 140

Asp Gly Lys Gln Ser Lys Val Ala Ser Gln Gln Ser Lys Glu Val
145                 150                 155                 160

Asp Asn Ser Gln Asp Ser Asn Ala Asn Asn Leu Pro Ser Gln Ser
                165                 170                 175

Leu Thr Lys Glu Ala Pro Ser Leu Asn Lys Ser Asp Gln Thr Ser Gln
            180                 185                 190

Arg Glu Ile Val Asn Glu Thr Glu Ile Glu Lys Val Gln Pro Gln Gln
        195                 200                 205

Asn Asn Gln Ala Asn Asp Lys Ile Thr Asn His Asn Phe Asn Glu
    210                 215                 220

Gln Glu Val Lys Pro Gln Lys Asp Glu Lys Thr Leu Ser Val Ser Asp
225                 230                 235                 240

Leu Lys Asn Asn Gln Lys Ser Pro Val Glu Pro Thr Lys Asp Asn Asp
                245                 250                 255

Lys Lys Asn Gly Leu Asn Leu Leu Lys Ser Ser Ala Val Ala Thr Leu
            260                 265                 270
```

```
Pro Asn Lys Gly Thr Lys Glu Leu Thr Ala Lys Ala Lys Asp Asp Gln
        275                 280                 285

Thr Asn Lys Val Ala Lys Gln Gly Gln Tyr Lys Asn Gln Asp Pro Ile
    290                 295                 300

Val Leu Val His Gly Phe Asn Gly Phe Thr Asp Asp Ile Asn Pro Ser
305                 310                 315                 320

Val Leu Ala His Tyr Trp Gly Gly Asn Lys Met Asn Ile Arg Gln Asp
                325                 330                 335

Leu Glu Glu Asn Gly Tyr Lys Ala Tyr Glu Ala Ser Ile Ser Ala Phe
                340                 345                 350

Gly Ser Asn Tyr Asp Arg Ala Val Glu Leu Tyr Tyr Ile Lys Gly
        355                 360                 365

Gly Arg Val Asp Tyr Gly Ala Ala His Ala Ala Lys Tyr Gly His Glu
    370                 375                 380

Arg Tyr Gly Lys Thr Tyr Glu Gly Ile Tyr Lys Asp Trp Lys Pro Gly
385                 390                 395                 400

Gln Lys Val His Leu Val Gly His Ser Met Gly Gly Gln Thr Ile Arg
                405                 410                 415

Gln Leu Glu Glu Leu Leu Arg Asn Gly Asn Arg Glu Glu Ile Glu Tyr
                420                 425                 430

Gln Lys Lys His Gly Gly Glu Ile Ser Pro Leu Phe Lys Gly Asn Asn
        435                 440                 445

Asp Asn Met Ile Ser Ser Ile Thr Thr Leu Gly Thr Pro His Asn Gly
    450                 455                 460

Thr His Ala Ser Asp Leu Ala Gly Asn Glu Ala Leu Val Arg Gln Ile
465                 470                 475                 480

Val Phe Asp Ile Gly Lys Met Phe Gly Asn Lys Asn Ser Arg Val Asp
                485                 490                 495

Phe Gly Leu Ala Gln Trp Gly Leu Lys Gln Lys Pro Asn Glu Ser Tyr
                500                 505                 510

Ile Asp Tyr Val Lys Arg Val Lys Gln Ser Asn Leu Trp Lys Ser Lys
        515                 520                 525

Asp Asn Gly Phe Tyr Asp Leu Thr Arg Glu Gly Ala Thr Asp Leu Asn
    530                 535                 540

Arg Lys Thr Ser Leu Asn Pro Asn Ile Val Tyr Lys Thr Tyr Thr Gly
545                 550                 555                 560

Glu Ala Thr His Lys Ala Leu Asn Ser Asp Arg Gln Lys Ala Asp Leu
                565                 570                 575

Asn Met Phe Phe Pro Phe Val Ile Thr Gly Asn Leu Ile Gly Lys Ala
                580                 585                 590

Thr Glu Lys Glu Trp Arg Glu Asn Asp Gly Leu Val Ser Val Ile Ser
        595                 600                 605

Ser Gln His Pro Phe Asn Gln Ala Tyr Thr Asn Ala Thr Asp Lys Ile
    610                 615                 620

Gln Lys Gly Ile Trp Gln Val Thr Pro Thr Lys His Asp Trp Asp His
625                 630                 635                 640

Val Asp Phe Val Gly Gln Asp Ser Ser Asp Thr Val Arg Thr Arg Glu
                645                 650                 655

Glu Leu Gln Asp Phe Trp His His Leu Ala Asp Asp Leu Val Lys Thr
                660                 665                 670

Glu Lys Val Thr Asp Thr Lys Gln Ala
        675                 680
```

<210> SEQ ID NO 15
<211> LENGTH: 394
<212> TYPE: PRT
<213> ORGANISM: Staphylococcus aureus

<400> SEQUENCE: 15

| Met | Ala | Lys | Glu | Lys | Phe | Asp | Arg | Ser | Lys | Glu | His | Ala | Asn | Ile | Gly |
|---|---|---|---|---|---|---|---|---|---|---|---|---|---|---|---|
| 1 | | | | 5 | | | | | 10 | | | | | 15 | |

| Thr | Ile | Gly | His | Val | Asp | His | Gly | Lys | Thr | Thr | Leu | Thr | Ala | Ala | Ile |
|---|---|---|---|---|---|---|---|---|---|---|---|---|---|---|---|
| | | | 20 | | | | | 25 | | | | | 30 | | |

| Ala | Thr | Val | Leu | Ala | Lys | Asn | Gly | Asp | Ser | Val | Ala | Gln | Ser | Tyr | Asp |
|---|---|---|---|---|---|---|---|---|---|---|---|---|---|---|---|
| | | | 35 | | | | | 40 | | | | | 45 | | |

| Met | Ile | Asp | Asn | Ala | Pro | Glu | Glu | Lys | Glu | Arg | Gly | Ile | Thr | Ile | Asn |
|---|---|---|---|---|---|---|---|---|---|---|---|---|---|---|---|
| | 50 | | | | | 55 | | | | | 60 | | | | |

| Thr | Ser | His | Ile | Glu | Tyr | Gln | Thr | Asp | Lys | Arg | His | Tyr | Ala | His | Val |
|---|---|---|---|---|---|---|---|---|---|---|---|---|---|---|---|
| 65 | | | | | 70 | | | | | 75 | | | | | 80 |

| Asp | Cys | Pro | Gly | His | Ala | Asp | Tyr | Val | Lys | Asn | Met | Ile | Thr | Gly | Ala |
|---|---|---|---|---|---|---|---|---|---|---|---|---|---|---|---|
| | | | | 85 | | | | | 90 | | | | | 95 | |

| Ala | Gln | Met | Asp | Gly | Gly | Ile | Leu | Val | Val | Ser | Ala | Ala | Asp | Gly | Pro |
|---|---|---|---|---|---|---|---|---|---|---|---|---|---|---|---|
| | | | 100 | | | | | 105 | | | | | 110 | | |

| Met | Pro | Gln | Thr | Arg | Glu | His | Ile | Leu | Leu | Ser | Arg | Asn | Val | Gly | Val |
|---|---|---|---|---|---|---|---|---|---|---|---|---|---|---|---|
| | | | 115 | | | | | 120 | | | | | 125 | | |

| Pro | Ala | Leu | Val | Val | Phe | Leu | Asn | Lys | Val | Asp | Met | Val | Asp | Asp | Glu |
|---|---|---|---|---|---|---|---|---|---|---|---|---|---|---|---|
| 130 | | | | | 135 | | | | | 140 | | | | | |

| Glu | Leu | Leu | Glu | Leu | Val | Glu | Met | Glu | Val | Arg | Asp | Leu | Leu | Ser | Glu |
|---|---|---|---|---|---|---|---|---|---|---|---|---|---|---|---|
| 145 | | | | | 150 | | | | | 155 | | | | | 160 |

| Tyr | Asp | Phe | Pro | Gly | Asp | Asp | Val | Pro | Val | Ile | Ala | Gly | Ser | Ala | Leu |
|---|---|---|---|---|---|---|---|---|---|---|---|---|---|---|---|
| | | | | 165 | | | | | 170 | | | | | 175 | |

| Lys | Ala | Leu | Glu | Gly | Asp | Ala | Gln | Tyr | Glu | Glu | Lys | Ile | Leu | Glu | Leu |
|---|---|---|---|---|---|---|---|---|---|---|---|---|---|---|---|
| | | | 180 | | | | | 185 | | | | | 190 | | |

| Met | Glu | Ala | Val | Asp | Thr | Tyr | Ile | Pro | Thr | Pro | Glu | Arg | Asp | Ser | Asp |
|---|---|---|---|---|---|---|---|---|---|---|---|---|---|---|---|
| | | | 195 | | | | | 200 | | | | | 205 | | |

| Lys | Pro | Phe | Met | Met | Pro | Val | Glu | Asp | Val | Phe | Ser | Ile | Thr | Gly | Arg |
|---|---|---|---|---|---|---|---|---|---|---|---|---|---|---|---|
| | 210 | | | | | 215 | | | | | 220 | | | | |

| Gly | Thr | Val | Ala | Thr | Gly | Arg | Val | Glu | Arg | Gly | Gln | Ile | Lys | Val | Gly |
|---|---|---|---|---|---|---|---|---|---|---|---|---|---|---|---|
| 225 | | | | | 230 | | | | | 235 | | | | | 240 |

| Glu | Glu | Val | Glu | Ile | Ile | Gly | Leu | His | Asp | Thr | Ser | Lys | Thr | Thr | Val |
|---|---|---|---|---|---|---|---|---|---|---|---|---|---|---|---|
| | | | | 245 | | | | | 250 | | | | | 255 | |

| Thr | Gly | Val | Glu | Met | Phe | Arg | Lys | Leu | Leu | Asp | Tyr | Ala | Glu | Ala | Gly |
|---|---|---|---|---|---|---|---|---|---|---|---|---|---|---|---|
| | | | 260 | | | | | 265 | | | | | 270 | | |

| Asp | Asn | Ile | Gly | Ala | Leu | Leu | Arg | Gly | Val | Ala | Arg | Glu | Asp | Val | Gln |
|---|---|---|---|---|---|---|---|---|---|---|---|---|---|---|---|
| | 275 | | | | | 280 | | | | | 285 | | | | |

| Arg | Gly | Gln | Val | Leu | Ala | Ala | Pro | Gly | Ser | Ile | Thr | Pro | His | Thr | Glu |
|---|---|---|---|---|---|---|---|---|---|---|---|---|---|---|---|
| | 290 | | | | | 295 | | | | | 300 | | | | |

| Phe | Lys | Ala | Glu | Val | Tyr | Val | Leu | Ser | Lys | Asp | Glu | Gly | Gly | Arg | His |
|---|---|---|---|---|---|---|---|---|---|---|---|---|---|---|---|
| 305 | | | | | 310 | | | | | 315 | | | | | 320 |

| Thr | Pro | Phe | Phe | Ser | Asn | Tyr | Arg | Pro | Gln | Phe | Tyr | Phe | Arg | Thr | Thr |
|---|---|---|---|---|---|---|---|---|---|---|---|---|---|---|---|
| | | | | 325 | | | | | 330 | | | | | 335 | |

| Asp | Val | Thr | Gly | Val | Val | His | Leu | Pro | Glu | Gly | Thr | Glu | Met | Val | Met |
|---|---|---|---|---|---|---|---|---|---|---|---|---|---|---|---|
| | | | 340 | | | | | 345 | | | | | 350 | | |

| Pro | Gly | Asp | Asn | Val | Glu | Met | Thr | Val | Glu | Leu | Ile | Ala | Pro | Ile | Ala |
|---|---|---|---|---|---|---|---|---|---|---|---|---|---|---|---|
| | | | 355 | | | | | 360 | | | | | 365 | | |

| Ile | Glu | Asp | Gly | Thr | Arg | Phe | Ser | Ile | Arg | Glu | Gly | Gly | Arg | Thr | Val |
|---|---|---|---|---|---|---|---|---|---|---|---|---|---|---|---|
| | 370 | | | | | 375 | | | | | 380 | | | | |

| Gly | Ser | Gly | Val | Val | Thr | Glu | Ile | Ile | Lys |
|---|---|---|---|---|---|---|---|---|---|

385 390

<210> SEQ ID NO 16
<211> LENGTH: 662
<212> TYPE: PRT
<213> ORGANISM: Staphylococcus aureus

<400> SEQUENCE: 16

Met Phe Asn Glu Lys Asp Gln Leu Ala Val Asp Thr Leu Arg Ala Leu
1               5                   10                  15

Ser Ile Asp Thr Ile Glu Lys Ala Asn Ser Gly His Pro Gly Leu Pro
            20                  25                  30

Met Gly Ala Ala Pro Met Ala Tyr Thr Leu Trp Thr Arg His Leu Asn
        35                  40                  45

Phe Asn Pro Gln Ser Lys Asp Tyr Phe Asn Arg Asp Arg Phe Val Leu
    50                  55                  60

Ser Ala Gly His Gly Ser Ala Leu Leu Tyr Ser Leu Leu His Val Ser
65                  70                  75                  80

Gly Ser Leu Glu Leu Glu Glu Leu Lys Gln Phe Arg Gln Trp Gly Ser
                85                  90                  95

Lys Thr Pro Gly His Pro Glu Tyr Arg His Thr Asp Gly Val Glu Val
            100                 105                 110

Thr Thr Gly Pro Leu Gly Gln Gly Phe Ala Met Ser Val Gly Leu Ala
        115                 120                 125

Leu Ala Glu Asp His Leu Ala Gly Lys Phe Asn Lys Glu Gly Tyr Asn
    130                 135                 140

Val Val Asp His Tyr Thr Tyr Val Leu Ala Ser Asp Gly Asp Leu Met
145                 150                 155                 160

Glu Gly Ile Ser His Glu Ala Ala Ser Phe Ala Gly His Asn Lys Leu
                165                 170                 175

Ser Lys Leu Val Val Leu Tyr Asp Ser Asn Asp Ile Ser Leu Asp Gly
            180                 185                 190

Glu Leu Asn Lys Ala Phe Ser Glu Asn Thr Lys Ala Arg Phe Glu Ala
        195                 200                 205

Tyr Gly Trp Asn Tyr Leu Leu Val Lys Asp Gly Asn Asp Leu Glu Glu
    210                 215                 220

Ile Asp Lys Ala Ile Thr Thr Ala Lys Ser Gln Glu Gly Pro Thr Ile
225                 230                 235                 240

Ile Glu Val Lys Thr Thr Ile Gly Phe Gly Ser Pro Asn Lys Ala Gly
                245                 250                 255

Thr Asn Gly Val His Gly Ala Pro Leu Gly Glu Val Glu Arg Lys Leu
            260                 265                 270

Thr Phe Glu Asn Tyr Gly Leu Asp Pro Glu Lys Arg Phe Asn Val Ser
        275                 280                 285

Glu Glu Val Tyr Glu Ile Phe Gln Asn Thr Met Leu Lys Arg Ala Asn
    290                 295                 300

Glu Asp Glu Ser Gln Trp Asn Ser Leu Leu Glu Lys Tyr Ala Glu Thr
305                 310                 315                 320

Tyr Pro Glu Leu Ala Glu Glu Phe Lys Leu Ala Ile Ser Gly Lys Leu
                325                 330                 335

Pro Lys Asn Tyr Lys Asp Glu Leu Pro Arg Phe Glu Leu Gly His Asn
            340                 345                 350

Gly Ala Ser Arg Ala Asp Ser Gly Thr Val Ile Gln Ala Ile Ser Lys
        355                 360                 365

Thr Val Pro Ser Phe Phe Gly Gly Ser Ala Asp Leu Ala Gly Ser Asn

```
                    370                 375                 380
Lys Ser Asn Val Asn Asp Ala Thr Asp Tyr Ser Ser Glu Thr Pro Glu
385                 390                 395                 400

Gly Lys Asn Val Trp Phe Gly Val Arg Glu Phe Ala Met Gly Ala Ala
                405                 410                 415

Val Asn Gly Met Ala Ala His Gly Gly Leu His Pro Tyr Gly Ala Thr
            420                 425                 430

Phe Phe Val Phe Ser Asp Tyr Leu Lys Pro Ala Leu Arg Leu Ser Ser
                435                 440                 445

Ile Met Gly Leu Asn Ala Thr Phe Ile Phe Thr His Asp Ser Ile Ala
        450                 455                 460

Val Gly Glu Asp Gly Pro Thr His Glu Pro Ile Glu Gln Leu Ala Gly
465                 470                 475                 480

Leu Arg Ala Ile Pro Asn Met Asn Val Ile Arg Pro Ala Asp Gly Asn
                485                 490                 495

Glu Thr Arg Val Ala Trp Glu Val Ala Leu Glu Ser Glu Ser Thr Pro
                500                 505                 510

Thr Ser Leu Val Leu Thr Arg Gln Asn Leu Pro Val Leu Asp Val Pro
        515                 520                 525

Glu Asp Val Val Glu Glu Gly Val Arg Lys Gly Ala Tyr Thr Val Tyr
530                 535                 540

Gly Ser Glu Glu Thr Pro Glu Phe Leu Leu Leu Ala Ser Gly Ser Glu
545                 550                 555                 560

Val Ser Leu Ala Val Glu Ala Ala Lys Asp Leu Glu Lys Gln Gly Lys
                565                 570                 575

Ser Val Arg Val Val Ser Met Pro Asn Trp Asn Ala Phe Glu Gln Gln
                580                 585                 590

Ser Glu Glu Tyr Lys Glu Ser Val Ile Pro Ser Ser Val Thr Lys Arg
        595                 600                 605

Val Ala Ile Glu Met Ala Ser Pro Leu Gly Trp His Lys Tyr Val Gly
            610                 615                 620

Thr Ala Gly Lys Val Ile Ala Ile Asp Gly Phe Gly Ala Ser Ala Pro
625                 630                 635                 640

Gly Asp Leu Val Val Glu Lys Tyr Gly Phe Thr Lys Glu Asn Ile Leu
                645                 650                 655

Asn Gln Val Met Ser Leu
            660

<210> SEQ ID NO 17
<211> LENGTH: 253
<212> TYPE: PRT
<213> ORGANISM: Staphylococcus aureus

<400> SEQUENCE: 17

Met Arg Thr Pro Ile Ile Ala Gly Asn Trp Lys Met Asn Lys Thr Val
1               5                   10                  15

Gln Glu Ala Lys Asp Phe Val Asn Ala Leu Pro Thr Leu Pro Asp Ser
                20                  25                  30

Lys Glu Val Glu Ser Val Ile Cys Ala Pro Ala Ile Gln Leu Asp Ala
            35                  40                  45

Leu Thr Thr Ala Val Lys Glu Gly Lys Ala Gln Gly Leu Glu Ile Gly
        50                  55                  60

Ala Gln Asn Thr Tyr Phe Glu Asp Asn Gly Ala Phe Thr Gly Glu Thr
65                  70                  75                  80

Ser Pro Val Ala Leu Ala Asp Leu Gly Val Lys Tyr Val Val Ile Gly
```

```
                    85                  90                  95
His Ser Glu Arg Arg Glu Leu Phe His Glu Thr Asp Glu Glu Ile Asn
                100                 105                 110
Lys Lys Ala His Ala Ile Phe Lys His Gly Met Thr Pro Ile Ile Cys
            115                 120                 125
Val Gly Glu Thr Asp Glu Arg Glu Ser Gly Lys Ala Asn Asp Val
        130                 135                 140
Val Gly Glu Gln Val Lys Lys Ala Val Ala Gly Leu Ser Glu Asp Gln
145                 150                 155                 160
Leu Lys Ser Val Val Ile Ala Tyr Glu Pro Ile Trp Ala Ile Gly Thr
                165                 170                 175
Gly Lys Ser Ser Thr Ser Glu Asp Ala Asn Glu Met Cys Ala Phe Val
            180                 185                 190
Arg Gln Thr Ile Ala Asp Leu Ser Ser Lys Glu Val Ser Glu Ala Thr
        195                 200                 205
Arg Ile Gln Tyr Gly Gly Ser Val Lys Pro Asn Asn Ile Lys Glu Tyr
    210                 215                 220
Met Ala Gln Thr Asp Ile Asp Gly Ala Leu Val Gly Gly Ala Ser Leu
225                 230                 235                 240
Lys Val Glu Asp Phe Val Gln Leu Leu Glu Gly Ala Lys
                245                 250

<210> SEQ ID NO 18
<211> LENGTH: 291
<212> TYPE: PRT
<213> ORGANISM: Staphylococcus aureus

<400> SEQUENCE: 18

Ala Val Tyr Ala Ser Arg Ala Asn Leu Lys Thr Val Met Ile Glu Arg
1               5                   10                  15
Gly Ile Pro Gly Gly Gln Met Ala Asn Thr Glu Glu Val Glu Asn Phe
            20                  25                  30
Pro Gly Phe Glu Met Ile Thr Gly Pro Asp Leu Ser Thr Lys Met Phe
        35                  40                  45
Glu His Ala Lys Lys Phe Gly Ala Val Tyr Gln Tyr Gly Asp Ile Lys
    50                  55                  60
Ser Val Glu Asp Lys Gly Glu Tyr Lys Val Ile Asn Phe Gly Asn Lys
65                  70                  75                  80
Glu Leu Thr Ala Lys Ala Val Ile Ile Ala Thr Gly Ala Glu Tyr Lys
                85                  90                  95
Lys Ile Gly Val Pro Gly Glu Gln Glu Leu Gly Gly Arg Gly Val Ser
            100                 105                 110
Tyr Cys Ala Val Cys Asp Gly Ala Phe Phe Lys Asn Lys Arg Leu Phe
        115                 120                 125
Val Ile Gly Gly Gly Asp Ser Ala Val Glu Glu Gly Thr Phe Leu Thr
    130                 135                 140
Lys Phe Ala Asp Lys Val Thr Ile Val His Arg Arg Asp Glu Leu Arg
145                 150                 155                 160
Ala Gln Arg Ile Leu Gln Asp Arg Ala Phe Lys Asn Asp Lys Ile Asp
                165                 170                 175
Phe Ile Trp Ser His Thr Leu Lys Ser Ile Asn Glu Lys Asp Gly Lys
            180                 185                 190
Val Gly Ser Val Thr Leu Thr Ser Thr Lys Asp Gly Ser Glu Glu Thr
        195                 200                 205
His Glu Ala Asp Gly Val Phe Ile Tyr Ile Gly Met Lys Pro Leu Thr
```

```
                210                 215                 220
Ala Pro Phe Lys Asp Leu Gly Ile Thr Asn Asp Val Gly Tyr Ile Val
225                 230                 235                 240

Thr Lys Asp Asp Met Thr Thr Ser Val Pro Gly Ile Phe Ala Ala Gly
                245                 250                 255

Asp Val Arg Asp Lys Gly Leu Arg Gln Ile Val Thr Ala Thr Gly Asp
                260                 265                 270

Gly Ser Ile Ala Ala Gln Ser Ala Glu Tyr Ile Glu His Leu Asn
                275                 280                 285

Asp Gln Ala
        290

<210> SEQ ID NO 19
<211> LENGTH: 412
<212> TYPE: PRT
<213> ORGANISM: Staphylococcus aureus

<400> SEQUENCE: 19

Met Ser Tyr Ile Thr Lys Gln Asp Lys Val Ile Ala Glu Ala Ile Glu
1               5                   10                  15

Arg Glu Phe Gln Arg Gln Asn Ser Asn Ile Glu Leu Ile Ala Ser Glu
                20                  25                  30

Asn Phe Val Ser Glu Ala Val Met Glu Ala Gln Gly Ser Val Leu Thr
            35                  40                  45

Asn Lys Tyr Ala Glu Gly Tyr Pro Gly Arg Arg Tyr Tyr Gly Gly Cys
    50                  55                  60

Glu Phe Val Asp Val Thr Glu Ser Ile Ala Ile Asp Arg Ala Lys Ala
65                  70                  75                  80

Leu Phe Gly Ala Glu His Val Asn Val Gln Pro His Ser Gly Ser Gln
                85                  90                  95

Ala Asn Met Ala Val Tyr Leu Val Ala Leu Glu Met Gly Asp Thr Val
            100                 105                 110

Leu Gly Met Asn Leu Ser His Gly Gly His Leu Thr His Gly Ala Pro
        115                 120                 125

Val Asn Phe Ser Gly Lys Phe Tyr Asn Phe Val Glu Tyr Gly Val Asp
    130                 135                 140

Lys Asp Thr Glu Arg Ile Asn Tyr Asp Glu Val Arg Lys Leu Ala Leu
145                 150                 155                 160

Glu His Lys Pro Lys Leu Ile Val Ala Gly Ala Ser Ala Tyr Ser Arg
                165                 170                 175

Thr Ile Asp Phe Lys Lys Phe Lys Glu Ile Ala Asp Glu Val Asn Ala
            180                 185                 190

Lys Leu Met Val Asp Met Ala His Ile Ala Gly Leu Val Ala Ala Gly
        195                 200                 205

Leu His Pro Asn Pro Val Glu Tyr Ala Asp Phe Val Thr Thr Thr Thr
    210                 215                 220

His Lys Thr Leu Arg Gly Pro Arg Gly Gly Met Ile Leu Cys Lys Glu
225                 230                 235                 240

Glu Tyr Lys Lys Asp Ile Asp Lys Thr Ile Phe Pro Gly Ile Gln Gly
                245                 250                 255

Gly Pro Leu Glu His Val Ile Ala Ala Lys Ala Val Ala Phe Gly Glu
            260                 265                 270

Ala Leu Glu Asn Asn Phe Lys Thr Tyr Gln Gln Gln Val Val Lys Asn
        275                 280                 285

Ala Lys Val Leu Ala Glu Ala Leu Ile Asn Glu Gly Phe Arg Ile Val
```

```
                    290                 295                 300
Ser Gly Gly Thr Asp Asn His Leu Val Ala Val Asp Val Lys Gly Ser
305                 310                 315                 320

Ile Gly Leu Thr Gly Lys Glu Ala Glu Thr Leu Asp Ser Val Gly
                325                 330                 335

Ile Thr Cys Asn Lys Asn Thr Ile Pro Phe Asp Gln Glu Lys Pro Phe
                340                 345                 350

Val Thr Ser Gly Ile Arg Leu Gly Thr Pro Ala Ala Thr Thr Arg Gly
                355                 360                 365

Phe Asp Glu Lys Ala Phe Glu Glu Val Ala Lys Ile Ile Ser Leu Ala
        370                 375                 380

Leu Lys Asn Ser Lys Asp Glu Glu Lys Leu Gln Gln Ala Lys Glu Arg
385                 390                 395                 400

Val Ala Lys Leu Thr Ala Glu Tyr Pro Leu Tyr Gln
                405                 410

<210> SEQ ID NO 20
<211> LENGTH: 296
<212> TYPE: PRT
<213> ORGANISM: Staphylococcus aureus

<400> SEQUENCE: 20

Met Leu Leu Gly Ser His Val Ser Met Ser Gly Lys Lys Met Leu Glu
1               5                   10                  15

Gly Ser Ala Ile Glu Ala Tyr Glu Tyr Gly Glu Thr Thr Phe Met Ile
                20                  25                  30

Tyr Thr Gly Ala Pro Gln Asn Thr Arg Arg Lys Ser Ile Glu Asp Leu
            35                  40                  45

Asn Ile Thr Lys Gly His Glu Val Met Glu Lys Tyr Gly Leu Ser Asn
50                  55                  60

Ile Val Val His Ala Pro Tyr Ile Ile Asn Ile Ala Asn Thr Thr Lys
65                  70                  75                  80

Pro Glu Thr Phe Asn Leu Gly Val Asp Phe Leu Gln Gln Glu Ile Glu
                85                  90                  95

Arg Thr Gln Ala Ile Gly Ala Lys Asp Ile Val Leu His Pro Gly Ala
            100                 105                 110

His Val Gly Ala Gly Val Asp Ala Gly Ile Asn Lys Ile Ile Glu Gly
        115                 120                 125

Leu Asn Glu Val Leu Thr Asn Asp Asn Asn Val Arg Ile Ala Leu Glu
130                 135                 140

Thr Met Ala Gly Lys Gly Thr Glu Ile Gly Arg Ser Phe Glu Glu Leu
145                 150                 155                 160

Ala Arg Ile Ile Asp Gly Val His Asn Asn Glu Arg Leu Ser Val Cys
                165                 170                 175

Phe Asp Thr Cys His Thr His Asp Ala Gly Tyr Asn Val Lys Glu Asp
            180                 185                 190

Phe Asp Gly Val Leu Asn Glu Phe Asp Lys Ile Ile Gly Val Asp Arg
        195                 200                 205

Ile Lys Val Val His Val Asn Asp Ser Lys Asn Asp Arg Gly Ala Gln
210                 215                 220

Lys Asp Arg His Glu Asn Ile Gly Phe Gly Tyr Ile Gly Phe Asp Ala
225                 230                 235                 240

Leu Asn Tyr Ile Val His His Asp Ser Phe Lys Asp Ile Pro Lys Ile
                245                 250                 255

Leu Glu Thr Pro Tyr Val Gly Glu Asp Lys Lys Asn Lys Lys Pro Pro
```

```
                    260                 265                 270
Tyr Lys Leu Glu Ile Glu Met Leu Lys Gln Gln Gln Phe Asp Pro Glu
        275                 280                 285

Leu Lys Asn Lys Val Met Gln Gln
    290                 295

<210> SEQ ID NO 21
<211> LENGTH: 318
<212> TYPE: PRT
<213> ORGANISM: Staphylococcus aureus

<400> SEQUENCE: 21

Met Tyr Asn Pro Phe Asp Glu Ala Tyr His Gly Leu Cys Glu Glu Ile
1               5                   10                  15

Leu Glu Ile Gly Asn Arg Arg Asp Asp Arg Thr His Thr Gly Thr Ile
            20                  25                  30

Ser Lys Phe Gly His Gln Leu Arg Phe Asp Leu Thr Lys Gly Phe Pro
        35                  40                  45

Leu Leu Thr Thr Lys Lys Val Ser Phe Lys Leu Val Ala Thr Glu Leu
    50                  55                  60

Leu Trp Phe Ile Lys Gly Asp Thr Asn Ile Gln Tyr Leu Leu Lys Tyr
65                  70                  75                  80

Asn Asn Asn Ile Trp Asn Glu Trp Ala Phe Glu Asn Tyr Val Gln Ser
                85                  90                  95

Asp Asp Tyr His Gly Pro Asp Met Thr Asp Phe Gly His Arg Ser Gln
            100                 105                 110

Gln Asp Pro Glu Phe Asn Glu Gln Tyr Lys Glu Glu Met Lys Lys Phe
        115                 120                 125

Lys Glu Arg Ile Leu Asn Asp Asp Ala Phe Ala Lys Lys Tyr Gly Asn
    130                 135                 140

Leu Gly Asn Val Tyr Gly Lys Gln Trp Arg Asp Trp Glu Asp Lys Asn
145                 150                 155                 160

Gly Asn His Tyr Asp Gln Leu Lys Ser Val Ile Gln Gln Ile Lys Thr
                165                 170                 175

Asn Pro Asn Ser Arg Arg His Ile Val Ser Ala Trp Asn Pro Thr Glu
            180                 185                 190

Ile Asp Ser Met Ala Leu Pro Pro Cys His Thr Met Phe Gln Phe Tyr
        195                 200                 205

Val Gln Glu Gly Lys Leu Asn Cys Gln Leu Tyr Gln Arg Ser Ala Asp
    210                 215                 220

Ile Phe Leu Gly Val Pro Phe Asn Ile Ala Ser Tyr Ala Leu Leu Thr
225                 230                 235                 240

His Leu Val Ala Lys Glu Cys Gly Leu Glu Val Gly Glu Phe Ile His
                245                 250                 255

Thr Phe Gly Asp Ala His Ile Tyr Ser Asn His Met Asp Ala Ile His
            260                 265                 270

Thr Gln Leu Ser Arg Asp Ser Tyr Leu Pro Pro Gln Leu Lys Ile Asn
        275                 280                 285

Thr Asp Lys Ser Ile Phe Asp Ile Asn Tyr Glu Asp Leu Glu Leu Ile
    290                 295                 300

Asn Tyr Glu Ser His Pro Ala Ile Lys Ala Pro Ile Ala Val
305                 310                 315

<210> SEQ ID NO 22
<211> LENGTH: 238
<212> TYPE: PRT
```

<213> ORGANISM: Staphylococcus aureus

<400> SEQUENCE: 22

```
Met Lys Tyr Ala Gly Ile Leu Ala Gly Gly Ile Gly Ser Arg Met Gly
1               5                   10                  15

Asn Val Pro Leu Pro Lys Gln Phe Leu Asp Leu Asp Asn Lys Pro Ile
            20                  25                  30

Leu Ile His Thr Leu Glu Lys Phe Ile Leu Ile Asn Asp Phe Glu Lys
        35                  40                  45

Ile Ile Ile Ala Thr Pro Gln Gln Trp Met Thr His Thr Lys Asp Thr
    50                  55                  60

Leu Arg Lys Phe Lys Ile Ser Asp Glu Arg Ile Glu Val Ile Gln Gly
65                  70                  75                  80

Gly Ser Asp Arg Asn Asp Thr Ile Met Asn Ile Val Lys His Ile Glu
                85                  90                  95

Ser Thr Asn Gly Ile Asn Asp Asp Val Ile Val Thr His Asp Ala
            100                 105                 110

Val Arg Pro Phe Leu Thr His Arg Ile Ile Lys Glu Asn Ile Gln Ala
        115                 120                 125

Ala Leu Glu Tyr Gly Ala Val Asp Thr Val Ile Ala Ile Asp Thr
    130                 135                 140

Ile Val Thr Ser Lys Asp Asn Gln Thr Ile Asp Ala Ile Pro Val Arg
145                 150                 155                 160

Asn Glu Met Tyr Gln Gly Gln Thr Pro Gln Ser Phe Asn Ile Asn Leu
                165                 170                 175

Leu Lys Glu Ser Tyr Ala Gln Leu Ser Asp Glu Gln Lys Ser Ile Leu
            180                 185                 190

Ser Asp Ala Cys Lys Ile Val Glu Thr Asn Lys Pro Val Arg Leu
        195                 200                 205

Val Lys Gly Glu Leu Tyr Asn Ile Lys Val Thr Thr Pro Tyr Asp Leu
    210                 215                 220

Lys Val Ala Asn Ala Ile Ile Arg Gly Gly Ile Ala Asp Asp
225                 230                 235
```

<210> SEQ ID NO 23
<211> LENGTH: 317
<212> TYPE: PRT
<213> ORGANISM: Staphylococcus aureus

<400> SEQUENCE: 23

```
Met Glu Lys Val Tyr Val Ala Gly Ala Ile Pro Glu Val Gly Leu Lys
1               5                   10                  15

Leu Leu Gln Glu His Phe Glu Val Glu Met Tyr Glu Gly Lys Gly Leu
            20                  25                  30

Val Asp Lys Asp Thr Leu Ile Lys Gly Val Lys Asn Ala Thr Ala Leu
        35                  40                  45

Ile Ser Leu Leu Ser Thr Asn Val Asp Lys Asp Val Ile Asp Ala Gly
    50                  55                  60

Lys Asp Leu Lys Ile Ile Ala Asn Tyr Gly Ala Gly Phe Asn Asn Ile
65                  70                  75                  80

Asp Ile Glu Tyr Ala Arg Glu Lys Ser Ile Asp Val Thr Asn Thr Pro
                85                  90                  95

Lys Ala Ser Thr Asn Ala Thr Ala Asp Leu Thr Ile Gly Leu Val Leu
            100                 105                 110

Ala Val Ala Arg Arg Ile Val Glu Gly Asp Gln Leu Ser Arg Thr Thr
        115                 120                 125
```

```
Gly Phe Asp Gly Trp Ala Pro Leu Phe Phe Arg Gly Arg Glu Val Ser
    130                 135                 140

Gly Lys Thr Ile Gly Ile Ile Gly Leu Gly Glu Ile Gly Ser Ala Val
145                 150                 155                 160

Ala Arg Arg Ala Arg Ala Phe Asp Met Asp Val Leu Tyr Thr Gly Pro
                    165                 170                 175

Asn Arg Lys Glu Glu Lys Glu Arg Glu Ile Gly Ala Lys Tyr Val Asp
                180                 185                 190

Leu Asp Thr Leu Leu Lys Asn Ala Asp Phe Ile Thr Ile Asn Ala Ala
            195                 200                 205

Tyr Asn Pro Lys Met His His Leu Ile Asp Thr Glu Gln Phe Lys Met
        210                 215                 220

Met Lys Ser Thr Ala Tyr Leu Ile Asn Ala Ser Arg Gly Pro Ile Val
225                 230                 235                 240

His Glu Gln Ala Leu Val Gln Ala Leu Lys Asp Asn Glu Ile Glu Gly
                245                 250                 255

Ala Ala Leu Asp Val Tyr Glu Phe Glu Pro Asp Ile Thr Asp Asp Leu
                260                 265                 270

Lys Ser Leu Asn Asn Val Val Leu Thr Pro His Ile Gly Asn Ala Thr
            275                 280                 285

Phe Glu Ala Arg Asp Met Met Ser Lys Ile Val Ala Asn Ala Ala Ile
        290                 295                 300

Ser Ala Val Gln Gly Glu Lys Pro Gln Phe Val Val Asn
305                 310                 315

<210> SEQ ID NO 24
<211> LENGTH: 336
<212> TYPE: PRT
<213> ORGANISM: Staphylococcus aureus

<400> SEQUENCE: 24

Met Thr Glu Ile Gln Lys Pro Tyr Asp Leu Lys Gly Arg Ser Leu Leu
1               5                   10                  15

Lys Glu Ser Asp Phe Thr Lys Ala Glu Phe Glu Gly Leu Ile Asp Phe
            20                  25                  30

Ala Ile Thr Leu Lys Glu Tyr Lys Lys Asn Gly Ile Lys His His Tyr
        35                  40                  45

Leu Ser Gly Lys Asn Ile Ala Leu Leu Phe Glu Lys Asn Ser Thr Arg
    50                  55                  60

Thr Arg Ala Ala Phe Thr Val Ala Ser Ile Asp Leu Gly Ala His Pro
65                  70                  75                  80

Glu Phe Leu Gly Lys Asn Asp Ile Gln Leu Gly Lys Lys Glu Ser Val
                85                  90                  95

Glu Asp Thr Ala Lys Val Leu Gly Arg Met Phe Asp Gly Ile Glu Phe
            100                 105                 110

Arg Gly Phe Ser Gln Gln Ala Val Glu Asp Leu Ala Lys Phe Ser Gly
        115                 120                 125

Val Pro Val Trp Asn Gly Leu Thr Asp Asp Trp His Pro Thr Gln Met
    130                 135                 140

Leu Ala Asp Phe Met Thr Ile Lys Glu Asn Phe Gly Tyr Leu Glu Gly
145                 150                 155                 160

Ile Asn Leu Thr Tyr Val Gly Asp Gly Arg Asn Asn Ile Ala His Ser
                165                 170                 175

Leu Met Val Ala Gly Ala Met Leu Gly Val Asn Val Arg Ile Cys Thr
            180                 185                 190
```

```
Pro Lys Ser Leu Asn Pro Lys Glu Ala Tyr Val Asp Ile Ala Lys Glu
            195                 200                 205

Lys Ala Ser Gln Tyr Gly Gly Ser Ile Met Ile Thr Asp Asn Ile Ala
            210                 215                 220

Glu Ala Val Glu Asn Thr Asp Ala Ile Tyr Thr Asp Val Trp Val Ser
225                 230                 235                 240

Met Gly Glu Glu Ser Glu Phe Glu Gln Arg Ile Asn Leu Leu Lys Asp
            245                 250                 255

Tyr Gln Val Asn Gln Gln Met Phe Asp Leu Thr Gly Lys Asp Ser Thr
            260                 265                 270

Ile Phe Leu His Cys Leu Pro Ala Phe His Asp Thr Asn Thr Leu Tyr
            275                 280                 285

Gly Gln Glu Ile Tyr Glu Lys Tyr Gly Leu Ala Glu Met Glu Val Thr
            290                 295                 300

Asp Gln Ile Phe Arg Ser Glu His Ser Lys Val Phe Asp Gln Ala Glu
305                 310                 315                 320

Asn Arg Met His Thr Ile Lys Ala Val Met Ala Thr Leu Gly Ser
            325                 330                 335

<210> SEQ ID NO 25
<211> LENGTH: 336
<212> TYPE: PRT
<213> ORGANISM: Staphylococcus aureus

<400> SEQUENCE: 25

Met Arg Ala Ala Val Val Thr Lys Asp His Lys Val Ser Ile Glu Asp
1               5                   10                  15

Lys Lys Leu Arg Ala Leu Lys Pro Gly Glu Ala Leu Val Gln Thr Glu
            20                  25                  30

Tyr Cys Gly Val Cys His Thr Asp Leu His Val Lys Asn Ala Asp Phe
        35                  40                  45

Gly Asp Val Thr Gly Val Thr Leu Gly His Glu Gly Ile Gly Lys Val
    50                  55                  60

Ile Glu Val Ala Glu Asp Val Glu Ser Leu Lys Ile Gly Asp Arg Val
65                  70                  75                  80

Ser Ile Ala Trp Met Phe Glu Ser Cys Gly Arg Cys Glu Tyr Cys Thr
                85                  90                  95

Thr Gly Arg Glu Thr Leu Cys Arg Ser Val Lys Asn Ala Gly Tyr Thr
            100                 105                 110

Val Asp Gly Ala Met Ala Glu Gln Val Ile Val Thr Ala Asp Tyr Ala
        115                 120                 125

Val Lys Val Pro Glu Lys Leu Asp Pro Ala Ala Ala Ser Ser Ile Thr
    130                 135                 140

Cys Ala Gly Val Thr Thr Tyr Lys Ala Val Lys Val Ser Asn Val Lys
145                 150                 155                 160

Pro Gly Gln Trp Leu Gly Val Phe Gly Ile Gly Gly Leu Gly Asn Leu
                165                 170                 175

Ala Leu Gln Tyr Ala Lys Asn Val Met Gly Ala Lys Ile Val Ala Phe
            180                 185                 190

Asp Ile Asn Asp Asp Lys Leu Ala Phe Ala Lys Glu Leu Gly Ala Asp
        195                 200                 205

Ala Ile Ile Asn Ser Lys Asp Val Asp Pro Val Ala Glu Val Met Lys
    210                 215                 220

Leu Thr Asp Asn Lys Gly Leu Asp Ala Thr Val Val Thr Ser Val Ala
225                 230                 235                 240
```

```
Lys Thr Pro Phe Asn Gln Ala Val Asp Val Lys Ala Gly Ala Arg
                245                 250                 255

Val Val Ala Val Gly Leu Pro Val Asp Lys Met Asn Leu Asp Ile Pro
            260                 265                 270

Arg Leu Val Leu Asp Gly Ile Glu Val Gly Ser Leu Val Gly Thr
                275                 280                 285

Arg Gln Asp Leu Arg Glu Ala Phe Glu Phe Ala Ala Glu Asn Lys Val
    290                 295                 300

Thr Pro Lys Val Gln Leu Arg Lys Leu Glu Glu Ile Asn Asp Ile Phe
305                 310                 315                 320

Glu Glu Met Glu Asn Gly Thr Ile Thr Gly Arg Met Val Ile Lys Phe
                325                 330                 335

<210> SEQ ID NO 26
<211> LENGTH: 281
<212> TYPE: PRT
<213> ORGANISM: Staphylococcus haemolyticus

<400> SEQUENCE: 26

Met Lys Lys Leu Ile Phe Leu Ile Val Ile Ala Leu Val Leu Ser Ala
1               5                   10                  15

Cys Asn Ser Asn Ser Ser His Ala Lys Glu Leu Asn Asp Leu Glu Lys
            20                  25                  30

Lys Tyr Asn Ala His Ile Gly Val Tyr Ala Leu Asp Thr Lys Ser Gly
        35                  40                  45

Lys Glu Val Lys Phe Asn Ser Asp Lys Arg Phe Ala Tyr Ala Ser Thr
    50                  55                  60

Ser Lys Ala Ile Asn Ser Ala Ile Leu Leu Glu Gln Val Pro Tyr Asn
65                  70                  75                  80

Lys Leu Asn Lys Lys Val His Ile Asn Lys Asp Asp Ile Val Ala Tyr
                85                  90                  95

Ser Pro Ile Leu Glu Lys Tyr Val Gly Lys Asp Ile Thr Leu Lys Ala
            100                 105                 110

Leu Ile Glu Ala Ser Met Thr Tyr Ser Asp Asn Thr Ala Asn Asn Lys
        115                 120                 125

Ile Ile Lys Glu Ile Gly Gly Ile Lys Lys Val Lys Gln Arg Leu Lys
    130                 135                 140

Glu Leu Gly Asp Lys Val Thr Asn Pro Val Arg Tyr Glu Ile Glu Leu
145                 150                 155                 160

Asn Tyr Tyr Ser Pro Lys Ser Lys Lys Asp Thr Ser Thr Pro Ala Ala
                165                 170                 175

Phe Gly Lys Thr Leu Asn Lys Leu Ile Ala Asn Gly Lys Leu Ser Lys
            180                 185                 190

Glu Asn Lys Lys Phe Leu Leu Asp Leu Met Leu Asn Asn Lys Ser Gly
        195                 200                 205

Asp Thr Leu Ile Lys Asp Gly Val Pro Lys Asp Tyr Lys Val Ala Asp
    210                 215                 220

Lys Ser Gly Gln Ala Ile Thr Tyr Ala Ser Arg Asn Asp Val Ala Phe
225                 230                 235                 240

Val Tyr Pro Lys Gly Gln Ser Glu Pro Ile Val Leu Val Ile Phe Thr
                245                 250                 255

Asn Lys Asp Asn Lys Ser Asp Lys Pro Asn Asp Lys Leu Ile Ser Glu
            260                 265                 270

Thr Ala Lys Ser Val Met Lys Glu Phe
        275                 280
```

<210> SEQ ID NO 27
<211> LENGTH: 140
<212> TYPE: PRT
<213> ORGANISM: Staphylococcus aureus

<400> SEQUENCE: 27

Met Ala Ile His Tyr Glu Thr Lys Ala Thr Asn Val Gly Gly Arg Lys
1               5                   10                  15

Gly His Val Tyr Thr Asp Asp Arg Ala Leu Asp Ile Asp Ile Val Pro
            20                  25                  30

Pro Ala Gln Ala Asp Gly Lys Ala Thr Asn Pro Glu Gln Leu Phe Ala
        35                  40                  45

Ala Gly Tyr Ala Ser Cys Phe Asn Gly Ala Phe Asp Leu Ile Leu Lys
    50                  55                  60

Gln Asn Lys Val Arg Asp Ala His Pro Glu Val Thr Leu Thr Val Arg
65                  70                  75                  80

Leu Glu Asp Asp Ser Asp Ser Glu Ser Pro Lys Leu Ser Val Ser Ile
                85                  90                  95

Asp Ala Thr Ile Lys Asn Val Ile Ser Gln Glu Glu Ala Glu Lys Tyr
            100                 105                 110

Leu Gln Met Ala His Glu Phe Cys Pro Tyr Ser Lys Ala Thr Gln Gly
        115                 120                 125

Asn Ile Asn Val Asp Leu Asn Val Asn Val Val Asp
    130                 135                 140

<210> SEQ ID NO 28
<211> LENGTH: 224
<212> TYPE: PRT
<213> ORGANISM: Staphylococcus aureus

<400> SEQUENCE: 28

Met Ile Asn Lys Asn Asp Ile Val Ala Asp Val Val Thr Asp Tyr Pro
1               5                   10                  15

Lys Ala Ala Asp Ile Phe Arg Ser Val Gly Ile Asp Phe Cys Cys Gly
            20                  25                  30

Gly Gln Val Ser Ile Glu Ala Ala Leu Gly Lys Lys Asn Val Asp
        35                  40                  45

Leu Asn Glu Leu Leu Gln Arg Leu Asn Asp Val Asn Lys Thr Asn Thr
    50                  55                  60

Pro Gly Ser Leu Asn Pro Lys Phe Leu Asn Val Ser Ser Leu Ile Gln
65                  70                  75                  80

Tyr Ile Gln Ser Ala Tyr His Glu Pro Leu Arg Glu Glu Phe Lys Asn
                85                  90                  95

Leu Thr Pro Tyr Val Thr Lys Leu Ser Lys Val His Gly Pro Asn His
            100                 105                 110

Pro Tyr Leu Val Glu Leu Lys Glu Thr Tyr Asp Thr Phe Lys Asn Gly
        115                 120                 125

Met Leu Glu His Met Gln Lys Glu Asp Val Asp Phe Pro Lys Leu
    130                 135                 140

Ile Lys Tyr Glu Gln Gly Glu Val Val Asp Ile Asn Thr Val Ile
145                 150                 155                 160

Asp Asp Leu Val Ser Asp His Ile Ala Thr Gly Glu Leu Leu Val Lys
                165                 170                 175

Met Ser Glu Leu Thr Ser Ser Tyr Glu Pro Pro Ile Glu Ala Cys Gly
            180                 185                 190

Thr Trp Arg Leu Val Tyr Gln Arg Leu Lys Ala Leu Glu Val Leu Thr
            195                 200                 205

His Glu His Val His Leu Glu Asn His Val Leu Phe Lys Lys Val Ser
    210                 215                 220

<210> SEQ ID NO 29
<211> LENGTH: 183
<212> TYPE: PRT
<213> ORGANISM: Staphylococcus aureus

<400> SEQUENCE: 29

Met Leu Thr Met Lys Asp Ile Ile Arg Asp Gly His Pro Thr Leu Arg
1               5                   10                  15

Gln Lys Ala Ala Glu Leu Glu Leu Pro Leu Thr Lys Glu Glu Lys Glu
            20                  25                  30

Thr Leu Ile Ala Met Arg Glu Phe Leu Val Asn Ser Gln Asp Glu Glu
        35                  40                  45

Ile Ala Lys Arg Tyr Gly Leu Arg Ser Gly Val Gly Leu Ala Ala Pro
    50                  55                  60

Gln Ile Asn Ile Ser Lys Arg Met Ile Ala Val Leu Ile Pro Asp Asp
65                  70                  75                  80

Gly Ser Gly Lys Ser Tyr Asp Tyr Met Leu Val Asn Pro Lys Ile Val
                85                  90                  95

Ser His Ser Val Gln Glu Ala Tyr Leu Pro Thr Gly Glu Gly Cys Leu
            100                 105                 110

Ser Val Asp Asp Asn Val Ala Gly Leu Val His Arg His Asn Arg Ile
        115                 120                 125

Thr Ile Lys Ala Lys Asp Ile Glu Gly Asn Asp Ile Gln Leu Arg Leu
    130                 135                 140

Lys Gly Tyr Pro Ala Ile Val Phe Gln His Glu Ile Asp His Leu Asn
145                 150                 155                 160

Gly Val Met Phe Tyr Asp His Ile Asp Lys Asp His Pro Leu Gln Pro
                165                 170                 175

His Thr Asp Ala Val Glu Val
            180

<210> SEQ ID NO 30
<211> LENGTH: 346
<212> TYPE: PRT
<213> ORGANISM: Staphylococcus aureus

<400> SEQUENCE: 30

Met Thr Thr Asn Thr Val Thr Leu Gln Thr Ala His Ile Val Ser Leu
1               5                   10                  15

Gly Asp Ile Glu Glu Ala Lys Ala Ser Ile Lys Pro Phe Ile Arg Arg
            20                  25                  30

Thr Pro Leu Ile Lys Ser Met Tyr Leu Ser Gln Ser Ile Thr Lys Gly
        35                  40                  45

Asn Val Phe Leu Lys Leu Glu Asn Met Gln Phe Thr Gly Ser Phe Lys
    50                  55                  60

Phe Arg Gly Ala Ser Asn Lys Ile Asn His Leu Thr Asp Glu Gln Lys
65                  70                  75                  80

Glu Lys Gly Ile Ile Ala Ala Ser Ala Gly Asn His Ala Gln Gly Val
                85                  90                  95

Ala Leu Thr Ala Lys Leu Leu Gly Ile Asp Ala Thr Ile Val Met Pro
            100                 105                 110

Glu Thr Ala Pro Gln Ala Lys Gln Gln Ala Thr Lys Gly Tyr Gly Ala

```
                115                 120                 125
Lys Val Ile Leu Lys Gly Lys Asn Phe Asn Glu Thr Arg Leu Tyr Met
    130                 135                 140

Glu Glu Leu Ala Lys Glu Asn Gly Met Thr Ile Val His Pro Tyr Asp
145                 150                 155                 160

Asp Lys Phe Val Met Ala Gly Gln Gly Thr Ile Gly Leu Glu Ile Leu
                165                 170                 175

Asp Asp Ile Trp Asn Val Asn Thr Val Ile Val Pro Val Gly Gly Gly
                180                 185                 190

Gly Leu Ile Ala Gly Ile Ala Thr Ala Leu Lys Ser Phe Asn Pro Ser
            195                 200                 205

Ile His Ile Ile Gly Val Gln Ser Glu Asn Val His Gly Met Ala Glu
            210                 215                 220

Ser Phe Tyr Lys Arg Asp Leu Thr Glu His Arg Val Asp Ser Thr Ile
225                 230                 235                 240

Ala Asp Gly Cys Asp Val Lys Val Pro Gly Glu Gln Thr Tyr Glu Val
                245                 250                 255

Val Lys His Leu Val Asp Glu Phe Ile Leu Val Thr Glu Glu Glu Ile
                260                 265                 270

Glu His Ala Met Lys Asp Leu Met Gln Arg Ala Lys Ile Ile Thr Glu
            275                 280                 285

Gly Ala Gly Ala Leu Pro Thr Ala Ala Ile Leu Ser Gly Lys Ile Asn
        290                 295                 300

Asn Lys Trp Leu Glu Asp Lys Asn Val Val Ala Leu Val Ser Gly Gly
305                 310                 315                 320

Asn Val Asp Leu Thr Arg Val Ser Gly Val Ile Glu His Gly Leu Asn
                325                 330                 335

Ile Ala Asp Thr Ser Lys Gly Val Val Gly
            340                 345

<210> SEQ ID NO 31
<211> LENGTH: 372
<212> TYPE: PRT
<213> ORGANISM: Staphylococcus aureus

<400> SEQUENCE: 31

Met Lys Ile Gly Ile Pro Arg Glu Ile Lys Asn Asn Glu Asn Arg Val
1               5                   10                  15

Gly Leu Ser Pro Ser Gly Val His Ala Leu Val Glu Ser Gly His Thr
            20                  25                  30

Val Leu Val Glu Thr Asn Ala Gly Ser Gly Ser Phe Phe Glu Asp Val
        35                  40                  45

Asp Tyr Lys Glu Ala Gly Ala Glu Ile Val Ala Glu Gln Ala Lys Val
    50                  55                  60

Trp Asp Val Asp Met Val Ile Lys Val Lys Glu Pro Leu Glu Ser Glu
65                  70                  75                  80

Tyr Pro Tyr Phe Lys Glu Gly Leu Val Leu Phe Thr Tyr Leu His Leu
                85                  90                  95

Ala Asn Glu Glu Lys Leu Thr Gln Ala Leu Ile Asp Arg Lys Val Ile
            100                 105                 110

Ser Ile Ala Tyr Glu Thr Val Gln Leu Pro Asp Arg Ser Leu Pro Leu
        115                 120                 125

Leu Ser Pro Met Ser Glu Val Ala Gly Arg Met Ser Ala Gln Val Gly
    130                 135                 140

Ala Glu Phe Leu Gln Lys Leu Asn Gly Gly Met Gly Ile Leu Leu Gly
```

```
                145                 150                 155                 160
Gly Val Pro Gly Val Pro Lys Gly Lys Val Thr Ile Ile Gly Gly
                    165                 170                 175
Gln Ala Gly Thr Asn Ala Ala Lys Ile Ala Leu Gly Leu Gly Ala Asp
                    180                 185                 190
Val Thr Ile Leu Asp Val Asn Pro Lys Arg Leu Gln Gln Leu Asp Asp
                    195                 200                 205
Leu Phe Gly Gly Arg Val His Thr Ile Met Ser Asn Pro Leu Asn Ile
        210                 215                 220
Glu Leu Tyr Val Lys Gln Ser Asp Leu Val Ile Gly Ala Val Leu Ile
225                 230                 235                 240
Pro Gly Ala Lys Ala Pro Arg Leu Val Thr Glu Asp Met Ile Lys Gln
                    245                 250                 255
Met Lys Asn Gly Ser Val Ile Ile Asp Ile Ala Ile Asp Gln Gly Gly
                260                 265                 270
Ile Phe Glu Thr Thr Asp Lys Ile Thr Thr His Asp Asp Pro Thr Tyr
                275                 280                 285
Ile Lys His Gly Val Val His Tyr Ala Val Ala Asn Met Pro Gly Ala
        290                 295                 300
Val Pro Arg Thr Ser Thr Leu Ala Leu Asn Asn Ala Thr Leu Pro Tyr
305                 310                 315                 320
Ala Leu Met Leu Ala Asn Lys Gly Tyr Arg Glu Ala Phe Lys Ser Asn
                    325                 330                 335
Gln Pro Leu Ser Leu Gly Leu Asn Thr Tyr Lys Gly His Val Thr Asn
                    340                 345                 350
Lys Gly Val Ala Glu Ala Phe Glu Met Glu Tyr Lys Ser Val Glu Glu
                355                 360                 365
Ala Leu Gln Leu
        370

<210> SEQ ID NO 32
<211> LENGTH: 491
<212> TYPE: PRT
<213> ORGANISM: Staphylococcus aureus

<400> SEQUENCE: 32

Met Asn Phe Lys Leu Asn Asn Thr Leu Ser Asn Glu Ile Asn Thr Leu
1               5                   10                  15
Ile Ile Gly Ile Pro Glu His Leu Asn Gln Leu Glu Arg Ile Ser Phe
            20                  25                  30
Asn His Ile Asp Ile Thr Glu Ser Leu Glu Arg Leu Lys His Gln His
        35                  40                  45
Ile Ile Gly Ser Lys Val Gly Lys Ile Tyr Thr Thr Ala Phe Asp Val
    50                  55                  60
Gln Asp Gln Thr Tyr Arg Leu Ile Thr Val Gly Leu Gly Asn Leu Lys
65                  70                  75                  80
Ala Arg Ser Tyr Gln Asp Met Leu Lys Ile Trp Gly His Leu Phe Gln
                85                  90                  95
Tyr Ile Lys Ser Glu His Ile Glu Asp Thr Tyr Leu Leu Met Asp Ser
            100                 105                 110
Phe Ile Ser Lys Tyr Asp Gln Leu Ser Asp Val Leu Met Ala Cys Gly
        115                 120                 125
Ile Gln Ser Glu Arg Ala Thr Tyr Glu Phe Asp His Tyr Lys Ser Ser
    130                 135                 140
Lys Lys Ala Pro Phe Lys Thr Asn Leu Asn Leu Ile Ser Glu Ser Leu
```

```
            145                 150                 155                 160
Ile Glu Leu Asp Phe Ile His Glu Gly Ile Ser Ile Gly Gln Ser Ile
                165                 170                 175

Asn Leu Ala Arg Asp Phe Ser Asn Met Pro Pro Asn Val Leu Thr Pro
            180                 185                 190

Gln Thr Phe Ala Glu Asp Ile Val Asn His Phe Lys Asn Thr Lys Val
        195                 200                 205

Lys Val Asp Val Lys Asp Tyr Asp Thr Leu Val Ser Glu Gly Phe Gly
    210                 215                 220

Leu Leu Gln Ala Val Gly Lys Gly Ser Lys His Lys Pro Arg Leu Val
225                 230                 235                 240

Thr Ile Thr Tyr Asn Gly Lys Asp Lys Asp Val Ala Pro Ile Ala Leu
                245                 250                 255

Val Gly Lys Gly Ile Thr Tyr Asp Ser Gly Gly Tyr Ser Ile Lys Thr
            260                 265                 270

Lys Asn Gly Met Ala Thr Met Lys Phe Asp Met Cys Gly Ala Ala Asn
        275                 280                 285

Val Val Gly Ile Ile Glu Ala Ala Ser Arg Leu Gln Leu Pro Val Asn
    290                 295                 300

Ile Val Gly Val Leu Ala Cys Ala Glu Asn Met Ile Asn Glu Ala Ser
305                 310                 315                 320

Met Lys Pro Asp Asp Val Phe Thr Ala Leu Ser Gly Glu Thr Val Glu
                325                 330                 335

Val Met Asn Thr Asp Ala Glu Gly Arg Leu Val Leu Ala Asp Ala Val
            340                 345                 350

Tyr Tyr Ala Asn Gln Tyr Gln Pro Ser Val Ile Met Asp Phe Ala Thr
        355                 360                 365

Leu Thr Gly Ala Ala Ile Val Ala Leu Gly Asp Asp Lys Ala Ala Ala
    370                 375                 380

Phe Glu Ser Asn Ser Lys Val Ile Leu Asn Asp Ile Leu Gln Ile Ser
385                 390                 395                 400

Ser Lys Val Asp Glu Met Val Phe Glu Leu Pro Ile Thr Ala Thr Glu
                405                 410                 415

Arg Ala Ser Ile Asn His Ser Asp Ile Ala Asp Leu Val Asn His Thr
            420                 425                 430

Asn Gly Gln Gly Lys Ala Leu Phe Ala Ala Ser Phe Val Thr His Phe
        435                 440                 445

Ser Gly Gln Thr Pro His Ile His Phe Asp Ile Ala Gly Pro Ala Thr
    450                 455                 460

Thr Asn Lys Ala Ser Tyr Asn Gly Pro Lys Gly Pro Thr Gly Phe Met
465                 470                 475                 480

Ile Pro Thr Ile Val Gln Trp Leu Lys Gln Gln
                485                 490

<210> SEQ ID NO 33
<211> LENGTH: 555
<212> TYPE: PRT
<213> ORGANISM: Staphylococcus aureus

<400> SEQUENCE: 33

Met Thr His Leu Ser Asp Leu Asp Ile Ala Asn Gln Ser Thr Leu Gln
1               5                   10                  15

Pro Ile Lys Asp Ile Ala Ala Ser Val Gly Ile Ser Glu Asp Ala Leu
            20                  25                  30

Glu Pro Tyr Gly His Tyr Lys Ala Lys Ile Asp Ile Asn Lys Ile Thr
```

-continued

```
                35                  40                  45
Pro Arg Glu Asn Lys Gly Lys Val Val Leu Val Thr Ala Met Ser Pro
 50                  55                  60

Thr Pro Ala Gly Glu Gly Lys Ser Thr Val Thr Val Gly Leu Ala Asp
 65                  70                  75                  80

Ala Phe His Glu Leu Asn Lys Asn Val Met Val Ala Leu Arg Glu Pro
                 85                  90                  95

Ala Leu Gly Pro Thr Phe Gly Ile Lys Gly Ala Thr Gly Gly Gly
            100                 105                 110

Tyr Ala Gln Val Leu Pro Met Glu Asp Ile Asn Leu His Phe Asn Gly
            115                 120                 125

Asp Phe His Ala Ile Thr Thr Ala Asn Asn Ala Leu Ser Ala Phe Ile
130                 135                 140

Asp Asn His Ile His Gln Gly Asn Glu Leu Gly Ile Asp Gln Arg Arg
145                 150                 155                 160

Ile Glu Trp Lys Arg Val Leu Asp Met Asn Asp Arg Ala Leu Arg His
                165                 170                 175

Val Asn Val Gly Leu Gly Gly Pro Thr Asn Gly Val Pro Arg Glu Asp
            180                 185                 190

Gly Phe Asn Ile Thr Val Ala Ser Glu Ile Met Ala Ile Leu Cys Leu
            195                 200                 205

Ser Arg Ser Ile Lys Asp Leu Lys Asp Lys Ile Ser Arg Ile Thr Ile
210                 215                 220

Gly Tyr Thr Arg Asp Arg Lys Pro Val Thr Val Ala Asp Leu Lys Val
225                 230                 235                 240

Gln Gly Ala Leu Ala Met Ile Leu Lys Asp Ala Ile Lys Pro Asn Leu
                245                 250                 255

Val Gln Ser Ile Glu Gly Thr Pro Ala Leu Val His Gly Gly Pro Phe
            260                 265                 270

Ala Asn Ile Ala His Gly Cys Asn Ser Ile Leu Ala Thr Glu Thr Ala
            275                 280                 285

Arg Asp Leu Ala Asp Ile Val Val Thr Glu Ala Gly Phe Gly Ser Asp
290                 295                 300

Leu Gly Ala Glu Lys Phe Met Asp Ile Lys Ala Arg Glu Ala Gly Phe
305                 310                 315                 320

Asp Pro Ala Ala Val Val Val Ala Thr Ile Arg Ala Leu Lys Met
                325                 330                 335

His Gly Gly Val Ala Lys Asp Asn Leu Lys Glu Glu Asn Val Glu Ala
            340                 345                 350

Val Lys Ala Gly Ile Val Asn Leu Glu Arg His Val Asn Asn Ile Lys
            355                 360                 365

Lys Phe Gly Val Glu Pro Val Val Ala Ile Asn Ala Phe Ile His Asp
370                 375                 380

Thr Asp Ala Glu Val Glu Tyr Val Lys Ser Trp Ala Lys Glu Asn Asn
385                 390                 395                 400

Val Arg Ile Ala Leu Thr Glu Val Trp Glu Lys Gly Lys Gly Gly
                405                 410                 415

Val Asp Leu Ala Asn Glu Val Leu Glu Val Ile Asp Gln Pro Asn Ser
            420                 425                 430

Phe Lys Pro Leu Tyr Glu Leu Glu Leu Pro Leu Glu Gln Lys Ile Glu
            435                 440                 445

Lys Ile Val Thr Glu Ile Tyr Gly Gly Ser Lys Val Thr Phe Ser Ser
450                 455                 460
```

Lys Ala Gln Lys Gln Leu Lys Gln Phe Lys Glu Asn Gly Trp Asp Asn
465                 470                 475                 480

Tyr Pro Val Cys Met Ala Lys Thr Gln Tyr Ser Phe Ser Asp Asp Gln
                485                 490                 495

Thr Leu Leu Gly Ala Pro Ser Gly Phe Glu Ile Thr Ile Arg Glu Leu
            500                 505                 510

Glu Ala Lys Thr Gly Ala Gly Phe Ile Val Ala Leu Thr Gly Ala Ile
        515                 520                 525

Met Thr Met Pro Gly Leu Pro Lys Lys Pro Ala Ala Leu Asn Met Asp
    530                 535                 540

Val Thr Asp Asp Gly His Ala Ile Gly Leu Phe
545                 550                 555

<210> SEQ ID NO 34
<211> LENGTH: 322
<212> TYPE: PRT
<213> ORGANISM: Staphylococcus aureus

<400> SEQUENCE: 34

Met Lys Lys Ile Ala Val Leu Thr Ser Gly Gly Asp Ser Pro Gly Met
1               5                   10                  15

Asn Ala Ala Val Arg Ala Val Arg Thr Ala Ile Tyr Asn Glu Ile
            20                  25                  30

Glu Val Tyr Gly Val Tyr His Gly Tyr Gln Gly Leu Leu Asn Asp Asp
        35                  40                  45

Ile His Lys Leu Glu Leu Gly Ser Val Gly Asp Thr Ile Gln Arg Gly
    50                  55                  60

Gly Thr Phe Leu Tyr Ser Ala Arg Cys Pro Glu Phe Lys Glu Gln Glu
65                  70                  75                  80

Val Arg Lys Val Ala Ile Glu Asn Leu Arg Lys Arg Gly Ile Glu Gly
                85                  90                  95

Leu Val Val Ile Gly Gly Asp Gly Ser Tyr Arg Gly Ala Gln Arg Ile
            100                 105                 110

Ser Glu Glu Cys Lys Glu Ile Gln Thr Ile Gly Ile Pro Gly Thr Ile
        115                 120                 125

Asp Asn Asp Ile Asn Gly Thr Asp Phe Thr Ile Gly Phe Asp Thr Ala
    130                 135                 140

Leu Asn Thr Ile Ile Gly Leu Val Asp Lys Ile Arg Asp Thr Ala Ser
145                 150                 155                 160

Ser His Ala Arg Thr Phe Ile Ile Glu Ala Met Gly Arg Asp Cys Gly
                165                 170                 175

Asp Leu Ala Leu Trp Ala Gly Leu Ser Val Gly Ala Glu Thr Ile Val
            180                 185                 190

Val Pro Glu Val Lys Thr Asp Ile Lys Glu Ile Ala Asp Lys Ile Glu
        195                 200                 205

Gln Gly Ile Lys Arg Gly Lys Lys His Ser Ile Val Leu Val Ala Glu
    210                 215                 220

Gly Cys Met Thr Ala Gln Asp Cys Gln Lys Glu Leu Ser Gln Tyr Ile
225                 230                 235                 240

Asn Val Asp Asn Arg Val Ser Val Leu Gly His Val Gln Arg Gly Gly
                245                 250                 255

Ser Pro Thr Gly Ala Asp Arg Val Leu Ala Ser Arg Leu Gly Gly Tyr
            260                 265                 270

Ala Val Asp Leu Leu Met Gln Gly Glu Thr Ala Lys Gly Val Gly Ile
        275                 280                 285

```
Lys Asn Asn Lys Ile Val Ala Thr Ser Phe Asp Glu Ile Phe Asp Gly
        290                 295                 300

Lys Asp His Lys Phe Asp Tyr Ser Leu Tyr Glu Leu Ala Asn Lys Leu
305                 310                 315                 320

Ser Ile

<210> SEQ ID NO 35
<211> LENGTH: 422
<212> TYPE: PRT
<213> ORGANISM: Staphylococcus aureus

<400> SEQUENCE: 35

Met Pro Glu Val Lys Val Pro Glu Leu Ala Glu Ser Ile Thr Glu Gly
1               5                   10                  15

Thr Ile Ala Glu Trp Leu Lys Asn Val Gly Asp Ser Val Glu Lys Gly
            20                  25                  30

Glu Ala Ile Leu Glu Leu Glu Thr Asp Lys Val Asn Val Glu Val Val
        35                  40                  45

Ser Glu Glu Ala Gly Val Leu Ser Glu Gln Leu Ala Ser Glu Gly Asp
    50                  55                  60

Thr Val Glu Val Gly Gln Ala Ile Ala Ile Ile Gly Glu Gly Ser Gly
65                  70                  75                  80

Asn Ala Ser Lys Glu Asn Ser Asn Asp Asn Thr Pro Gln Gln Asn Glu
                85                  90                  95

Glu Thr Asn Asn Lys Lys Glu Glu Thr Thr Asn Asn Ser Val Asp Lys
            100                 105                 110

Ala Glu Val Asn Gln Ala Asn Asp Asp Asn Gln Gln Arg Ile Asn Ala
        115                 120                 125

Thr Pro Ser Ala Arg Arg Tyr Ala Arg Glu Asn Gly Val Asn Leu Ala
    130                 135                 140

Glu Val Ser Pro Lys Thr Asn Asp Val Val Arg Lys Glu Asp Ile Asp
145                 150                 155                 160

Lys Lys Gln Gln Ala Pro Ala Ser Thr Gln Thr Thr Gln Gln Ala Pro
                165                 170                 175

Ala Lys Glu Glu Lys Lys Tyr Asn Gln Tyr Pro Thr Lys Pro Val Ile
            180                 185                 190

Arg Glu Lys Met Ser Arg Arg Lys Lys Thr Ala Ala Lys Lys Leu Leu
        195                 200                 205

Glu Val Ser Asn Asn Thr Ala Met Leu Thr Thr Phe Asn Glu Val Asp
    210                 215                 220

Met Thr Asn Val Met Glu Leu Arg Lys Arg Lys Lys Glu Gln Phe Met
225                 230                 235                 240

Lys Asp His Asp Gly Thr Lys Leu Gly Phe Met Ser Phe Phe Thr Lys
                245                 250                 255

Ala Ser Val Ala Ala Leu Lys Lys Tyr Pro Glu Val Asn Ala Glu Ile
            260                 265                 270

Asp Gly Asp Asp Met Ile Thr Lys Gln Tyr Tyr Asp Ile Gly Val Ala
        275                 280                 285

Val Ser Thr Asp Asp Gly Leu Leu Val Pro Phe Val Arg Asp Cys Asp
    290                 295                 300

Lys Lys Asn Phe Ala Glu Ile Glu Ala Glu Ile Ala Asn Leu Ala Val
305                 310                 315                 320

Lys Ala Arg Glu Lys Lys Leu Gly Leu Asp Asp Met Val Asn Gly Ser
                325                 330                 335

Phe Thr Ile Thr Asn Gly Gly Ile Phe Gly Ser Met Met Ser Thr Pro
```

```
                        340                 345                 350
Ile Ile Asn Gly Asn Gln Ala Ala Ile Leu Gly Met His Ser Ile Ile
            355                 360                 365

Thr Arg Pro Ile Ala Ile Asp Gln Asp Thr Ile Glu Asn Arg Pro Met
    370                 375                 380

Met Tyr Ile Ala Leu Ser Tyr Asp His Arg Ile Ile Asp Gly Lys Glu
385                 390                 395                 400

Ala Val Gly Phe Leu Lys Thr Ile Lys Glu Leu Ile Glu Asn Pro Glu
                405                 410                 415

Asp Leu Leu Leu Glu Ser
            420

<210> SEQ ID NO 36
<211> LENGTH: 488
<212> TYPE: PRT
<213> ORGANISM: Staphylococcus aureus

<400> SEQUENCE: 36

Met Trp Glu Ser Lys Phe Ala Lys Glu Ser Leu Thr Phe Asp Asp Val
1               5                   10                  15

Leu Leu Ile Pro Ala Gln Ser Asp Ile Leu Pro Lys Asp Val Asp Leu
            20                  25                  30

Ser Val Gln Leu Ser Asp Lys Ala Lys Leu Asn Ile Pro Val Ile Ser
        35                  40                  45

Ala Gly Met Asp Thr Val Thr Glu Ser Lys Met Ala Ile Ala Met Ala
    50                  55                  60

Arg Gln Gly Gly Leu Gly Val Ile His Lys Asn Met Gly Val Glu Glu
65                  70                  75                  80

Gln Ala Asp Glu Val Gln Lys Val Lys Arg Ser Glu Asn Gly Val Ile
                85                  90                  95

Ser Asn Pro Phe Phe Leu Thr Pro Glu Glu Ser Val Tyr Glu Ala Glu
            100                 105                 110

Ala Leu Met Gly Lys Tyr Arg Ile Ser Gly Val Pro Ile Val Asp Asn
        115                 120                 125

Lys Glu Asp Arg Asn Leu Val Gly Ile Leu Thr Asn Arg Asp Leu Arg
    130                 135                 140

Phe Ile Glu Asp Phe Ser Ile Lys Ile Val Asp Val Met Thr Gln Glu
145                 150                 155                 160

Asn Leu Ile Thr Ala Pro Val Asn Thr Thr Leu Glu Glu Ala Glu Lys
                165                 170                 175

Ile Leu Gln Lys His Lys Ile Glu Lys Leu Pro Leu Val Lys Asp Gly
            180                 185                 190

Arg Leu Glu Gly Leu Ile Thr Ile Lys Asp Ile Glu Lys Val Ile Glu
        195                 200                 205

Phe Pro Asn Ala Ala Lys Asp Glu His Gly Arg Leu Leu Val Ala Ala
    210                 215                 220

Ala Ile Gly Ile Ser Lys Asp Thr Asp Ile Arg Ala Gln Lys Leu Val
225                 230                 235                 240

Glu Ala Gly Val Asp Val Leu Val Ile Asp Thr Ala His Gly His Ser
                245                 250                 255

Lys Gly Val Ile Asp Gln Val Lys His Ile Lys Lys Thr Tyr Pro Glu
            260                 265                 270

Ile Thr Leu Val Ala Gly Asn Val Ala Thr Ala Glu Ala Thr Lys Asp
        275                 280                 285

Leu Phe Glu Ala Gly Ala Asp Ile Val Lys Val Gly Ile Gly Pro Gly
```

```
                        290                 295                 300
Ser Ile Cys Thr Thr Arg Val Ala Gly Val Gly Val Pro Gln Ile
305                 310                 315                 320

Thr Ala Ile Tyr Asp Cys Ala Thr Glu Ala Arg Lys His Gly Lys Ala
                325                 330                 335

Ile Ile Ala Asp Gly Gly Ile Lys Phe Ser Gly Asp Ile Ile Lys Ala
                340                 345                 350

Leu Ala Ala Gly Gly His Ala Val Met Leu Gly Ser Leu Leu Ala Gly
                355                 360                 365

Thr Glu Glu Ser Pro Gly Ala Thr Glu Ile Phe Gln Gly Arg Gln Tyr
370                 375                 380

Lys Val Tyr Arg Gly Met Gly Ser Leu Gly Ala Met Glu Lys Gly Ser
385                 390                 395                 400

Asn Asp Arg Tyr Phe Gln Glu Asp Lys Ala Pro Lys Lys Phe Val Pro
                405                 410                 415

Glu Gly Ile Glu Gly Arg Thr Ala Tyr Lys Gly Ala Leu Gln Asp Thr
                420                 425                 430

Ile Tyr Gln Leu Met Gly Gly Val Arg Ala Gly Met Gly Tyr Thr Gly
                435                 440                 445

Ser His Asp Leu Arg Glu Leu Arg Glu Glu Ala Gln Phe Thr Arg Met
                450                 455                 460

Gly Pro Ala Gly Leu Ala Glu Ser His Pro His Asn Ile Gln Ile Thr
465                 470                 475                 480

Lys Glu Ser Pro Asn Tyr Ser Phe
                485

<210> SEQ ID NO 37
<211> LENGTH: 402
<212> TYPE: PRT
<213> ORGANISM: Staphylococcus aureus

<400> SEQUENCE: 37

Met Ala Gln Asp Arg Lys Lys Val Leu Val Leu Gly Ala Gly Tyr Ala
1               5                   10                  15

Gly Leu Gln Thr Val Thr Lys Leu Gln Lys Ala Ile Ser Thr Glu Glu
                20                  25                  30

Ala Glu Ile Thr Leu Ile Asn Lys Asn Glu Tyr His Tyr Glu Ala Thr
                35                  40                  45

Trp Leu His Glu Ala Ser Ala Gly Thr Leu Asn Tyr Glu Asp Val Leu
                50                  55                  60

Tyr Pro Val Glu Ser Val Leu Lys Lys Asp Lys Val Asn Phe Val Gln
65                  70                  75                  80

Ala Glu Val Thr Lys Ile Asp Arg Asp Ala Lys Lys Val Glu Thr Asn
                85                  90                  95

Gln Gly Ile Tyr Asp Phe Asp Ile Leu Val Val Ala Leu Gly Phe Val
                100                 105                 110

Ser Glu Thr Phe Gly Ile Glu Gly Met Lys Asp His Ala Phe Gln Ile
                115                 120                 125

Glu Asn Val Ile Thr Ala Arg Glu Leu Ser Arg His Ile Glu Asp Lys
                130                 135                 140

Phe Ala Asn Tyr Ala Ala Ser Lys Glu Lys Asp Asp Asn Asp Leu Ser
145                 150                 155                 160

Ile Leu Val Gly Gly Ala Gly Phe Thr Gly Val Glu Phe Leu Gly Glu
                165                 170                 175

Leu Thr Asp Arg Ile Pro Glu Leu Cys Ser Lys Tyr Gly Val Asp Gln
```

```
                    180                 185                 190
Asn Lys Val Lys Ile Thr Cys Val Glu Ala Ala Pro Lys Met Leu Pro
            195                 200                 205

Met Phe Ser Glu Glu Leu Val Asn His Ala Val Ser Tyr Leu Glu Asp
        210                 215                 220

Arg Gly Val Glu Phe Lys Ile Ala Thr Pro Ile Val Ala Cys Asn Glu
225                 230                 235                 240

Lys Gly Phe Val Val Glu Val Asp Gly Glu Lys Gln Gln Leu Asn Ala
                245                 250                 255

Gly Thr Ser Val Trp Ala Ala Gly Val Arg Gly Ser Lys Leu Met Glu
            260                 265                 270

Glu Ser Phe Glu Gly Val Lys Arg Gly Arg Ile Val Thr Lys Gln Asp
        275                 280                 285

Leu Thr Ile Asn Gly Tyr Asp Asn Ile Phe Val Ile Gly Asp Cys Ser
    290                 295                 300

Ala Phe Ile Pro Ala Gly Glu Glu Arg Pro Leu Pro Thr Thr Ala Gln
305                 310                 315                 320

Ile Ala Met Gln Gln Gly Glu Ser Val Ala Lys Asn Ile Lys Arg Ile
                325                 330                 335

Leu Asn Gly Glu Ser Thr Glu Glu Phe Glu Tyr Val Asp Arg Gly Thr
            340                 345                 350

Val Cys Ser Leu Gly Ser His Asp Gly Val Gly Met Val Phe Gly Lys
        355                 360                 365

Pro Ile Ala Gly Lys Lys Ala Ala Phe Met Lys Val Ile Asp Thr
    370                 375                 380

Arg Ala Val Phe Lys Ile Gly Gly Ile Gly Leu Ala Phe Lys Lys Gly
385                 390                 395                 400

Lys Phe

<210> SEQ ID NO 38
<211> LENGTH: 438
<212> TYPE: PRT
<213> ORGANISM: Staphylococcus aureus

<400> SEQUENCE: 38

Met Pro Lys Ile Val Val Gly Ala Val Gly Gly Ala Thr Cys
1               5                   10                  15

Ala Ser Gln Ile Arg Arg Leu Asp Lys Glu Ser Asp Ile Ile Phe
                20                  25                  30

Glu Lys Asp Arg Asp Met Ser Phe Ala Asn Cys Ala Leu Pro Tyr Val
            35                  40                  45

Ile Gly Glu Val Val Asp Arg Lys Tyr Ala Leu Ala Tyr Thr Pro
    50                  55                  60

Glu Lys Phe Tyr Asp Arg Lys Gln Ile Thr Val Lys Thr Tyr His Glu
65                  70                  75                  80

Val Ile Ala Ile Asn Asp Glu Arg Gln Thr Val Thr Val Leu Asn Arg
                85                  90                  95

Lys Thr Asn Glu Gln Phe Glu Glu Ser Tyr Lys Leu Ile Leu Ser
            100                 105                 110

Pro Gly Ala Ser Ala Asn Ser Leu Gly Phe Glu Ser Asp Ile Thr Phe
        115                 120                 125

Thr Leu Arg Asn Leu Glu Asp Thr Asp Ala Ile Asp Gln Phe Ile Lys
    130                 135                 140

Ala Asn Gln Val Asp Lys Val Leu Val Val Gly Ala Gly Tyr Val Ser
145                 150                 155                 160
```

Leu Glu Val Leu Glu Asn Leu Tyr Glu Arg Gly Leu His Pro Thr Leu
            165                 170                 175

Ile His Arg Ser Asp Lys Ile Asn Lys Leu Met Asp Ala Asp Met Asn
            180                 185                 190

Gln Pro Ile Leu Asp Glu Leu Asp Lys Arg Glu Ile Pro Tyr Arg Leu
            195                 200                 205

Asn Glu Glu Ile Asp Ala Ile Asn Gly Asn Gln Ile Thr Phe Lys Ser
210                 215                 220

Gly Lys Val Glu His Tyr Asp Met Ile Ile Glu Gly Val Gly Thr His
225                 230                 235                 240

Pro Asn Ser Lys Phe Ile Glu Ser Ser Asn Ile Lys Leu Asp Arg Lys
                245                 250                 255

Gly Phe Ile Pro Val Asn Asp Lys Phe Glu Thr Asn Val Pro Asn Ile
                260                 265                 270

Tyr Ala Ile Gly Asp Ile Ala Thr Ser His Tyr Arg His Val Asp Leu
            275                 280                 285

Pro Ala Ser Val Pro Leu Ala Trp Gly Ala His Arg Ala Ala Ser Ile
290                 295                 300

Val Ala Glu Gln Ile Ala Gly Asn Asp Thr Ile Glu Phe Lys Gly Phe
305                 310                 315                 320

Leu Gly Asn Asn Ile Val Lys Phe Phe Asp Tyr Thr Phe Ala Ser Val
                325                 330                 335

Gly Val Lys Pro Asn Glu Leu Lys Gln Phe Asp Tyr Lys Met Val Glu
                340                 345                 350

Val Thr Gln Gly Ala His Ala Asn Tyr Tyr Pro Gly Asn Ser Pro Leu
            355                 360                 365

His Leu Arg Val Tyr Tyr Asp Thr Ser Asn Arg Gln Ile Leu Arg Ala
            370                 375                 380

Ala Ala Val Gly Lys Glu Gly Ala Asp Lys Arg Ile Asp Val Leu Ser
385                 390                 395                 400

Met Ala Met Met Asn Gln Leu Thr Val Asp Glu Leu Thr Glu Phe Glu
                405                 410                 415

Val Ala Tyr Ala Pro Pro Tyr Ser His Pro Lys Asp Leu Ile Asn Met
            420                 425                 430

Ile Gly Tyr Lys Ala Lys
            435

<210> SEQ ID NO 39
<211> LENGTH: 293
<212> TYPE: PRT
<213> ORGANISM: Staphylococcus aureus

<400> SEQUENCE: 39

Met Ala Thr Ile Ser Ala Lys Leu Val Lys Glu Leu Arg Lys Lys Thr
1               5                   10                  15

Gly Ala Gly Met Met Asp Cys Lys Lys Ala Leu Thr Glu Thr Asp Gly
            20                  25                  30

Asp Ile Asp Lys Ala Ile Asp Tyr Leu Arg Glu Lys Gly Ile Ala Lys
        35                  40                  45

Ala Ala Lys Lys Ala Asp Arg Ile Ala Ala Glu Gly Leu Val His Val
    50                  55                  60

Glu Thr Lys Gly Asn Asp Ala Val Ile Val Glu Ile Asn Ser Glu Thr
65                  70                  75                  80

Asp Phe Val Ala Arg Asn Glu Gly Phe Gln Glu Leu Val Lys Glu Ile
                85                  90                  95

-continued

```
Ala Asn Gln Val Leu Asp Thr Lys Ala Glu Thr Val Glu Ala Leu Met
            100                 105                 110
Glu Thr Thr Leu Pro Asn Gly Lys Ser Val Asp Glu Arg Ile Lys Glu
        115                 120                 125
Ala Ile Ser Thr Ile Gly Glu Lys Leu Ser Val Arg Arg Phe Ala Ile
    130                 135                 140
Arg Thr Lys Thr Asp Asn Asp Ala Phe Gly Ala Tyr Leu His Met Gly
145                 150                 155                 160
Gly Arg Ile Gly Val Leu Thr Val Val Glu Gly Ser Thr Asp Glu Glu
                165                 170                 175
Ala Ala Arg Asp Val Ala Met His Ile Ala Ala Ile Asn Pro Lys Tyr
            180                 185                 190
Val Ser Ser Glu Gln Val Ser Glu Glu Ile Asn His Glu Arg Glu
        195                 200                 205
Val Leu Lys Gln Gln Ala Leu Asn Glu Gly Lys Pro Glu Asn Ile Val
    210                 215                 220
Glu Lys Met Val Glu Gly Arg Leu Arg Lys Tyr Leu Gln Glu Ile Cys
225                 230                 235                 240
Ala Val Asp Gln Asp Phe Val Lys Asn Pro Asp Val Thr Val Glu Ala
                245                 250                 255
Phe Leu Lys Thr Lys Gly Gly Lys Leu Val Asp Phe Val Arg Tyr Glu
            260                 265                 270
Val Gly Glu Gly Met Glu Lys Arg Glu Glu Asn Phe Ala Asp Glu Val
        275                 280                 285
Lys Gly Gln Met Lys
    290

<210> SEQ ID NO 40
<211> LENGTH: 475
<212> TYPE: PRT
<213> ORGANISM: Staphylococcus aureus

<400> SEQUENCE: 40

Met His Phe Glu Thr Val Ile Gly Leu Glu Val His Val Glu Leu Lys
1               5                   10                  15
Thr Asp Ser Lys Met Phe Ser Pro Ser Pro Ala His Phe Gly Ala Glu
            20                  25                  30
Pro Asn Ser Asn Thr Asn Val Ile Asp Leu Ala Tyr Pro Gly Val Leu
        35                  40                  45
Pro Val Val Asn Lys Arg Ala Val Asp Trp Ala Met Arg Ala Ala Met
    50                  55                  60
Ala Leu Asn Met Glu Ile Ala Thr Glu Ser Lys Phe Asp Arg Lys Asn
65                  70                  75                  80
Tyr Phe Tyr Pro Asp Asn Pro Lys Ala Tyr Gln Ile Ser Gln Phe Asp
                85                  90                  95
Gln Pro Ile Gly Glu Asn Gly Tyr Ile Asp Ile Glu Val Asp Gly Glu
            100                 105                 110
Thr Lys Arg Ile Gly Ile Thr Arg Leu His Met Glu Glu Asp Ala Gly
        115                 120                 125
Lys Ser Thr His Lys Gly Glu Tyr Ser Leu Val Asp Leu Asn Arg Gln
    130                 135                 140
Gly Thr Pro Leu Ile Glu Ile Val Ser Glu Pro Asp Ile Arg Ser Pro
145                 150                 155                 160
Lys Glu Ala Tyr Ala Tyr Leu Glu Lys Leu Arg Ser Ile Ile Gln Tyr
                165                 170                 175
```

Thr Gly Val Ser Asp Val Lys Met Glu Glu Gly Ser Leu Arg Cys Asp
            180                 185                 190

Ala Asn Ile Ser Leu Arg Pro Tyr Gly Gln Glu Lys Phe Gly Thr Lys
        195                 200                 205

Ala Glu Leu Lys Asn Leu Asn Ser Phe Asn Tyr Val Arg Lys Gly Leu
    210                 215                 220

Glu Tyr Glu Glu Lys Arg Gln Glu Glu Leu Leu Ser Gly Gly Glu
225                 230                 235                 240

Ile Gly Gln Glu Thr Arg Arg Phe Asp Glu Ser Thr Gly Lys Thr Ile
                245                 250                 255

Leu Met Arg Val Lys Glu Gly Ser Asp Asp Tyr Arg Tyr Phe Pro Glu
            260                 265                 270

Pro Asp Ile Val Pro Leu Tyr Ile Asp Asp Ala Trp Lys Glu Arg Val
        275                 280                 285

Arg Gln Thr Ile Pro Glu Leu Pro Asp Glu Arg Lys Ala Lys Tyr Val
    290                 295                 300

Asn Glu Leu Gly Leu Pro Ala Tyr Asp Ala His Val Leu Thr Leu Thr
305                 310                 315                 320

Lys Glu Met Ser Asp Phe Phe Glu Ser Thr Ile Glu His Gly Ala Asp
                325                 330                 335

Val Lys Leu Thr Ser Asn Trp Leu Met Gly Val Asn Glu Tyr Leu
            340                 345                 350

Asn Lys Asn Gln Val Glu Leu Leu Asp Thr Lys Leu Thr Pro Glu Asn
        355                 360                 365

Leu Ala Gly Met Ile Lys Leu Ile Glu Asp Gly Thr Met Ser Ser Lys
    370                 375                 380

Ile Ala Lys Lys Val Phe Pro Glu Leu Ala Ala Lys Gly Gly Asn Ala
385                 390                 395                 400

Lys Gln Ile Met Glu Asp Asn Gly Leu Val Gln Ile Ser Asp Glu Ala
                405                 410                 415

Thr Leu Leu Lys Phe Val Asn Glu Ala Leu Asp Asn Asn Glu Gln Ser
            420                 425                 430

Val Glu Asp Tyr Lys Asn Gly Lys Gly Lys Ala Met Gly Phe Leu Val
        435                 440                 445

Gly Gln Ile Met Lys Ala Ser Lys Gly Gln Ala Asn Pro Gln Leu Val
    450                 455                 460

Asn Gln Leu Leu Lys Gln Glu Leu Asp Lys Arg
465                 470                 475

<210> SEQ ID NO 41
<211> LENGTH: 309
<212> TYPE: PRT
<213> ORGANISM: Staphylococcus aureus

<400> SEQUENCE: 41

Met Ala Lys Thr Tyr Ile Phe Gly His Lys Asn Pro Asp Thr Asp Ala
1               5                   10                  15

Ile Ser Ser Ala Ile Ile Met Ala Glu Phe Glu Gln Leu Arg Gly Asn
            20                  25                  30

Ser Gly Ala Lys Ala Tyr Arg Leu Gly Asp Val Ser Ala Glu Thr Gln
        35                  40                  45

Phe Ala Leu Asp Thr Phe Asn Val Pro Ala Pro Glu Leu Leu Thr Asp
    50                  55                  60

Asp Leu Asp Gly Gln Asp Val Ile Leu Val Asp His Asn Glu Phe Gln
65                  70                  75                  80

```
Gln Ser Ser Asp Thr Ile Ala Ser Ala Thr Ile Lys His Val Ile Asp
                85                  90                  95

His His Arg Ile Ala Asn Phe Glu Thr Ala Gly Pro Leu Cys Tyr Arg
            100                 105                 110

Ala Glu Pro Val Gly Cys Thr Ala Thr Ile Leu Tyr Lys Met Phe Arg
        115                 120                 125

Glu Arg Gly Phe Glu Ile Lys Pro Glu Ile Ala Gly Leu Met Leu Ser
    130                 135                 140

Ala Ile Ile Ser Asp Ser Leu Leu Phe Lys Ser Pro Thr Cys Thr Gln
145                 150                 155                 160

Gln Asp Val Lys Ala Ala Glu Glu Leu Lys Asp Ile Ala Lys Val Asp
                165                 170                 175

Ile Gln Lys Tyr Gly Leu Asp Met Leu Lys Ala Gly Ala Ser Thr Thr
            180                 185                 190

Asp Lys Ser Val Glu Phe Leu Leu Asn Met Asp Ala Lys Ser Phe Thr
        195                 200                 205

Met Gly Asp Tyr Val Thr Arg Ile Ala Gln Val Asn Ala Val Asp Leu
    210                 215                 220

Asp Glu Val Leu Asn Arg Lys Glu Asp Leu Lys Glu Met Leu Ala
225                 230                 235                 240

Val Ser Ala Gln Glu Lys Tyr Asp Leu Phe Val Leu Val Thr Asp
                245                 250                 255

Ile Ile Asn Ser Asp Ser Lys Ile Leu Val Val Gly Ala Glu Lys Asp
            260                 265                 270

Lys Val Gly Glu Ala Phe Asn Val Gln Leu Glu Asp Met Ala Phe
        275                 280                 285

Leu Ser Gly Val Val Ser Arg Lys Lys Gln Ile Val Pro Gln Ile Thr
    290                 295                 300

Glu Ala Leu Thr Lys
305

<210> SEQ ID NO 42
<211> LENGTH: 325
<212> TYPE: PRT
<213> ORGANISM: Staphylococcus aureus

<400> SEQUENCE: 42

Met Ala Gln Met Thr Met Val Gln Ala Ile Asn Asp Ala Leu Lys Thr
1               5                   10                  15

Glu Leu Lys Asn Asp Gln Asp Val Leu Ile Phe Gly Glu Asp Val Gly
                20                  25                  30

Val Asn Gly Gly Val Phe Arg Val Thr Glu Gly Leu Gln Lys Glu Phe
            35                  40                  45

Gly Glu Asp Arg Val Phe Asp Thr Pro Leu Ala Glu Ser Gly Ile Gly
        50                  55                  60

Gly Leu Ala Met Gly Leu Ala Val Glu Gly Phe Arg Pro Val Met Glu
65                  70                  75                  80

Val Gln Phe Leu Gly Phe Val Phe Glu Val Phe Asp Ala Ile Ala Gly
                85                  90                  95

Gln Ile Ala Arg Thr Arg Phe Arg Ser Gly Gly Thr Lys Thr Ala Pro
            100                 105                 110

Val Thr Ile Arg Ser Pro Phe Gly Gly Gly Val His Thr Pro Glu Leu
        115                 120                 125

His Ala Asp Asn Leu Glu Gly Ile Leu Ala Gln Ser Pro Gly Leu Lys
    130                 135                 140
```

```
Val Val Ile Pro Ser Gly Pro Tyr Asp Ala Lys Gly Leu Leu Ile Ser
145                 150                 155                 160

Ser Ile Arg Ser Asn Asp Pro Val Val Tyr Leu Glu His Met Lys Leu
            165                 170                 175

Tyr Arg Ser Phe Arg Glu Glu Val Pro Glu Glu Glu Tyr Thr Ile Asp
            180                 185                 190

Ile Gly Lys Ala Asn Val Lys Lys Glu Gly Asn Asp Ile Ser Ile Ile
            195                 200                 205

Thr Tyr Gly Ala Met Val Gln Glu Ser Met Lys Ala Ala Glu Glu Leu
            210                 215                 220

Glu Lys Asp Gly Tyr Ser Val Glu Val Ile Asp Leu Arg Thr Val Gln
225                 230                 235                 240

Pro Ile Asp Val Asp Thr Ile Val Ala Ser Val Glu Lys Thr Gly Arg
            245                 250                 255

Ala Val Val Val Gln Glu Ala Gln Arg Gln Ala Gly Val Gly Ala Ala
            260                 265                 270

Val Val Ala Glu Leu Ser Glu Arg Ala Ile Leu Ser Leu Glu Ala Pro
            275                 280                 285

Ile Gly Arg Val Ala Ala Ala Asp Thr Ile Tyr Pro Phe Thr Gln Ala
            290                 295                 300

Glu Asn Val Trp Leu Pro Asn Lys Asn Asp Ile Ile Glu Lys Ala Lys
305                 310                 315                 320

Glu Thr Leu Glu Phe
                325

<210> SEQ ID NO 43
<211> LENGTH: 142
<212> TYPE: PRT
<213> ORGANISM: Staphylococcus aureus

<400> SEQUENCE: 43

Met Lys Tyr Asp Asp Phe Ile Val Gly Glu Thr Phe Lys Thr Lys Ser
1               5                   10                  15

Leu His Ile Thr Glu Glu Ile Ile Gln Phe Ala Thr Thr Phe Asp
            20                  25                  30

Pro Gln Tyr Met His Ile Asp Lys Glu Lys Ala Glu Gln Ser Arg Phe
            35                  40                  45

Lys Gly Ile Ile Ala Ser Gly Met His Thr Leu Ser Ile Ser Phe Lys
        50                  55                  60

Leu Trp Val Glu Glu Gly Lys Tyr Gly Glu Glu Val Val Ala Gly Thr
65                  70                  75                  80

Gln Met Asn Asn Val Lys Phe Ile Lys Pro Val Tyr Pro Gly Asn Thr
                85                  90                  95

Leu Tyr Val Ile Ala Glu Ile Thr Asn Lys Lys Ser Ile Lys Lys Glu
            100                 105                 110

Asn Gly Leu Val Thr Val Ser Leu Ser Thr Tyr Asn Glu Asn Glu Glu
            115                 120                 125

Ile Val Phe Lys Gly Glu Val Thr Ala Leu Ile Asn Asn Ser
            130                 135                 140

<210> SEQ ID NO 44
<211> LENGTH: 24
<212> TYPE: DNA
<213> ORGANISM: Artificial
<220> FEATURE:
<223> OTHER INFORMATION: Synthetic
```

```
<400> SEQUENCE: 44
atgaatacaa tcaaaactac gaaa                                              24

<210> SEQ ID NO 45
<211> LENGTH: 37
<212> TYPE: DNA
<213> ORGANISM: Artificial
<220> FEATURE:
<223> OTHER INFORMATION: Synthetic

<400> SEQUENCE: 45
cttctcatcg tcatctgatt tcaaaatcca tttttga                                37

<210> SEQ ID NO 46
<211> LENGTH: 43
<212> TYPE: DNA
<213> ORGANISM: Artificial
<220> FEATURE:
<223> OTHER INFORMATION: Synthetic

<400> SEQUENCE: 46
actctaggtc tcactcccat ctgaaacaac attatgacca aat                         43

<210> SEQ ID NO 47
<211> LENGTH: 45
<212> TYPE: DNA
<213> ORGANISM: Artificial
<220> FEATURE:
<223> OTHER INFORMATION: Synthetic

<400> SEQUENCE: 47
atggtaggtc tcatatcata aaggatttaa cggtaattca ttact                       45

<210> SEQ ID NO 48
<211> LENGTH: 43
<212> TYPE: DNA
<213> ORGANISM: Artificial
<220> FEATURE:
<223> OTHER INFORMATION: Synthetic

<400> SEQUENCE: 48
atggtaggtc tcactccgat aagtcaaatg gcaaactaaa agt                         43

<210> SEQ ID NO 49
<211> LENGTH: 40
<212> TYPE: DNA
<213> ORGANISM: Artificial
<220> FEATURE:
<223> OTHER INFORMATION: Synthetic

<400> SEQUENCE: 49
atggtaggtc tcatatcatt tcatgcttcc gtgtacagtt                             40

<210> SEQ ID NO 50
<211> LENGTH: 43
<212> TYPE: DNA
<213> ORGANISM: Artificial
<220> FEATURE:
<223> OTHER INFORMATION: Synthetic

<400> SEQUENCE: 50
atggtaggtc tcactccgct tatactgtta ctaaaccaca aac                         43

<210> SEQ ID NO 51
<211> LENGTH: 44
<212> TYPE: DNA
```

```
-continued

<213> ORGANISM: Artificial
<220> FEATURE:
<223> OTHER INFORMATION: Synthetic

<400> SEQUENCE: 51
atggtaggtc tcatatcatt tatattgtgg gatgtcgaag tatt                44

<210> SEQ ID NO 52
<211> LENGTH: 43
<212> TYPE: DNA
<213> ORGANISM: Artificial
<220> FEATURE:
<223> OTHER INFORMATION: Synthetic

<400> SEQUENCE: 52
actctaggtc tcactccaaa gaagattcaa aagaagaaca aat                 43

<210> SEQ ID NO 53
<211> LENGTH: 40
<212> TYPE: DNA
<213> ORGANISM: Artificial
<220> FEATURE:
<223> OTHER INFORMATION: Synthetic

<400> SEQUENCE: 53
atggtaggtc tcatatcagc tatcttcatc agacggccca                    40
```